US008623812B2

(12) United States Patent
Kieliszewski et al.

(10) Patent No.: US 8,623,812 B2
(45) Date of Patent: Jan. 7, 2014

(54) CROSS-LINKABLE GLYCOPROTEINS AND METHODS OF MAKING THE SAME

(75) Inventors: Marcia J. Kieliszewski, Albany, OH (US); Michael Held, West Lafayette, IN (US); Li Tan, Athens, OH (US)

(73) Assignee: Ohio University, Athens, OH (US)

( * ) Notice: Subject to any disclaimer, the term of this patent is extended or adjusted under 35 U.S.C. 154(b) by 1440 days.

(21) Appl. No.: 11/568,102

(22) PCT Filed: Apr. 19, 2005

(86) PCT No.: PCT/US2005/013252
§ 371 (c)(1),
(2), (4) Date: Jul. 31, 2007

(87) PCT Pub. No.: WO2005/110015
PCT Pub. Date: Nov. 24, 2005

(65) Prior Publication Data
US 2008/0262198 A1   Oct. 23, 2008

Related U.S. Application Data

(60) Provisional application No. 60/563,349, filed on Apr. 19, 2004, provisional application No. 60/653,236, filed on Feb. 15, 2005.

(51) Int. Cl.
*A61K 38/04* (2006.01)
*A01N 37/18* (2006.01)

(52) U.S. Cl.
USPC .......................................... 514/3.1

(58) Field of Classification Search
None
See application file for complete search history.

(56) References Cited

U.S. PATENT DOCUMENTS

| | | | |
|---|---|---|---|
| 3,664,925 A | 5/1972 | Sonenberg et al. |
| 4,056,520 A | 11/1977 | Sonenberg et al. |
| 4,374,829 A | 2/1983 | Harris et al. |
| 4,478,827 A | 10/1984 | Haber et al. |
| 4,683,195 A | 7/1987 | Mullis et al. |
| 4,683,202 A | 7/1987 | Mullis |
| 4,940,838 A | 7/1990 | Schilperoort et al. |
| 4,956,282 A | 9/1990 | Goodman et al. |
| 4,965,188 A | 10/1990 | Mullis et al. |
| 5,034,322 A | 7/1991 | Rogers et al. |
| 5,350,836 A | 9/1994 | Kopchick et al. |
| 5,352,596 A | 10/1994 | Cheung et al. |
| 5,352,605 A | 10/1994 | Fraley et al. |
| 5,474,925 A | 12/1995 | Maliyakal et al. |
| 5,501,967 A | 3/1996 | Offringa et al. |
| 5,506,107 A | 4/1996 | Cunningham et al. |
| 5,534,617 A | 7/1996 | Cunningham et al. |
| 5,550,038 A | 8/1996 | Goodman et al. |
| 5,584,807 A | 12/1996 | McCabe |
| 5,629,175 A | 5/1997 | Goodman et al. |
| 5,637,686 A | 6/1997 | Tjian et al. |
| 5,641,670 A | 6/1997 | Treco et al. |
| 5,646,029 A | 7/1997 | Chen et al. |
| 5,650,307 A | 7/1997 | Sijmons et al. |
| 5,681,809 A | 10/1997 | Kopchick et al. |
| 5,695,971 A | 12/1997 | Kadokami et al. |
| 5,723,755 A | 3/1998 | Fortin |
| 5,728,810 A | 3/1998 | Lewis et al. |
| 5,733,771 A | 3/1998 | Lewis et al. |
| 5,756,677 A | 5/1998 | Lewis et al. |
| 5,763,394 A | 6/1998 | O'Connor et al. |
| 5,780,279 A | 7/1998 | Matthews et al. |
| 5,821,089 A | 10/1998 | Gruskin et al. |
| 5,830,747 A | 11/1998 | Chen et al. |
| 5,849,535 A | 12/1998 | Cunningham et al. |
| 5,958,879 A | 9/1999 | Kopchick et al. |
| 5,989,894 A | 11/1999 | Lewis et al. |
| 5,994,099 A | 11/1999 | Lewis et al. |
| 6,020,169 A | 2/2000 | Lee et al. |
| 6,033,895 A | 3/2000 | Garger et al. |
| 6,080,560 A | 6/2000 | Russell et al. |
| 6,096,547 A | 8/2000 | Goodman et al. |
| 6,210,950 B1 | 4/2001 | Johnson et al. |
| 6,225,080 B1 | 5/2001 | Uhl et al. |
| 6,355,776 B1 | 3/2002 | Ferrari et al. |
| 6,486,382 B1 | 11/2002 | Gordan-Kamm et al. |
| 6,548,642 B1 | 4/2003 | Kieliszewski |
| 6,570,062 B1 | 5/2003 | Kieliszewski |
| 6,583,115 B1 | 6/2003 | Kopchick et al. |
| 6,639,050 B1 | 10/2003 | Kieliszewski |
| 6,680,426 B2 | 1/2004 | Daniell et al. |
| 6,774,283 B1 | 8/2004 | Goodman et al. |
| 6,787,336 B1 | 9/2004 | Kopchick et al. |

(Continued)

FOREIGN PATENT DOCUMENTS

| | | |
|---|---|---|
| CA | 2296813 | 5/2011 |
| EP | 1 156 060 A1 | 11/2001 |
| EP | 1 156 060 B1 | 6/2007 |
| EP | 2133427 | 12/2009 |
| JP | 2005-087172 | 4/2005 |
| NZ | 548513 | 9/2010 |
| WO | WO 90/04788 | 5/1990 |
| WO | WO 92/03478 | 3/1992 |
| WO | WO 92/09690 | 6/1992 |
| WO | WO 92/20713 | 11/1992 |

(Continued)

OTHER PUBLICATIONS

Office Action in U.S. Appl. No. 10/418,032, dated Feb. 8, 2005.
Office Action in U.S. Appl. No. 10/418,032, dated May 12, 2005.
Office Action in U.S. Appl. No. 10/418,032, dated Apr. 13, 2006.
Office Action in U.S. Appl. No. 10/418,032, dated Sep. 14, 2006.
Office Action in U.S. Appl. No. 10/418,032, dated Jan. 12, 2007.
Office Action in U.S. Appl. No. 10/437,708, dated Aug. 11, 2004.
Office Action in U.S. Appl. No. 10/437,708, dated Nov. 26, 2004.
Office Action in U.S. Appl. No. 10/437,708, dated May 5, 2005.
Office Action in U.S. Appl. No. 10/437,708, dated Oct. 3, 2005.
Office Action in U.S. Appl. No. 10/437,708, dated Jun. 8, 2006.

(Continued)

*Primary Examiner* — Thomas Heard
(74) *Attorney, Agent, or Firm* — Dinsmore & Shohl, LLP

(57) ABSTRACT

Non-naturally occurring peptides/polypeptides/proteins comprising the crosslinking motif, Tyr-X-Tyr, wherein X is any amino acid, and methods of preparing the same.

13 Claims, 42 Drawing Sheets

(56) References Cited

U.S. PATENT DOCUMENTS

| | | | |
|---|---|---|---|
| 7,378,506 B2 | 5/2008 | Kieliszewski | |
| 7,388,081 B2 | 6/2008 | Seki et al. | |
| 2002/0127652 A1 | 9/2002 | Schambye et al. | |
| 2002/0160944 A1 | 10/2002 | Boime et al. | |
| 2002/0162135 A1 | 10/2002 | Daniell | |
| 2002/0174453 A1 | 11/2002 | Daniell et al. | |
| 2003/0009783 A1 | 1/2003 | Daniell et al. | |
| 2003/0036181 A1 | 2/2003 | Okkels et al. | |
| 2003/0041353 A1 | 2/2003 | Daniell et al. | |
| 2003/0167531 A1 | 9/2003 | Russell et al. | |
| 2003/0204864 A1 | 10/2003 | Daniell | |
| 2004/0009555 A1 | 1/2004 | Kieliszewski | |
| 2004/0009557 A1 | 1/2004 | Kieliszewski | |
| 2004/0230032 A1 | 11/2004 | Kieliszewski | |
| 2005/0074838 A1* | 4/2005 | Kieliszewski | 435/69.1 |
| 2006/0026719 A1 | 2/2006 | Kieliszewski | |
| 2006/0148680 A1 | 7/2006 | Kieliszewski | |
| 2006/0252120 A1 | 11/2006 | Kieliszewski | |
| 2007/0039073 A1 | 2/2007 | Kieliszewski | |
| 2008/0242834 A1 | 10/2008 | Kieliszewski et al. | |
| 2009/0030185 A1 | 1/2009 | Kieliszewski | |
| 2010/0028993 A1 | 2/2010 | Kieliszewski | |
| 2010/0029548 A1 | 2/2010 | Kieliszewski | |
| 2010/0261874 A1 | 10/2010 | Kieliszewski | |
| 2011/0003340 A1 | 1/2011 | Kieliszewski | |
| 2011/0217766 A1 | 9/2011 | Kieliszewski | |
| 2011/0230404 A1 | 9/2011 | Kieliszewski | |
| 2012/0077226 A1 | 3/2012 | Kieliszewski | |

FOREIGN PATENT DOCUMENTS

| | | | |
|---|---|---|---|
| WO | WO 93/00109 | 1/1993 | |
| WO | WO 95/15377 | 6/1995 | |
| WO | WO 97/11178 | 3/1997 | |
| WO | WO 99/03978 | 1/1999 | |
| WO | WO 00/26354 | 5/2000 | |
| WO | 01/16339 | 3/2001 | |
| WO | WO 01/49830 | 7/2001 | |
| WO | WO 01/75132 | 10/2001 | |
| WO | WO 01/78503 | 10/2001 | |
| WO | WO 02/37313 | 5/2002 | |
| WO | 03/064619 | 8/2003 | |
| WO | WO 2004/094590 | * 11/2004 | |
| WO | 2004103275 | 12/2004 | |
| WO | WO 2005/069845 | 8/2005 | |
| WO | WO 2005/110015 | 11/2005 | |
| WO | 2006035442 | 4/2006 | |
| WO | WO 2007/008708 | 1/2007 | |
| WO | 2008/008766 | 1/2008 | |

OTHER PUBLICATIONS

Office Action in U.S. Appl. No. 10/437,708, dated Feb. 28, 2007.
Office Action in U.S. Appl. No. 11/173,811, dated Jun. 12, 2007.
Office Action in U.S. Appl. No. 11/243,295, dated Nov. 15, 2006.
Office Action in U.S. Appl. No. 11/243,295, dated Jul. 25, 2007.
Office Action in U.S. Appl. No. 11/036,257, dated Oct. 4, 2006.
Office Action in U.S. Appl. No. 11/036,257, dated Feb. 26, 2007.
Office Action in U.S. Appl. No. 11/036,256, dated Jul. 26, 2006.
Office Action in U.S. Appl. No. 11/036,256, dated Oct. 4, 2006.
Office Action in U.S. Appl. No. 11/036,256, dated Jul. 5, 2007.
International Search Report in Application No. PCT/US05/13252, dated Oct. 2, 2006.
Written Opinion in Application No. PCT/US05/13252, dated Feb. 10, 2006.
International Preliminary Report on Patentability in Application No. PCT/US05/13252, dated Nov. 7, 2006.
International Search Report in Application No. PCT/US05/01160, dated May 24, 2006.
Written Opinion in Application No. PCT/US05/01160, dated May 24, 2006.
International Preliminary Report on Patentability in Application No. PCT/US05/01160, dated Aug. 7, 2006.
International Search Report and Written Opinion in Application No. PCT/US04/11174, dated Feb. 15, 2005.
International Preliminary Report on Patentability in Application No. PCT/US04/11174, dated Oct. 21, 2005.
International Search Report in Application No. PCT/US01/12336, dated Jan. 27, 2003.
International Preliminary Examination Report in Application No. PCT/US01/12336, dated Jan. 16, 2004.
International Search Report in Application No. PCT/US98/15803, dated Dec. 8, 1998.
Search Report in EP Application No. 01927057.8, dated May 26, 2004.
Examination Report in EP Application No. 01927057.8, dated Jul. 31, 2006.
Search Report in EP Application No. 98944431.0, dated Oct. 15, 2004.
Abstract No. XP-002295046 for Accession No. P41479, created Nov. 1, 1995.
GENBANK Accession No. AF227194 dated Feb. 21, 2003.
GENBANK Accession No. D41504 dated Nov. 15, 1994.
GENBANK Accession No. P41479 dated Nov. 1, 1995.
GENBANK Accession No. S50755 dated May 8, 1993.
GENBANK Accession No. X69156 dated Nov. 14, 2006.
Abdel-Meguid et al., "Three Dimensional Structure of a genetically engineered variate of porcine growth hormone", Proc. Nat. Acad. Sci. USA, vol. 64 (1987), pp. 6434-6437.
Altschul et al., "Basic Local Assignment Search Took", J. Mol. Biol., vol. 215 (1990), pp. 403-410.
Amado et al., "Identification and characterization of large galactosyltransferase gene families", Biochimica et Biophysica Acta, vol. 1473 (1999), pp. 35-53.
An, et al., "Binary Vectors", Plant Molecular Biology Manual, vol. A3 (1988), pp. 1-19.
An, "High Efficiency Transformation of Cultured Tobacco Cells", Plant Physiol, vol. 79 (1985), pp. 568-570.
Anderson, et al., "The Chemcial characterization of the gum exudates from eight Australian Acacia species . . . ", Food Hydrocolloids, vol. 2 (1988), pp. 329-336.
Aspinall, "Plant gums", in The Carbohydrates, (Ed. Pigman & Horton, Academic Press, NY, 1970), vol. 2B, pp. 522-536.
Aspinall, et al., "The location of a α-D-galactopyranose residues in gum arabic", Carbohyd. Res., vol. 157 (1986), pp. 257-260.
Ausubel, "Chapter 3: Enzymatic Manipulation of DNA and RNA", in Current Protocols in Molecular Biology, (John Wiley & Sons, Inc., NY, 1995), pp. 3.2.1-3.3.2 and 3.16:1-3.16.
Averyhart-Fullard et al., "A hydroxyproline-rich protein in the soybean cell wall", Proc. Nat. Acad. Sci. USA, vol. 85 (1988), pp. 1082-1085.
Bacic et al., "Fine Structure of the Arabinogalactan-Protein from *Lollium multiflorum*", Carbohyd. Res., vol. 162 (1987), pp. 85-93.
Bailon, et al., "Rational Design of a Potent, Long-Lasting Form of Interferon: A 40 kDa Branched Polyethylene . . . ", Bioconjugate Chem., vol. 12, No. 2 (2001), pp. 195-202.
Baldwin et al., "The ptl1 gene expressed in the transmitting tissue of Antirrhinum encodes an extensin-like protein", The Plant Journal, vol. 2, No. 5 (1992), pp. 733-739.
Bell et al., "Crystallization and Preliminary X-ray Characterization of Bovine Growth Hormone", J. Biol. Chem., vol. 260, No. 14 (1985), pp. 8520-8525.
Benfey et al., "Sequence Requirements of the 5-Enolpyruvylshikimate-3-phosphate Synthase 5'-Upstream Region . . . ", Plant Cell, vol. 2 (1990), pp. 849-856.
Bergman et al., "Amino Acid Analysis by High . . . ", Advanced Methods in Protein Microsequence Analysis (Ed. Wittmann-Liebold, Springer-Vertag, Berlin, 1986), pp. 45-55.
Bidney et al., "Micrprojectile bombardment of plant tissues increases transformation frequency by *Agrobacteruim tumefaciens*", Plant Molec. Biol., vol. 18 (1992), pp. 301-313.
Borner et al., "Identification of Glycosylphosphatidylinositol-Anchored Proteins in Arabidopsis. A Proteomic . . . ", Plant Physiology, vol. 132 (2003), pp. 568-577.

(56) References Cited

OTHER PUBLICATIONS

Boutin et al., "Cloning and expression of the rat prolactin receptor, a member of the growth hormone/prolactin receptor gene family", Cell, vol. 53, No. 1 (1998), pp. 69-77.
Breton et al., "Sequence-Function Relationships of Prokaryotic and Eukaryotic Galactosyltransferases", J. Biochem, vol. 123 (Tokyo) (1998), pp. 1000-1009.
Cabanes-Macheteau et al., "N-glycosylation of a mouse IgG expressed in transgenic tobacco plants", Glycobiology, vol. 9 (1999), pp. 365-372.
Charpentier et al., "Analysis of dipeptides in urine by gas chromatography/mass spectometry: implications . . . ", Clinica Chimica Acta, vol. 138 (1984), pp. 299-308.
Chen et al., "Functional antagonism between endogenous mouse growth hormone (GH) and a GH analog results in dwarf transgenic mice", Endocrinolgy, vol. 129 (1991), pp. 1402-1408.
Chen et al., "Glycine 119 of bovine growth hormone is critical for growth-promoting activity", Mol. Endocrinolgy, vol. 5 (1991), pp. 1845-1852.
Chen et al., "In Vitro and in Vivo Studies of Antagonistic Effect of Human Growth Hormone Analogs", The J. of Bio. Chem., vol. 269, No. 22 (1994), pp. 15892-15897.
Chen et al., "Mutations in the third α-helix of bovine growth hormone dramatically affect its . . . ", J. Biol. Chem., vol. 266 (1991), pp. 2252-2258.
Chen et al., "Specific Expression of an Extensin-Like Gene in the Style of *Nicotiana alata*", The Plant Cell, vol. 4 (1992), pp. 1053-1062.
Chen et al., "Conformation studies of biologically active fragments of bovine growth hormone", Biochemistry, vol. 16, No. 10 (1977), pp. 2110-2118.
Chiu et al., "Engineered GFP as a vital reporter in plants", Current Biology, vol. 6, No. 3 (1996), pp. 325-330.
Chou et al., "Prediction of protein conformation", Biochemistry, vol. 13, No. 2 (1974), pp. 222-245.
Churms et al., "Some New Aspects of the Molecular Structure of Acacia senegal Gum (Gum Arabic)", Carbohydrate Research vol. 123 (1983), pp. 267-279.
Clarke et al., "Form and Function of Arabinogalactans and arabinogalactan-Proteins", Phytochem., vol. 18 (1979), pp. 521-540.
Colbere-Garapin et al., "A New Dominant Hybrid Selective Market for Higher Eukaryotic Calls", J. Mol. Biol., vol. 150 (1981), pp. 1-14.
Connolly et al., "Effect of a Proteinase on the Macromolecular Distrubution of Acacia senegal Gum", Carbohydrate Polymers, vol. 8 (1998), pp. 23-32.
Crimmins et al., "Increasing the Sensitivity of 6-Aminoquinolyl-N-hydroxysuccinimidyl Carbamate Amino Acid Analysis . . . ", Analytical Biochemistry, vol. 244 (1997), pp. 407-410.
Cunningham et al., "Engineering human prolactin to bind the human growth hormone receptor", Science, vol. 247 (1990), pp. 1461-1465.
Cunningham et al., "High resolution epitope mapping of hGH-receptor interactions by alanine-scanning mutagenesis", Science, vol. 284, No. 4908 (1989), pp. 1081-1085.
Cunningham et al., "Receptor and antidoby epitopes in human grwoth hormone identified by homolog-scanning mutagenesis", Science, vol. 243, No. 4896 (1989), pp. 1330-1336.
De Blank et al., "Characterization of the soybean early nodulin cDNA clone GmENOD55", Plant Mol. Biol., vol. 22 (1993), pp. 1167-1171.
De Carvalho et al., "Suppression of β-1,3-glucanase transgene expression in homozygous plants", The EMBO J., vol. 11 (1992), pp. 2595-2602.
De Kock et al., "Administration of bovine, porcine and equine growth hormone to the horse . . . ", J. Endocrinol., vol. 171, No. 1 (2001), pp. 163-171.
De Vos et al., "Human Growth Hormone and Extracellular Domain of its Receptor: Crystal Structure of the Complex", Science, vol. 255 (1992), pp. 306-312.
Defaye et al., "Structural Studies of Gum Arabic, the Exudate Polysaccharide from *Acacia senegal*", Carbohydrate Research, vol. 150 (1986), pp. 221-231.

Du et al., "Isolation of the Protein Backbone of an Arabinogalactan-Protein from the Styles of *Nicotiana alata* and . . . ", Plant Cell, vol. 6 (1994), pp. 1643-1653.
Dziezak, "A focus on gums", Food Technology, (Mar. 1991), pp. 116-132.
Evans et al., "The extensin gene family in oilseed rape (*Brassica napus* L.): characterisation of sequences . . . ", Mol Gen Genet., vol. 223, No. 2 (Sep. 1990), pp. 273-287.
Forreiter, et al., "Stable transformation of an Arabidopsis cell suspension culture with firefly luciferase . . . ", Plant Cell, vol. 9, No. 12 (1997), pp. 2171-2181.
Forsyth, "Comparative aspects of placental lactogens: structure and function", Exp. Clin. Endocrinol. vol. 102, No. 3 (1994), pp. 244-251.
Fraley et al., "Liposome-mediated delivery tobacco mosaic virus RNA into tobacco protoplasts . . . ", Proc. Natl. Acad. Sci. USA, vol. 79 (1982), pp. 1859-1863.
Freemark et al., "Purification of a distinct platental lactogen receptor, a new member of the growth hormone/prolactin . . . ", J. Clin. Investig., vol. 83 (1989), pp. 883-889.
Fuh et al., "Prolactin receptor antagonists that inhibit the growth of breast cancer cell lines", J. Biol. Chem., vol. 270, No. 22 (1995), pp. 13133-13137.
Gardiner et al., "Inovlvement of the Golgi Apparatus in the Synthesis and Secretion of Hydroxyproline-rich Cell Wall Glycoproteins", Plant Physiol., vol. 5 (1975), pp. 536-541.
Gastinel, "Galactosyltransferases: A Structural Overview of Their Funtion and . . . ", Trends in Clycoscience and Glycotechnology, vol. 13, No. 70 (2001), pp. 131-145.
Gerken et al., "Determination of the Site-Specific O-Glycosylation Pattern of the Procine Submaxillary mucin Tandem Repeat . . . ", J. Bio. Chem., vol. 272 (1997), pp. 9709-9719.
Gill et al., "Recombinant Chicken and Bovine Growth Hormones Accelerate Growth in Aquacultured Juvenile Pacific Salmon . . . ", Biotechnology, vol. 3 (1985), pp. 643-646.
Goffin et al., "Sequence-Function Relationships Within the Expanding Famliy of Prolactin, Growth Hormone, . . . ", Endocrine Revs., vol. 17, No. 4 (1986), pp. 385-410.
Goodenough et al., "Crystals of the *Chlamydomonas reinhardtii* Cell Wall: Polymerization, Depolymerization, and Purification . . . ", J. Cell. Biol., vol. 103 (1986), pp. 405-417.
Goodrum et al., "Gum arabic glycoprotein contains glycomodules of both extensisn and arabinogalactan-glycoprotiens", Phytochemistry, vol. 54 (2000), pp. 99-106.
Griesbach, "Incorporation of the GUS Gene into Orchids via Embryo Electrophoresis", HortScience, vol. 27 (1992), pp. 620.
Griesbach, et al., "Incorporation of the GUS Gene into Orchids through Embryo Electrophoresis", ISHS Acta Horticulturae 336: II Int'l Symp. on in Vitro Culture . . . (1993).
Guilley et al., "Nucleotide Sequence of Cucurbit Aphid-Borne Yellows Luteovirus", Virology, vol. 202, No. 2 (1994), pp. 1012-1017.
Gunther et al., "UDP-L-arabinose-hydroxyproline-O-glycosyltransferases in *Volvox carteri*", FEBS, vol. 221, No. 2 (1987), pp. 293-298.
Haseloff et al., "Removal of a cryptic intron and subcellular localization of green fluorescent protein are . . . ", Proc. Natl. Acad. Sci., vol. 94 (1997), pp. 2122-2127.
Hirsinger et al., "Characterization of a tobacco extensin gene and regulation of its gene family in healthy . . . ", Plant Mol. Biol., vol. 33, No. 2 (Jan. 1997), pp. 279-289.
Holsters et al., "Transfection and Transformation of *Agrobacterium tumefaciens*", Molec. Gen. Genet., vol. 163 (1978), pp. 181-187.
Horsch et al., "A simple and General Method for Transferring Genes into Plants", Science, vol. 227 (1985), pp. 1229-1231.
Idris et al., "Characterisation of gum from *Acacia senegal* trees of different age and location using . . . ", Food Hydrocolloids, vol. 12 (1998), pp. 379-388.
Islam et al., "A review of recent developments on the regulatory, structural and funcitonal aspects of gum arabic", Food Hydrocolloids, vol. 11 (1997), pp. 493-505.
Keeler et al., "The Tertiary Structure and Bakcbone Dynamics of Human Prolactin", J. Molec. Biol., vol. 328 (2003), pp. 1105-1221.

(56) References Cited

OTHER PUBLICATIONS

Kieliszewski et al., "Extensin: repetitive motifs, function sites, post-translational codes, and phylogeny", The Plant Journal, vol. 5, No. 2 (1994), pp. 157-172.
Kieliszewski et al., "Cross-reactivities of polyclonal antibodies against extensin precursors determined via ELISA techniques", Phytochem., vol. 25, No. 3 (1986), pp. 673-677.
Kieliszewski et al., "A Repetitive Prolin-Rich Protein from the Gymnosperm Douglas Fir Is a Hydroxyproline-Rich Glycoprotein", Plant Physiol, vol. 98 (1992), pp. 919-926.
Kieliszewski et al., "Tandem mass spectrometry and structural elucidation of glycopeptidases . . . ", J. Biol. Chem., vol. 270, No. 6 (1995), pp. 2541-2549.
Kieliszewski et al., "Gum arabic glycoprotein: a new model", FASEB, vol. 11, No. 9 (1997), Abastract #3286.
Kieliszewski et al., "A Histidine-Rich Extensin from *Zea mays* is an Arabinogalactan Protein", Plant Physiology, vol. 9 (1992), pp. 538-547.
Kieliszewski et al., "Potato lectin: modular protein sharing sequence similarities with the extensisn family, . . . ", The Plant Journal, vol. 5, No. 6 (1994), pp. 849-861.
Kieliszewski et al., "Synthetic Genes for the Elucidation of Glycosylation Codes of Hydroxyproline-Rich Glycoproteins", Cell & Mol. Life Sci., vol. 58 (2001), pp. 1386-1398.
Kieliszewski et al., "Structure of the Threonine-Rich Extensin from *Zea mays*", Plant Physiology, vol. 92 (1990), pp. 316-326.
Kivirikko et al., "A colorimetric Method for Determination of Hydroxyproline in Tissue Hydrolysates", Scand J. Clin. Lab. Invest., vol. 11 (1959), pp. 128-131.
Klee et al., "Agrobacterium-mediated plant trasnforrnation and its further applications to plant biology", Ann. Rev. Plant Phys., vol. 38 (1987), pp. 467-486.
Kopchick et al., "Growth Hormone Receptor Antagonists: Discovery, Development, and Use in Patients with Acromegaly", Endocrime Reviews, vol. 23, No. 5 (2002), pp. 623-646.
Krens et al., "In vitro transformation of plant protoplasts with Ti-plasmid DNA", Nature, vol. 296 (1982), pp. 72-74.
Lamport, "Hydroxyproline-O-glycosidic Linkage of the Plant Cell Wall Glycoprotein Extensin", Nature, vol. 216 (1967), pp. 1322-1324.
Lamport et al., "Galactosylserine in Extensin", Biochem. J., vol. 133 (1973), pp. 125-131.
Lamport et al., "Hydroxyproline Arabinosides in the Plant Kingdom", Plant Physiology, vol. 48 (1971), pp. 454-456.
Leonard et al., "Two novel types of O-glycans on the mugwort pollen allergen Art v 1 and their role . . . ", JBC Papers in Press, Published Dec. 10, 2004 as Manuscript M410407200.
Leung et al., "Growth Hormone receptor and serum binding protein: purification, cloning and expression", Nature, vol. 330, No. 6148 (1987), pp. 537-543.
Lewis et al., "Expression and Purification of a protein: A new Strategy for Producing Repetitive Proteins", Protein Express. Purif, vol. 7 (1996), pp. 400-406.
Li et al., "A Chenopod Extensisn Lacks Repetitive Tetrahydroxyproline Blocks", Plant Physiol, vol. 92 (1990), pp. 327-333.
Li et al., "Cloning and developmental/stress-regulated expression of a gene encoding a tomato arabinogalactan protein", Plant Mol. Biol., vol. 32, No. 4 (1996), pp. 641-652.
Li et al., "Purification and characterization of four β-expansisns (*Zea m* 1 isoforms) from maize pollen", Plant Physiol., vol. 132, No. 4 (2003), pp. 2073-2085.
Liu et al., "Epidsodic Evoluation of Growth Hormone in Primates and Emergence of the Species Specificity of . . . ", Mol. Biology & Evolution, vol. 18, No. 6. (2001), pp. 945-953.
Mann et al., "The amino acid sequence of a type I copper protein with an unusual serine- and hydroxyproline-rich . . . ", FEBS, vol. 314, No. 3 (1992), pp. 220-223.

Marusina et al., "Novel peptide-binding proteins and peptide transport in normal and TAP-deficient microsomes", Biochemistry, vol. 36, No. 4 (Jan. 1997), pp. 856-863.
McCormick et al., "Leaf disc transformation of cultivated tomato (*L. esculentum*) using *Agrobacterium tumefaciens*", Plant Cell Reports, vol. 5 (1986), pp. 81-84.
McGrath et al., "Chemical and Biosynthetic Approaches to the Production of Novel Polypeptide Materials", Biotechnol. Prog., vol. 6 (1990), pp. 188-192.
Menassa et al., "A Self-contained system for the field production of plant recombinant interleukin-10", Molecular Biology, vol. 8 (2001), pp. 177-185.
Memelink et al., "Structure and regulation of tobacco extensin", The Plant Journal, vol. 4, No. 6 (1993), pp. 1011-1022.
Merlke et al., " Carbohydrate Composition Analysis of Glycoconjugates by . . . ", in Methods in Enzymology (Lennarz & Hart, Ed., Academic Press, NY, 1994), vol. 230, pp. 1-15.
Miller et al., "Hydroxyproline Heterooligosaccharides in Chlamydomonas", Science, vol. 176 (1972), pp. 918-920.
Miller et al., "Molecular cloning of DNA complementary to bovine growth hormone mRNA", J. Biol. Chem., vol. 255 (1980), pp. 7521-7524.
Mollard et al., "*Acacia senegal* cells cultured in suspension secrete a hydroxyproline-deficint rabinogalactan-protein", Plant Physiol. Biochem., vol. 32 (1994), pp. 703-709.
Nan et al., "Genetic Transformation in Dendrobium . . . ", Biotech. in Agri. and Forest., (Y.P.S. Bajaj, Ed., Springer-Verlag, Berling, Heidelberg, 1995), vol. 34, pp. 145-155.
Napoli et al., "Introduction of a Chimeric Chalcone Synthase Gene into Petunia Results in Reversible Co-Suppression of . . . ", The Plant Cell, vol. 2 (1990), pp. 279-289.
Nicoll et al., "Structural Features of Prolactins and Growth Hormones that Can Be related to Their Biological Properties", Endocrine Revs., vol. 7, No. 2 (1986), pp. 169-203.
Nothnagel, "Proteoglycans and Related Components in Plant Cells", International Review of Cytology, vol. 174 (1997), pp. 195-291.
Osmann et al., "Characterization of Gum Arabic Fractions Obtained by Anion-Exchange Chromatography", Phytochemistry, vol. 38 (1995), pp. 409-417.
Pagny et al., "Structural requirements for *Arabidopsis* β1, 2-xylosyltransferase activity and targeting to the Golgi", The Plant Journal, vol. 33 (2003), pp. 189-203.
Pearce et al., "Emulsifying Properties of Proteins: Evaluation of a Turbidimetric Technique", J. Agric. Food Chem., vol. 26, No. 3 (1978), pp. 716-723.
Pope, "Relationships between Hydroxyproline-containing Proteins Secreted into the Cell Wall and Medium by . . . ", Plant Physiology, vol. 59 (1977), pp. 894-900.
Prakash, et al., "The effects of added proteins on the functionality of gum arabic in soft drink emulsion systems" Food Hydrocolloids, vol. 4, No. 3 (1990), pp. 177-184.
Qi et al., "Gum Arabic Clycoprotein Is a Twisted Hairy Rope", Plant Physiol., vol. 96 (1991), pp. 848-855.
Raz et al., "The sequence of a hydroxyproline-rich glycoprotein gene from *Sorghum vulgare*", Plant Molecular Biology, vol. 16 (1991), pp. 365-367.
Rhodes et al., "Transformation of Maize by Electroporation of Embryos," Methods Mol. Biol., vol. 55 (1995), pp. 121-131.
Ross et al., "Binding and functional studies with the growth hormone receptor antagonist, B2036-PEG . . . ", J. Clin. Endo. Metab., vol. 86, No. 4 (2001), pp. 1716-1723.
Sambrook et al., Moleculare Cloning Laboratory Manual, (ROE, Ed., Cold Spring Harbor Laboratory Press, NY, 1989), pp. 13.7-13.9 and 16.33-16.36.
Schenk et al., "Medium and Techniques for Induction and Growth of *Monocotyledonous* and *Dicotyledonous* Plant Cell Cultures", Can. J. Bot., vol. 50 (1972), pp. 199-204.
Schnabelrauch et al., "Isolation of pl4.6 extensisn peroxidase from tomato cell suspension . . . ", The Plant J., vol. 9, No. 4 (1996), pp. 477-489.
Service, "Unnatural Amino Acid Could Prove Boon for Protein Therapeutics", Science, vol. 308 (2005), p. 44.

(56) References Cited

OTHER PUBLICATIONS

Shaper et al., "The Galactosyltransferases", in Carbohydrates in Chemistry and Biology, (ERNST, Ed., Weinheim, NY, 2000), vol. 3, Ch. 10, pp. 175-196.
Sheikholeslam et al., "Acetosyringone promotes high efficiency transformation of *Arabidopsis thaliana* explants by . . . ", Plan Mol. Biol., vol. 8 (1987), pp. 291-298.
Shirsat et al., "Expression of a *Brassica napus* extensin gene in the vascular system of transgenic . . . ", Plant Mol. Biol. vol. 17, No. 4 (Oct. 1991), pp. 701-709.
Shpak et al., "Contiguous Hydroxyproline Residues Direct Hydroxyproline Arabinosylation in *Nicotiana tabacum*", The J. of Bio. Chem., vol. 276, No. 14 (2001), pp. 11272-11276.
Shpak et al., "Synthetic Genes for glycoprotein design and the eludication of hydroxyproline-O-glycosylation codes", Proc. Natl. Aca. Sci., vol. 96 (1999), pp. 14736-14741.
Smith et al., "Tomato Extensisn Precursors P1 and P2 are highly periodic structures", Phytochem., vol. 25, No. 5 (1986), pp. 1021-1030.
Sommer-Knudsen et al., "Hydroxyproline-rich plant glycoproteins", Phytochemistry, vol. 47 (1998), pp. 483-497.
Stephen et al., "Exudate Gums", Methods Plant Biochem., vol. 2 (1990), pp. 483-522.
Sticher et al., "Posttranslational Processing of a New Class of Hydroxyproline-Containing Proteins", Plant Physiol., vol. 101 (1993), pp. 1239-1247.
Sticher et al., "Vacuolar Chitinases of Tobacco: A new Class of Hydroxyproline-Containing Proteins", Science, vol. 257, No. 5070j (1992), pp. 665-657.
Stiefel et al., "Molecular cloning of cDNAs encoding a putative cell wall protein from *Zea mays* and immunological . . . ", Plant Mol. Bio., vol. 11 (1988), pp. 483-493.
Strahl-Bolsinger et al., "Protein O-mannosylation", Biochimica et Biophysica Acta, vol. 1426 (1999), pp. 297-307.
Stryer, Biochemistry, W.H. Freeman & Co., San Francisco, CA, (1975), pp. 6-17 and 208-209.
Takahashi et al., "Brief report: Short stature caused by a mutant growth hormone", New England Journal of Medicine, vol. 334, No. 7 (1996), pp. 432-436.
Tan, "O-Glycosylation Motifs in Arabinogalactan-Proteins", Dotoral Dissertation, Ohio University, presented Jun. 2003.
Tan, et al., "Glycosylation Motifs that direct arabingogalactan addition to arabinogalactan-proteins", Plant Physiol., vol. 132 (2003), pp. 1362-1369.
Tan, et al., "Structure of a hydroxyproline (Hyp)-arabinogalactan polysaccharide from repetitive Ala-Hyp . . .", J. Bio. Chem., vol. 279, No. 13 (Mar. 26, 2004), pp. 13156-13165.
Tsien, "The Green Fluroescent Protein", Annu. Rev. Biochem., vol. 67 (1998), pp. 509-544.
Van Wandelen, et al., "Using quatemary high-performance liquid chromatography eluent systems for separating . . . ", J. Chromatography A, vol. 763 (1997), pp. 11-22.
Watanabe et al., "Cloning and expression of two genes encoding auxin-binding proteins from tobacco", PMB, vol. 36 (1998), pp. 63-74.
Watahiki et al., "Conserved and unique amino acid residues in the domains of the growth hormones . . . ", J. Bio. Chem., vol. 264 (1989), pp. 312-316.
Wells et al., "Structure and Function of Human Growth Hormone: Implications for the Hematopoietins", Ann. Rev. Biophys. Biomol. Struct., vol. 22 (1993), pp. 329-351.
Wigler, et al., "Transformation of mammalian cells with an amplifiable dominant-acting gene", Pro. Nai. Acad. Sci, vol. 7 (1980), pp. 3567-3570.
Woessner et al., "Domain conservation in several volvocalean cell wall proteins", Plant Mol. Bio., vol. 26 (1994), pp. 947-960.
Xu, et al., "Production of recombinant plant gum with tobacco cell . . . ", Biotech. Bioeng., vol. 90, No. 5 (Jun. 5, 2005), pp. 578-588.
York, et al., "Isolation and Characterization of Plant Cell Walls and Cell Wall Components", Methods in Enzymology, vol. 118 (1985), pp. 3-40.
Zhang et al., "Expression of an environmentally friendly synthetic protein-based polymer gene in transgenic tobacco plants", Plant Cell Reports, vol. 16 (1996); pp. 174-179.
Zhao et al., "Tomato LeAGP-1 arabinogalactan-protein pruified from transgenic tobacco corroborates the Hyp contiguity hypothesis", Plant J., vol. 31, No. 4 (2002), pp. 431-44.
Zhou et al., "Molecular cloning of a human UDP-galactose:GlcNAcβ1, 3GalNAcβ1, 3 galactosyltransferase . . . ", Eur. J. Biochem., vol. 263 (1999), pp. 571-576.
Akiyama et al., "Gum Arabic is a Kind of Arabinogalactan-Protein", Agric. Biol. Chem., vol. 48 (1984), pp. 235-237.
Alexandrou et al., "Inhibition of Anglotensisn Converting Enzyme by L-ALANYL-4 or 5 Substituted-L-Prolines . . . ", Biochem. Intl, vol. 21, No. 1 (1990), pp. 271-278.
Allan et al., "Identification of novel sites in the ovine growth hormone receptor involved in binding hormone . . . ", Eur. J. Biochem., vol. 261, No. 2 (1999), pp. 555-561.
De Loose et al., "The extensin signal peptide allows secretion of a heterologous protein from protoplasts", Gene, vol. 99 (1991), pp. 95-100.
Delonnay, "Determination of the Protein Constitutent of Gum Arabic", Master of Science Thesis, (1993) (76 pages).
Schnabelrauch et al., "Isolation of pI4.6 extensisn peroxidase from tomato cell suspension cultures and identification of Val-Tyr-Lys as putative intermolecular cross-link site", The Plant J., (1996), vol. 9, No. 4, pp. 477-489.
Service, "Unnatural Amino Acid Could Prove Boon for Protein Therapeutics", Science, (2005), vol. 308, pp. 44.
Shaper et al., "The Galactosyltransferases", in Carbohydrates in Chemistry and Biology, (Ernst, Ed., Weinheim NY, 2000), vol. 3, Ch. 10, pp. 175-196.
Sheikholeslam et al., "Acetosyringone promotes high efficiency transformation of *Arabidopsis thaliana* explants by *Agrobacterium tumefaciens*", Plant Molec. Biol., (1987), vol. 8, pp. 291-298.
Shirsat et al., "Expression of a *Brassica napus* extensin gene in the vascular system of transgenic tobacco and rape plants", Plant Mol Biol. (Oct. 1991), vol. 17, No. 4, pp. 701-709.
Shimizu et al., "Experimental determination of proline hydroxylation and hydroxyproline araginoglactosylation motifs in secretory proteins," The Plant Journal, (2005), vol. 42, pp. 877-889.
Shpak et al., "Contiguous Hydroxyproline Residues Direct Hydroxyproline Arabinosylation in Nicotiana tabacum", The Journal of Biological Chemistry, (2001), vol. 276, No. 14, pp. 11272-11276.
Shpak et al., "Synthetic Genes for glycoprotein design and the eludication of hydroxyproline-O-glycosylation codes", Proc. Natl. Aca. Sci., (1999), vol. 96, pp. 14736-14741.
Smith et al., "Tomato Extensisn Precursors P1 and P2 are highly periodic structures", Phytochem., (1986), vol. 25, No. 5, pp. 1021-1030.
Sommer-Knudsen at al., "Hydroxyproline-rich plant glycoproteins", Phytochemistry (1998), vol. 47, pp. 483-497.
Stephen at al., "Exudate Gums", Methods Plant Biochem., (1990), vol. 2, pp. 483-522.
Sticher et al., "Posttranslational Processing of a New Class of Hydroxyproline-Containing Proteins", Plant Physiol., (1993), vol. 101, pp. 1239-1247.
Sticher et al., "Vacuolar Chitinases of Tobacco: A new Class of Hydroxyproline-Containing Proteins", Science, (1992), vol. 257, No. 5070j, pp. 665-657.
Stiefel et al., "Molecular cloning of cDNAs encoding a putative cell wall protein from *Zea mays* and immunological identification of related polypeptides", Plant Molecular Biology, (1988), vol. 11, pp. 483-493.
Strahl-Bolsinger et al., "Protein O-mannosylation", Biochimica et Biophysica Acta, (1999), vol. 1426, pp. 297-307.
Stryer, Biochemistry, W.H. Freeman & Co., San Francisco, CA, (1975), pp. 16-17, 208-209.
Takahashi et al., "Brief report: Short stature caused by a mutant growth hormone", New England Journal of Medicine, (1996), vol. 334, No. 7, pp. 432-436.

(56) References Cited

OTHER PUBLICATIONS

Tan, et al., "Glycosylation Motifs that direct arabingogalactan addition to arabinogalactan-proteins", Plant Physiol., (2003), vol. 132, pp. 1362-1369.
Tan, et al., "Structure of a hydroxyproline (Hyp)-arabinogalactan polysaccharide from repetitive Ala-Hyp expressed in transgenic *Nicotiana tabacum*", J. Biol. Chem, (Mar. 26, 2004), vol. 279, No. 13 pp. 13156-13165.
Tsien, "The Green Fluroescent Protein", Annu. Rev. Biochem., (1998), vol. 67, pp. 509-544.
Van Wandelen, et al., "Using quaternary high-performance liquid chromatography eluent systems for separating 6-aminoquinolyl-N-hydroxysuccinimidyl carbamate-derivatized amino acid mixtures", J. Chromatography A, (1997), vol. 763, pp. 11-22.
Watahiki et al., "Conserved and unique amino acid residues in the domains of the growth hormones. Flounder growth hormone deduced from the cDNA sequence has the minimal size in the growth hormone prolactin gene family", J. Biol. Chem. (1989), vol. 264, pp. 312-316.
Watanabe et al., "Cloning and expression of two genes encoding auxin-binding proteins from tobacco", PMB, (1998), vol. 36, pp. 63-74.
Wells et al., "Structure and Function of Human Growth Hormone: Implications for the Hematopoietins", Ann. Rev. Biophys. Biomol. Struct., (1993), vol. 22, pp. 329-351.
Wigler, et al., "Transformation of mammalian cells with an amplifiable dominant-acting gene", Pro. Nai. Acad. Sci, (1980), vol. 7, pp. 3567-3570.
Wileman, Thomas E., "Properties of asparaginase-dextran conjugates". Adv. Drug Delivery Revs., (1991), vol. 6, pp. 167-180.
Woessner et al., "Domain conservation in several volvocalean cell wall proteins", Plant Molec. Biol., (1994), vol. 26, pp. 947-960.
Xu, et al., "Production of recombinant plant gum with tobacco cell culture in bioreactor and gum characterization", Biotechnol Bioeng., (Jun. 5, 2005), vol. 90, No. 5, pp. 578-588.
York, et al., "Isolation and Characterization of Plant Cell Walls and Cell Wall Components", Methods in Enzymology, (1985), vol. 118, p. 3.
Zhang et al., "Expression of an environmentally friendly synthetic protein-based polymer gene in transgenic tobacco plants", Plant Cell Reports, (1996), vol. 16, pp. 174-179.
Zhang et al., "Expression of Eukaryotic Proteins in Soluble Form in *Escherichia coli*", Protein Expression and Purification, (1998), vol. 12, No. 2, pp. 159-165.
Zhao et al., "Tomato LeAGP-1 arabinogalactan-protein pruified from transgenic tobacco corroborates the Hyp contiguity hypothesis", Plant J., (2002), vol. 31, No. 4, pp. 431-444.
Zhou et al., "Molecular cloning of a human UDP-galactose:GlcNAcBETA1, 3GaINAcBETA1, 3 galactosyltransferase gene enciding an O-linked core3-elongation enzyme", Eur. J. Biochem., (1999), vol. 263, pp. 571-576.
Issue Notification in U.S. Appl. No. 10/418,032, dated May 27, 2008 (1 page).
Notice of Allowance in U.S. Appl. No. 10/418,032, dated Mar. 17, 2008 (7 pages).
Notice of Allowance in U.S. Appl. No. 10/418,032, dated Feb. 13, 2008 (1 page).
Notice of Allowance in U.S. Appl. No. 10/418,032, dated Nov. 11, 2007 (6 pages).
Office Action in U.S. Appl. No. 10/437,708, dated May 9, 2008 (7 pages).
Advisory Action in U.S. Appl. No. 10/437,708, dated Feb. 1, 2008 (3 pages).
Office Action in U.S. Appl. No. 10/437,708, dated Nov. 8, 2007 (7 pages).
Notice of Allowance in U.S. Appl. No. 11/173,811, dated Oct. 8, 2010 (7 pages).
Office Action in U.S. Appl. No. 11/173,811, dated May 12, 2008 (16 pages).
Office Action in U.S. Appl. No. 11/173,811, dated Dec. 27, 2007 (13 pages).
Notice of Allowance in U.S. Appl. No. 11/243,295, dated Apr. 23, 2008 (7 pages).
Office Action in U.S. Appl. No. 11/243,295, dated Oct. 10, 2008 (6 pages).
Office Action in U.S. Appl. No. 11/243,295, dated Jan. 3, 2008 (8 pages).
Office Action in U.S. Appl. No. 11/036,257, dated Nov. 8, 2011 (7 pages).
Office Action in U.S. Appl. No. 11/036,256, dated Dec. 17, 2007 (21 pages).
Office Action in U.S. Appl. No. 11/036,256, dated Jul. 5, 2007 (10 pages).
International Search Report in PCT/US07/73137, dated Sep. 18, 2008 (5 pages).
Written Opinion in PCT/US07/73137, dated Sep. 18, 2008 (4 pages).
International Search Report in PCT/US06/26594, dated Jul. 31, 2008 (4 pages).
Written Opinion in PCT/US06/26594, dated Jul. 31, 2008 (4 pages).
International Search Report in PCT/US05/13252, mailed Oct. 2, 2006 (3 pages).
International Preliminary Examination Report in PCT/US98/15083, mailed May 17, 1999 (4 pages).
Supplemental European Search Report in EP04759826.3, dated Dec. 27, 2007 (6 pages).
Supplemental European Search Report in EP05726258.6, dated Jan. 25, 2008 (9 pages).
Supplementary European Search Report in EP05779913, dated Jun. 6, 2008 (3 pages).
Examination Report in EP04759826.3, dated Jun. 9, 2008 (6 pages).
Examination Report in EP05726258.6, dated Jun. 11, 2008 (8 pages).
Office Action in JP2000-503184, mailed Feb. 19, 2008 (4 pages; English translation).
Office Action in CA 2,296,813, dated Mar. 4, 2008 (1 page).
Examination Report in NZ 548,513, dated Mar. 10, 2008 (2 pages).
Akiyama et al., "Gum Arabic is a Kind of Arabinogalactan-Protein", Agric. Biol. Chem., (1984) vol. 48, pp. 235-237.
Alexandrou et al., "Inhibition of Anglotensisn Converting Enzyme by L-ALANYL-4 or 5 Substituted-L-Prolines and Their N-Phosphoryl-Derivatives", Biochemicstry International, (1990), vol. 21, No. 1, pp. 271-278.
Allan et al., "Identification of novel sites in the ovine growth hormone receptor involved in binding hormone and conferring species specificity", Eur. J. Biochem., (1999), vol. 261, No. 2, pp. 555-561.
De Loose et al., "The extensin signal peptide allows secretion of a heterologous protein from protoplasts", Gene, (1991), vol. 99, pp. 95-100.
Delonnay, "Determination of the Protein Constitutent of Gum Arabic", Master of Science Thesis, (1993).
Fong et al., "A Gymnosperm Extensin Contains the Serine-Tetrahydroxyproline Motif", Plant Physiology, (1992), vol. 99, No. 2, pp. 548-552.
Ivan et al., "Biochemical purification and pharmacological inhibition of a mammalian prolyl hydroxylase acting on hypoxia-inducible factor," PNAS (2002), vol. 99, pp. 13459-13464.
Lamport et al., "Hydroxyproline in Primary Cell Walls of Higer Plants", Nature, (1960), vol. 188, pp. 665-666.
Lewis et al., "Structure and Properties of Members of the High Family: A Review", Endocrine Journal, (2000), vol. 47, No. Suppl., pp. S1-S8.
Ma, et al., "The production of recombinant pharmaceutical proteins in plants", Nature Reviews Genetics, (2003) vol. 4, No. 10, pp. 153-157.
Nacka et al., "Induction of new physicochemical and functional properties by the glycosylation of whey proteins", Journal of Protein Chemistry, (1998), vol. 17, No. 5, pp. 495-503.
Prakash, et al., "The effects of added proteins on the functionality of gum arabic in soft drink emulsion systems" Food Hydrocolloids, (1990), vol. 4, No. 3, pp. 177-184.
Putney at al., "Improving Protein Therapeutics with Sustained-Release Formulations", Nature Biotechnology, (1998), vol. 16, pp. 153-157.
Qi et al., "Gum Arabic Glycoprotein is a Twisted Hairy Rope", Plant Physiol., (1991), vol. 96, pp. 848-855.

(56) References Cited

OTHER PUBLICATIONS

Raz et al., "The sequence of a hydroxyproline-rich glycoprotein gene from *Sorghum vulgare*", Plant Molecular Biology, (1991), vol. 16, pp. 365-367.
Rhodes et al., "Transformation of Maize by Electroporation of Embryos," Methods Mol Biol (1995), vol. 55, pp. 121-131.
Ross et al., "Binding and functional studies with the growth hormone receptor antagonist, B2036-PEG (pegvisomant), reveal effects of pegylation and evidence that it binds to a receptor dimer", J Clin Endocrinol Metab, (2001), vol. 86, No. 4, pp. 1716-1723.
Sambrook et al., Molecular Cloning Laboratory Manual, (Roe, Ed., Cold Spring Harbor Laboratory Press, NY, 1989), pp. 13.7-13.9 and 16.33-16.36.
Schenk et al., "Medium and Techniques for Induction and Growth of *Monocotyledonous* and *Dicotyledonous* Plant Cell Cultures", Can. J. Bot., (1972), vol. 50, pp. 199-204.
Ayres, Martin D. et al., "The Complete DNA Sequence of *Autographa californica* Nuclear Polyhedrosis Virus," Virology (1994), vol. 202, pp. 586-605.
Berra et al., "The hypoxia-inducible-factor hydroxylases bring fresh air into hypoxia signalling," EMBO Reports, vol. 7, No. 1, pp. 41-45 (2006).
Kieliszewski et al., "Synthetic Genes for the Elucidation of Glycosylation Codes of Hydroxyproline-Rich Glycoproteins," Abstract published/presented at the XVI International Botanical Congress, St. Louis, MO, Jul. 31, to Aug. 3, 1999.
Merle et al., Hydroxylated human homotrimeric collagen I in *Agrobacterium tumefaciens*-mediated transient expression and in transgenic tobacco plant, FEBS letters 515 (2002) pp. 114-115.
Perlman et al., "Glycosylation of an N-Terminal extension prolongs the half-life and increases the in vivo activity of follicle stimulating hormone," J. Clin. Endocrinol. Metab., 2003, 88: 3227-3235.
Sundstrom et al., Crystal Structure of an Antagonist Mutant of Human Growth Hormone, G12OR, in Complex with it's receptor at 2.9 A Resolution: J. Biol. Chem., 271, 32197-32203 (1996).
Office Action in U.S. Appl. No. 10/437,708 mailed Mar. 9, 2009 (7 pages).
Office Action in U.S. Appl. No. 10/437,708 mailed Dec. 16, 2009 (11 pages).
Notice of Allowance in U.S. Appl. No. 11/173,811 mailed Mar. 6, 2009 (14 pages).
Notice of Allowance in U.S. Appl. No. 11/173,811 mailed Aug. 14, 2009 (7 pages).
Notice of Allowance in U.S. Appl. No. 11/243,295 mailed May 1, 2009 (12 pages).
Notice of Allowance in U.S. Appl. No. 11/243,295 mailed Sep. 10, 2009 (10 pages).
Office Action in U.S. Appl. No. 11/995,603, mailed Dec. 16, 2009 (5 pages).
Office Action in U.S. Appl. No. 11/995,603, mailed Jul. 6, 2010 (10 pages).
Office Action in U.S. Appl. No. 12/117,692, mailed Jan. 26, 2010 (10 pages).
Office Action in U.S. Appl. No. 12/117,692, mailed Jul. 13, 2010 (7 pages).
Office Action in U.S. Appl. No. 12/121,140 mailed Dec. 22, 2009 (9 pages).
Office Action in U.S. Appl. No. 12/121,140 mailed Aug. 13, 2009 (5 pages).
Office Action in U.S. Appl. No. 12/122,606 mailed Jan. 26, 2010 (9 pages).
Office Action in U.S. Appl. No. 12/122,606 mailed Aug. 5, 2010 (18 pages).
Office Action in U.S. Appl. No. 12/781,490 mailed Dec. 2, 2010 (11 pages).
Office Action in U.S. Appl. No. 12/820,943 mailed Feb. 2, 2011 (5 pages).
PCT/US07/73137—International Preliminary Report on Patentability issued Jan. 13, 2009 (5 pages).
CA 2,296,813—Notice of Allowance, dated Jul. 22, 2009 (1 page).
CN 200580007911.6—Office Action dated Feb. 27, 2009 (with available partial translation).
EP 98 944 431.0—Examination Report, dated Nov. 20, 2008 (5 pages).
EP 05 726 258.6—Examination Report mailed Apr. 20, 2009 (3 pages).
EP 05 726 258.6—Examination Report, mailed Apr. 23, 2010 (4 pages).
EP 05 726 258.6—Examination Report, mailed Aug. 2, 2010 (5 pages).
EP 05 779 913.2—Examination Report, mailed Feb. 27, 2009 (5 pages).
EP 05 779 913.2—Examination Report, mailed Sep. 6, 2010 (5 pages).
EP 07 799 434.1—Extended European Search Report, mailed Dec. 14, 2009 (6 pages).
EP 09 004 742.4—Extended European Search Report, mailed Oct. 27, 2009 (9 pages).
EP 09 004 742.4—Examination Report, mailed Jul. 19, 2010 (5 pages).
IL 176781—Official Action, mailed Jul. 16, 2009 (3 pages) (available translation only).
IL 176781—Official Action, mailed Aug. 19, 2010 (2 pages) (available translation only).
JP 2000-503184—Office Action, mailed Jun. 12, 2009 (4 pages) (no translation available).
JP 2006-549613—Office Action, mailed Aug. 31, 2010 (4 pages) (available translation only).
MX 2006/008126—Office Action, mailed Jan. 26, 2010 (3 pages) (no translation available).
NZ 548.513—Examination Report, mailed Oct. 5, 2009 (2 pages).
NZ 579,586—Examination Report, mailed Sep. 15, 2009 (3 pages).
JP 2001-575817—Office Action, mailed Mar. 2, 2011 (12 pages) (with available translation).
Gao et al., "Isolation, characterization and immunolocalization of a novel, modular tomato arabinogalactan-protein corresponding to the LeAGP-1 gene," The Plant Journal (1999), 18(1), 43-55.
Brady et al., "Di-isodityrosine, a novel tetrameric derivative of tyrosine in plant cell wall proteins: a new potential cross-link," Biochem. J. (1996) 315, 323-327.
Brady et al., "Formation of Di-Isodityrosine and Loss of Isodityrosine in the Cell Walls of Tomato Cell-Suspension Cultures Treated with Fungal Elicitors of H2O2," Plant Physiol. (1997) 115: 87-92.
Rogers, KK, "The Potential of Plant-Made Pharmaceuticals," published online (2003).
Twyman et al., "Transgenic plants in the biopharmaceutical market," Expert Opin. Emerging Drugs (Feb. 2005) 10 (1):185-218.
Office Action in U.S. Appl. No. 12/820,943 mailed Aug. 25, 2011 (9 pages).
Office Action in U.S. Appl. No. 12/820,943 mailed Feb. 22, 2012 (8 pages).
Office Action in U.S. Appl. No. 13/005,715 mailed Mar. 6, 2012 (10 pages).
Office Action in U.S. Appl. No. 13/019,819 mailed Mar. 8, 2012 (20 pages).
AU 2005206885—Notice of Allowance, dated Jan. 13, 2012 (3 pages).
AU 2005206885—Examination Report, dated Apr. 13, 2010 (5 pages).
CA 2,573,918—Office Action, dated Jan. 24, 2012 (3 pages).
CA 2,553,257—Office Action, dated Jan. 12, 2012 (4 pages).
EP 98 944 431.0—Examination Report, dated Aug. 26, 2011 (6 pages).
EP 05 726 258.6—Examination Report, mailed Nov. 25, 2011 (6 pages).
EP 05 779 913.2—Examination Report, mailed Jun. 1, 2012 (4 pages).
EP 09 004 742.4—Examination Report, mailed Nov. 25, 2011 (8 pages).
JP 2006-549613—Office Action, mailed Nov. 21, 2011 (3 pages) (available translation only).

(56) References Cited

OTHER PUBLICATIONS

Fares et al., "Design of a long-acting follitropin agonist by fusing the C-terminal sequence of the chorionic gonadotropin B subunit to the follitropin B subunit," Proc. Natl. Acad. Sci., vol. 89, pp. 4304-4308 (May 1992).
Gleeson et al., "Characterization of the hydroxyproline-rich protein core of an arabinogalactan-protein secreted from suspension-cultured *Lolium muliflorum* (Italian ryegrass) endosperm cells," Biochem. J. (1989) 264, 857-862.
Xu, et al., "High-Yields and Extended Serum Half-Life of Human Interferon alpha2b Expressed in Tobacco Cells as Arabinogalactan-Protein Fusions", Biotechnol Bioeng., (Feb. 27, 2007), vol. 97, No. 5, pp. 997-1008.
Office Action in U.S. Appl. No. 12/820,943 mailed Oct. 15, 2012 (6 pages).
Notice of Allowance in U.S. Appl. No. 12/820,943 mailed May 30, 2013 (8 pages).
Office Action in U.S. Appl. No. 13/005,715 mailed Oct. 3, 2012 (12 pages).
Office Action in U.S. Appl. No. 13/019,819 mailed Nov. 13, 2012 (15 pages).
Office Action in U.S. Appl. No. 13/019,819 mailed Jun. 19, 2013 (15 pages).
Office Action in CA 2,573,918, dated Jan. 25, 2013 (2 pages).
Office Action in CA 2,553,257, dated Mar. 25, 2013 (2 pages).
Examination Report in EP 98 944 431.0, dated Aug. 7, 2012 (4 pages).
Examination Report in EP 98 944 431.0, dated Aug. 28, 2012 (4 pages).
Examination Report in EP 98 944 431.0, dated Apr. 2, 2013 (4 pages).
Summons to Attend Oral Proceedings in EP 05 726 258.6, mailed Nov. 19, 2012 (5 pages).
Notice of Grant in EP 05 726 258.6, mailed Jul. 17, 2013 (5 pages)..
Examination Report in EP 05 779 913.2, mailed Feb. 21, 2013 (3 pages).
Summons to Attend Oral Proceedings in EP 09 004 742.4, mailed Nov. 16, 2012 (6 pages).
Notice of Grant in EP 09 004 742.4, mailed Jul. 25, 2013 (7 pages).
Office Action in IL 176781, mailed Aug. 5, 2013 (6 pages).
Furuhashi et al., "Fusing the Carboxy-Terminal Peptide of the Chorionic Gonadotropin (CG) Beta-Subunit to the Common Alpha-Subunit: Retention of O-Linked Glycosylation and Enhanced In Vivo Bioactivity of Chimeric Human CG," Mol. Endocrinology (1995), vol. 9, No. 1, pp. 54-63.
Office Action in JP 2006-549613, mailed Nov. 28, 2012 (2 pages).
Nishi, Tatsumari., "Qualitative Improvements of Therapeutic Glycoproteins by Glycotechnology", (1992), vol. 4 No. 16, pp. 336-344.
Tsumuraya, Yoichi et al., "Arabinogalactan-Proteins from Primary and Mature Roots of Radish (Raphanus sativus L.)," Plant Physiol. (1988) 86, 0155-0160.
Leonard, Renaud, et al., "Two Novel Types of O-Glycans on the Mugwort Pollen Allergen Art v 1 and Their Role in Antibody Binding," J. Biol. Chem., vol. 280, No. 9, pp. 7932-7940 (2005).
Wilson, Iain BH, "Glycosylation of Proteins in Plants and Invertebrates," Curr Opin Struct Biol. Oct. 2002; 12 (5):569-77.

\* cited by examiner

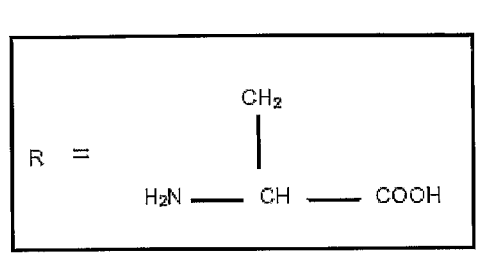 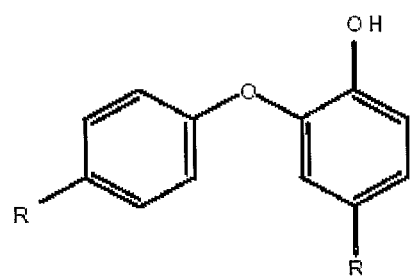
Figure 1

(A) FK oligonucleotide pairs

5' Linker pair (5'SP3-s and 5'SP3-as)
```
         BamHI           XmaI
5'-GCT GCC GGA TCC TCA ACC CGG GCC TCA CCA-3'
3'-CGA CGG CCT AGG AGT TGG GCC CGG AGT GGT GGT GGA-5'
    A   A   G   S   S   T   R   A   S   P
```

FK Internal repeat pair (FK-s and FK-as)
```
5'-CCA CCA CCT AGT CCG TCA CCC CCT CCC CCA TTT TTC TTT AAG AGC CCA
              TCA GGC AGT GGG GGA GGG GGT AAA AAG AAA TTC TCG GGT GGT GGT GGA-5'
    P   P   P   S   P   S   P   P   P   P   F   F   F   K   S   P
```

3'-Linker pair (3'SP4-s and 3'SP4-as)
```
                               NcoI      SacI       EcoRI
5'-CCA CCA CCT TCC ATG GCA TAA TAG AGC TCG AAT TCC TGG CCC ACC-3'
3'-     AGG TAC CGT ATT ATC TCG AGC TTA AGG ACC GGG TGG-5'
    P   P   P   S   M   A   -   -
```

(B) YK oligonucleotide pair

YK-Sense oligonucleotide (YK-ss)
```
        XmaI     BbsI
5'-GGG ACC CGG GGA AGA CGA CCA TCA CCA CCA CCA CCT TAC TAC TAC AAG TCT CCT-3'
    G   T   R   G   R   R   P   S   P   P   P   Y   Y   Y   K   S   P
```

YK-Antisense oligonucleotide (YK-as)
```
                                                NcoI    BsmFI            SacI
3'-GGT GGA ATG ATG ATG TTC AGA GGA GGA GGG GGT AGT GGT AGT TGG TAC CGC AGG GCC ACT ATC CTC GAG TTA-5'
    P   P   Y   Y   Y   K   S   P   P   P   P   S   P   S   T   M   A   S   R   -   -   E   L   N
```

(C) YL oligonucleotide pair

YL-Sense oligonucleotide (YL-ss)
```
        XmaI     BbsI
5'-GGG ACC CGG GGA AGA CGA CCA TCA CCA CCA CCA CCT TAC TAC TAC CTA TCT CCT-3'
    G   T   R   G   R   R   P   S   P   P   P   Y   Y   Y   L   S   P
```

YL-Antisense oligonucleotide (YL-as)
```
                                                NcoI    BsmFI            SacI
3'-GGT GGA ATG ATG ATG GAT AGA GGA GGA GGG GGT AGT GGT AGT TGG TAC CGC AGG GCC ACT ATC CTC GAG TTA-5'
    P   P   Y   Y   Y   L   S   P   P   P   P   S   P   S   T   M   A   S   R   -   -   E   L   N
```

(D) FL oligonucleotide pair

FL-Sense oligonucleotide (FL-ss)
```
        XmaI     BbsI
5'-GGG ACC CGG GGA AGA CGA CCA TCA CCA CCA CCA CCT TTT TTC TTT CTA TCT CCT-3'
    G   T   R   G   R   R   P   S   P   P   P   F   F   F   L   S   P
```

FL-Antisense oligonucleotide (FL-as)
```
                                                NcoI    BsmFI            SacI
3'-GGT GGA AAA AAG AAA GAT AGA GGA GGA GGG GGT AGT GGT AGT TGG TAC CGC AGG GCC ACT ATC CTC GAG TTA-5'
    P   P   F   F   F   L   S   P   P   P   P   S   P   S   T   M   A   S   R   -   -   E   L   N
```

Figure 5

(a) *M13 forward* oligonucleotide primer

5'-GTA AAA CGA CGG CCA GTG-3'

(b) *Tobacco signal sequence (SSeq4Sen)* oligonucleotide primer

5'-CGG CAA TGG GAA AAA TGG CTT CT-3'

(c) *EGFP (EGFP566as)* oligonucleotide primer

5'-GAA GAT GGT GCG CTC CTG GAC GT-3'

BamHI                              SIGNAL SEQUENCE

GGA TCC GCA ATG GGA AAA ATG GCT TCT CTA TTT GCC ACA TTT TTA GTG GTT TTA GTG TCA CTT AGC TTA GCA CAA ACA ACC

G   S   A   M   G   K   M   A   S   L   F   A   T   F   L   V   V   L   V   S   L   S   L   A   Q   T   T

Xmal                               YK                              NcoI      EGFP→

CGG GGA AGA CGA [CCA TCA CCA CCA CCA CCT TAC TAC TAC AAG TCT CCT CCT CCC CCA TCA] CCA TCA ACC ATG GTG AGC AAG...

R   G   R   R  |P   S   P   P   P   P   Y   Y   Y   K   S   P   P   P   P   S|P   S   T   M   V   S   K

8 & 20

B

BamHI                              SIGNAL SEQUENCE

GGA TCC GCA ATG GGA AAA ATG GCT TCT CTA TTT GCC ACA TTT TTA GTG GTT TTA GTG TCA CTT AGC TTA GCA CAA ACA ACC

G   S   A   M   G   K   M   A   S   L   F   A   T   F   L   V   V   L   V   S   L   S   L   A   Q   T   T

Xmal                               YL                              NcoI      EGFP→

CGG GGA AGA CGA [CCA TCA CCA CCA CCA CCT TAC TAC TAC CTA TCT CCT CCT CCC CCA TCA] CCA TCA ACC ATG GTG AGC AAG...

R   G   R   R  |P   S   P   P   P   P   Y   Y   Y   L   S   P   P   P   P   S|P   S   T   M   V   S   K

8 & 20

C

BamHI                              SIGNAL SEQUENCE

GGA TCC GCA ATG GGA AAA ATG GCT TCT CTA TTT GCC ACA TTT TTA GTG GTT TTA GTG TCA CTT AGC TTA GCA CAA ACA ACC

G   S   A   M   G   K   M   A   S   L   F   A   T   F   L   V   V   L   V   S   L   S   L   A   Q   T   T

Xmal                              FK                              NcoI      EGFP→

CGG GCC TCA CCA [CCA CCA CCT AGT CCG TCA CCC CCT CCC CCA TTT TTC TTT AAG AGC CCA] CCA CCA CCT TCC ATG GTG AGC AAG

R   A   S   P  |P   P   P   S   P   S   P   P   P   P   F   F   F   K   S   P|P   P   P   S   M   V   S   K

9

D

BamHI                              SIGNAL SEQUENCE

GGA TCC GCA ATG GGA AAA ATG GCT TCT CTA TTT GCC ACA TTT TTA GTG GTT TTA GTG TCA CTT AGC TTA GCA CAA ACA ACC

G   S   A   M   G   K   M   A   S   L   F   A   T   F   L   V   V   L   V   S   L   S   L   A   Q   T   T

Xmal                              FL                              NcoI      EGFP→

CGG GGA AGA CGA [CCA TCA CCA CCA CCA CCT TTT TTC TTT CTA TCT CCT CCT CCC CCA TCA] CCA TCA ACC ATG GTG AGC AAG...

ChemNMR Prediction Result:
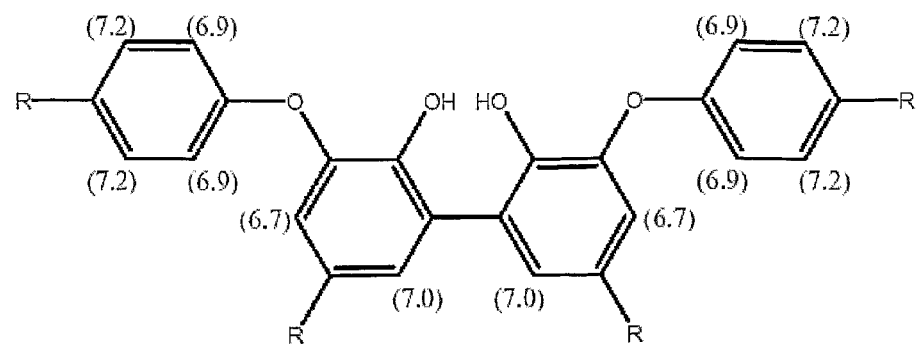
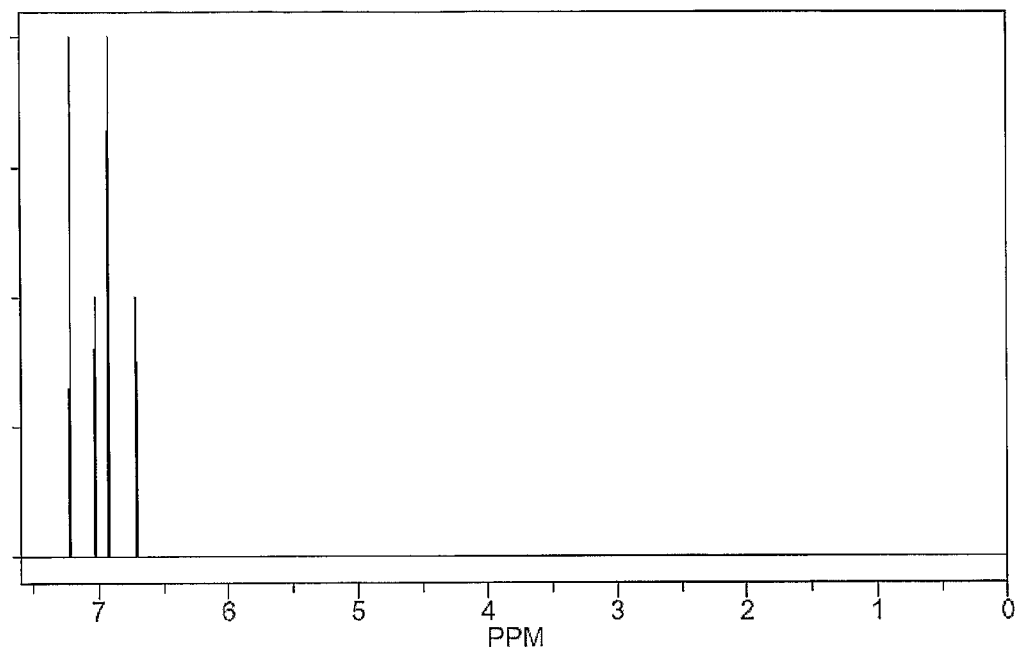
Figure 35

CROSS-LINKABLE GLYCOPROTEINS AND METHODS OF MAKING THE SAME

This application claims priority to U.S. Provisional Patent Application Nos. 60/563,349, filed Apr. 19, 2004, and 60/653,236, filed Feb. 15, 2005. The entire disclosures of these applications are incorporated herein by reference.

FIELD OF THE INVENTION

The invention is directed to methods of making crosslinkable molecules, such as peptides/polypeptides/proteins, by introducing a crosslinking motif into the molecule's structure, and the crosslinkable molecules made according to these methods.

BACKGROUND OF THE INVENTION

The Plant Cell Wall

The plant cell wall is composed of independent, interacting networks of cellulose microfibrils tethered by hemicellulosic polysaccharides, which are embedded in a matrix of pectins, glycoproteins, and phenolic substances (Carpita and Gibeaut 1-30). The plant cell wall is not an immutable substance; rather, it is a self-(re)organizing barrier able to respond to external and internal stimuli to govern cellular defense, growth, and development. For a size perspective, plant cell walls are approximately 0.1-10 μm thick depending on the type of plant species. In comparison, the plasma membranes of plant cells are not more than 0.01 μm thick (Stephen C. Fry).

Plant cell walls are generally subdivided into two types: the primary cell wall and the secondary cell wall. Primary cell walls are synthesized and modified during a period of active cell growth and are often referred to as "growing cell walls" (Kerr and Bailey 327-49). Secondary cell walls are deposited after cell growth has stopped. Since cell wall material is deposited from the inside out, the secondary cell wall is interior to the primary cell wall. Although the bulk of mature plant cell walls are composed of secondary wall material, there is great interest in the components of the primary cell wall, and their controlled assembly and modification, because primary cell walls dictate cell type, shape, and size, and provide a selective barrier to the external environment.

The Hydroxyproline-Rich Glycoproteins

The hydroxyproline-rich glycoproteins (HRGPs), which include the extensins, proline-rich proteins, and arabinogalactan-proteins, contribute to the extracellular matrix throughout the plant kingdom and the *Chlorophycean* green algae (Kieliszewski and Lamport 157-72; Showalter and Varner 485-520). HRGPs are involved in all aspects of plant growth and development involving wall architecture (Goodenough et al. 405-17; Roberts 129-46) and wall assembly during embryogenesis (Hall and Cannon 1161-72) as well as responses to biotic and abiotic stress (Merkouropoulos and Shirsat 356-66; Merkouropoulos, Barnett, and Shirsat 212-19; Yoshiba et al. 115-22) that include mechanical stress (Shirsat et al. 618-24); (Hirsinger et al. 343-55), physical wounding (Chen and Varner 2145-51; Han et al. 59-70; Showalter et al. 547-65; Zhou, Rumeau, and Showalter 5-17), pathogenesis (Benhamou et al. 457-67), and symbiosis (Cassab 441-46; Franssen et al. 4495-99; Frueauf et al. 429-38).

HRGPs are extended macromolecules consisting of small repetitive peptide and glycopeptide motifs that form peptide modules and glycomodules of functional significance, as in "mix-and-match" mode they define the molecular properties of the overall macromolecule (Kieliszewski et al. 538-47; Kieliszewski and Lamport 157-72). The glycomodules result from a combination of posttranslational modifications unique to plants, namely proline hydroxylation (Lamport 1438-40) and its subsequent glycosylation (Lamport 1322-24) that leads either to short arabinooligosaccharide or larger arabinogalactan polysaccharide addition to the Hyp residues. A sequence-dependent O-Hyp glycosylation code directs the precise addition of oligosaccharides and polysaccharides (Kieliszewski 319-23) and there is increasing evidence that other sequence-dependent codes direct inter- and intramolecular crosslinking of HRGPs. Crosslinked HRGPs, including extensins, contribute to wall architecture and defense responses by forming interpenetrating crosslinked networks in the wall. However, the precise identity of the intermolecular crosslink(s) has remained elusive.

The Extensins

Extensins are structural HRGPs that are covalently crosslinked into the primary cell wall, rendering them insoluble. Aside from being rich in Hyp, they also are rich in Ser, Tyr, Lys, Val and Thr. They are extensively post-translationally modified with short Hyp-O-oligoarabinosides and typically possess monogalactosyl-serine (Lamport, Katona, and Roerig 125-31; Lamport and Miller 454-56). Extensins are rigid linear molecules that adopt a polyproline II left-handed helical conformation (3 residues per turn, 9.4 Å pitch) (van Holst and Varner 247-51); (Heckman, Terhune, and Lamport 848-56); (Stafstrom and Staehelin 242-46).

Three major types of extensin precursors to the extensin network are widespread in dicot plants, namely Precursor 1 (P1) extensins that are characterized by the repetitive motif: Ser-Hyp-Hyp-Hyp-Hyp-Thr-Hyp-Val-Tyr-Lys (SEQ ID NO: 1), (Smith et al. 1021-30; Smith, Muldoon, and Lamport 1233-39), P2 extensins that contain repeats of the motif Ser-Hyp-Hyp-Hyp-Hyp-Val-Tyr-Lys-Tyr-Lys (SEQ ID NO: 2) (Smith et al. 1021-30; Smith, Muldoon, and Lamport 1233-39), and finally, the P3 extensins that contain a major palindromic (bolded) repeat: Ser-Hyp-Hyp-Hyp-Hyp-Ser-Hyp-Ser-Hyp-Hyp-Hyp-Hyp-Tyr-Tyr-Tyr-Lys (SEQ ID NO: 3) (Lamport 79-115; Smith et al. 1021-30).

The P1 and P2 extensins can be isolated by the salt-elution of intact cells as soluble monomer precursors to the extensin network (Fong et al. 548-52; Smith et al. 1021-30; Smith, Muldoon, and Lamport 1233-39). The P3 extensins, on the other hand, have never been isolated as monomeric precursors to the extensin network, presumably due to their rapid incorporation into the cell wall via covalent intermolecular crosslinking (Mort and Lamport 289-309). Consequently, the molecular properties of soluble monomeric P3 extensins have thus far been inferred from gene sequences, and P3 glycopeptides and peptides rendered from cell walls (Corbin, Sauer, and Lamb 4337-44; Lamport 1155-63; Lamport 27-31; Lamport 79-115; Lamport and Miller 454-56; Showalter et al. 547-65; Showalter and Varner 375-92; Zhou, Rumeau, and Showalter 5-17).

Intramolecular Extensin Crosslinking

Both P2 and P3 type extensins can undergo intramolecular crosslinking of Tyr residues (Epstein and Lamport 1241-46) (underlined in the sequences above) to form the diphenylether crosslink amino acid, isodityrosine (IDT) (FIG. 1) (Fry 449-55). First observed as an unknown tyrosine derivative in extensin peptides (Lamport 1155-63), and later identified in wall hydrolysates (Fry 449-55), and also as a component of trityrosine in *Ascaris* cuticle collagen (Fujimoto 637-43), IDT was initially hypothesized to be an intermolecular crosslink responsible for transforming the soluble extensin monomeric precursors, P1, P2 and P3, into an insoluble extensin network in muro (Fry 449-55); (Lamport and Epstein 73-83). But IDT was identified only as an intramolecular crosslink in P2 and P3-derived extensin peptides purified from enzymic digests of cell walls (Epstein and Lamport 1241-46) and extensin peptides crosslinked by intermolecular IDT have never been isolated. Although it has been suggested that extracellular peroxidases catalyze the formation of IDT, to date, the precise mechanism in muro remains a mystery (Fry 853-62).

Intermolecular Extensin Crosslinking

Evidence has suggested that pectin-protein crosslinks may play a role in extensin insolublization in muro (Keegstra et al. 188-96; Mort; Qi et al. 1691-701). Although these crosslinks may exist to some extent, the extensin network in cell walls and in vitro remains insoluble after complete deglycosylation with anhydrous hydrogen fluoride at 0° C. (Mort and Lamport 289-309; Schnabelrauch et al. 477-89). Furthermore, Hyp-rich extensin peptides are only released after proteolytic cleavage of a partially or fully deglycosylated extensin network (Lamport 1155-63; Lamport 79-115; Mort and Lamport 289-309; Qi et al. 1691-701). Thus, the insolubility of cell wall extensins is primarily attributed to a protein-protein and/or protein-phenolic-protein crosslink(s) (Mort and Lamport 289-309).

Peroxidase-catalyzed extensin intermolecular crosslinking has been demonstrated in vitro by several groups (Brownleader et al. 1115-23; Everdeen et al. 616-21; Jackson et al. 1065-76; Price et al. 41389-99; Schnabelrauch et al. 477-89), yet the molecular nature of the intermolecular crosslink(s) has not been were not identified. Indeed, Lamport and colleagues (Schnabelrauch et al. 477-89) found no IDT increase in P1 extensins after their crosslinkage in vitro by a tomato pI 4.6 extensin peroxidase, although the abundance of Val-Tyr-Lys motifs in several crosslinking extensins, including P1 and P2, suggested the intermolecular crosslinks involved tyrosine and/or lysine (Schnabelrauch et al. 477-89).

More recently, Brady and Fry identified a trimeric tyrosine derivative, pulcherosine (FIG. 2) and the tetrameric tyrosine derivative, di-isodityrosine (diIDT; FIG. 3) (Brady, Sadler, and Fry 349-53); (Brady, Sadler, and Fry 323-27) in tomato cell wall hydrolysates and speculated that IDT-containing extensins could be insolubilized through intermolecular IDT crosslinks forming pulcherosine and di-isodityrosine (FIG. 4). Also, as extensin incorporation into the cell wall increased, hydrolysates of these walls showed that the amounts of IDT decreased and diIDT increased (Brady and Fry 87-92). These findings suggest a significant role for IDT-rich extensins, which are supported by the recent discovery that RSH, an extensin containing 14 intramolecular IDT motifs, is crucially involved in positioning the cell plate during the earliest stages of embryogenesis in *Arabidopsis* (Hall and Cannon 1161-72).

However, to date, there has been no direct demonstration of an extensin intermolecular crosslink that involves either Tyr or Lys. The results of in vitro assays have been difficult to interpret, as the substrate extensins, P1 and P2, contain both Tyr and Lys and the amino acids formed by crosslinking were not identified (Brownleader et al. 1115-23; Everdeen et al. 616-21; Fujimoto 637-43; Hall and Cannon 1161-72; Schnabelrauch et al. 477-89). Other approaches involving the isolation of intermolecularly crosslinked peptides from the cell wall itself have also proven intractable (Epstein and Lamport 1241-46).

SUMMARY OF THE INVENTION

The present invention advances the art by, among other things, identifying a residue involved in glycoprotein crosslinking.

In order to simplify the results of in vitro crosslinking assays and to test for the involvement of Tyr and Lys in crosslinking, we created a series of extensin mutants using the synthetic gene approach described earlier (Kieliszewski 319-23; Shpak et al. 11272-78; Shpak et al. 11272-78; Shpak, Leykam, and Kieliszewski 14736-41; Tan L 1362-69; Tan, Leykam, and Kieliszewski 1362-69). The P3 extensin was of particular interest in view of its repetitive structure widespread in the plant kingdom and therefore functionally significant although frustratingly recalcitrant to isolation in precursor form; furthermore, it contains Tyr, Lys, and an intramolecular IDT motif. The synthetic gene approach allows us to explore the roles of IDT, Tyr, and Lys in crosslinking, and eventually to test the proposed role of the palindromic motif in molecular recognition (Kieliszewski and Lamport 157-72).

Thus, we designed a series of synthetic genes, one encoding twenty and the other eight repeats of the P3 repetitive subdomain: Ser-Hyp-Hyp-Hyp-Hyp-Ser-Hyp-Ser-Hyp-Hyp-Hyp-Hyp-Tyr-Tyr-Tyr-Lys (SEQ ID NO: 3), as well as variants containing Tyr-Phe and Lys→Leu mutations. Overexpression of these genes as enhanced green fluorescent protein (EGFP) fusion proteins in BY-2 tobacco cells yielded secreted transgenic extensins. They were glycosylated as predicted by the Hyp contiguity hypothesis and contained IDT similar to native P3-type extensins. Furthermore, the pI 4.6 extensin peroxidase (E.C. 1.11.1.7) (Schnabelrauch et al. 477-89) catalyzed intermolecular crosslinking only between those P3 extensin analogs which contained Tyr. The present invention advances the art by, among other things, identifying a particular residue, i.e., tyrosine, involved in crosslinking.

Thus, by using consensus sequences that are targeted for crosslinking, novel molecules can be created, which will form crosslinks. The consensus sequence for crosslinking is Tyr-X-Tyr, where X is any amino acid. In some embodiments, X is chosen from Tyr, Lys, and Val. The crosslinks that can form with this motif can be intermolecular or intramolecular. By inserting these sequences into proteins, crosslinkable proteins are generated.

The present invention provides, for example, crosslinked fibers, emulsifiers, moleclular scaffolds, etc. Other specific applications of the invention include, but are not limited to, biologically active films. For example, a crosslinkable chimera involving an enzyme at one end (e.g., nitric oxide synthase or peroxidase or any other enzyme) and crosslinking extensin repeats at the other, would allow for an immobilized enzyme in a film to make a biosensor or for implantation at a wound site. Other immobilized proteins include, but are not limited to, lectins (which bind carbohdrate residues) and protein sequences that can chelate metals, etc. It is also contemplated that arabinogalactan modules (X-Hyp-X-Hyp) with extensin arabinosylation modules (X-Hyp$_n$) can be combined with crosslinking modules and with non-HRGP modules to create novel combinations.

The present invention provides non-naturally occurring proteins comprising the amino acid sequence Tyr-X-Tyr, wherein X is chosen from any amino acid. In some embodiments, X is chosen from Tyr, Lys, and Val. In some embodiments, the protein is intermolecularly crosslinked to a non-naturally occurring protein comprising the amino acid sequence Tyr-X-Tyr. In some embodiments, the non-naturally occurring protein is intramolecularly crosslinked to itself.

The non-naturally occurring proteins of the invention can further comprise the amino acid sequence X-Hyp$_n$, wherein X is any amino acid, and n is from 1 to about 1000. In some embodiments, X is chosen from Ser, Ala, Val, and Thr. The non-naturally occurring proteins of the invention can also further comprise the amino acid sequence X-Hyp-X-Hyp, wherein X is any amino acid. In some embodiments, X is chosen from Ser, Ala, Val, and Thr.

The non-naturally occurring proteins of the invention can be crosslinked by reactions that involve the oxidation of tyrosine. Such reactions can be catalyzed by peroxidases, including but not limited to, horseradish peroxidase, tomato peroxidase, extensin peroxidase, etc.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIG. 1 shows the chemical structure of isodityrosine (IDT). (MW=360; (Fry, S. C. 1982))

FIG. 5 shows oligonucleotide sets for construction of the synthetic genes: (A) FK9, (B) YK, (C) YL, and (D) FL. (A) Construction of the FK9 gene involved three sets of partially overlapping, complementary oligonucleotide pairs that were polymerized head-to-tail as described earlier (McGrath, K. P. et al. 1990) (Shpak, E. et al. 1999). Nine internal repeats and one of each linker set made up the FK9 synthetic gene. The restriction sites used for subcloning are highlighted and labeled. The YK, YL, and FL genes were constructed through primer extension of the sense and antisense oligonucleotide sets shown in (B), (C), and (D) which involved elongation through use of the complementary but nonregenerable BbsI and BsmFI restriction sites. As the enzymes BbsI and BsmFI do not restrict the site that they recognize, both the recognition sequence and the sequence that is restricted are highlighted with the same color, the label directly placed above the recognition site. The underlined sequences in (B) (C) and (D) indicate the 24 base pair overlapping sections of the oligonucleotide sets (SEQ ID NOS 111-131 are disclosed respectively in order of appearance).

FIG. 11 shows oligonucleotide sequences of PCR and DNA sequencing primers. (a) M13 forward primer is complimentary to 21 bp upstream of the MCS region of pUC 18 and was used for sequencing synthetic genes in pUC vectors. (b) The tobacco signal sequence primer (SSeq4Sen) binds 4 bp into the signal sequence and was used for PCR of genomic DNA from transformed cell lines as well as the DNA sequencing of the PCR products. (c) The EGFP primer (EGFP566 as) is complimentary to the sense strand of the EGFP gene 566 bp from the origin. This oligonucleotide was used for PCR of genomic DNA and the sequencing of synthetic genes in both pUC and pBI121 vectors. All oligonucleotide primers were ordered from Integrated DNA Technologies (SEQ ID NOS 132-134 are disclosed respectively in order of appearance).

FIG. 13 shows the DNA and encoded protein sequences of the P3-type extensin analogs. (A) SStob-YK8-EGFP and SStob-YK20-EGFP (SEQ ID NOS 135 & 136), (B) SStob-YL8-EGFP and SStob-YL20-EGFP (SEQ ID NOS 137 & 138), (C) SStob-FK9-EGFP (SEQ ID NOS 139 & 140) and (D) SStob-FL8-EGFP (SEQ ID NOS 141 & 70). Each gene encoded a signal sequence, a P3 extensin analog, and EGFP, which is presented only in part. The XmaI and NcoI sites allowed insertion of the genes into the modified pUC18 vector described earlier (Shpak, E. et al. 1999) between the signal sequence-encoding region (SStob) and EGFP. The BamHI site together with a SacI site (not shown) located at the 3'end of EGFP allowed insertion of SStob-YK20-EGFP and the other constructions into the binary plant transformation vector, pBI121.

FIG. 35 shows a predicted 1-D $^1$HNMR spectrum of diIDT.

DESCRIPTION OF THE EMBODIMENTS

Figure 2:
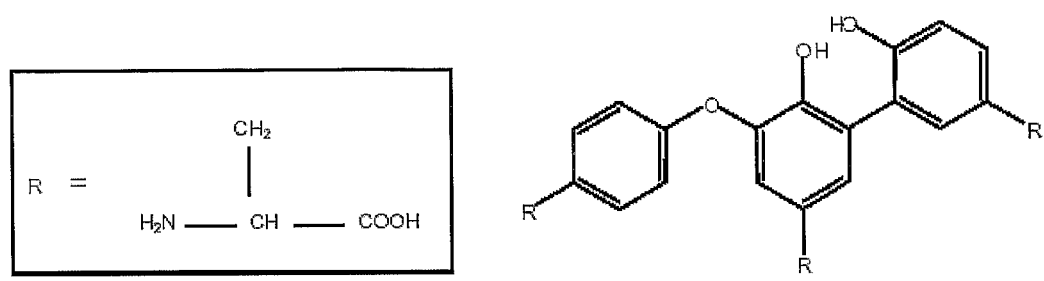
FIG. 2 shows the chemical structure of pulcherosine. (MW=539; (Brady, J. D. et al. 1998))
Figure 3:
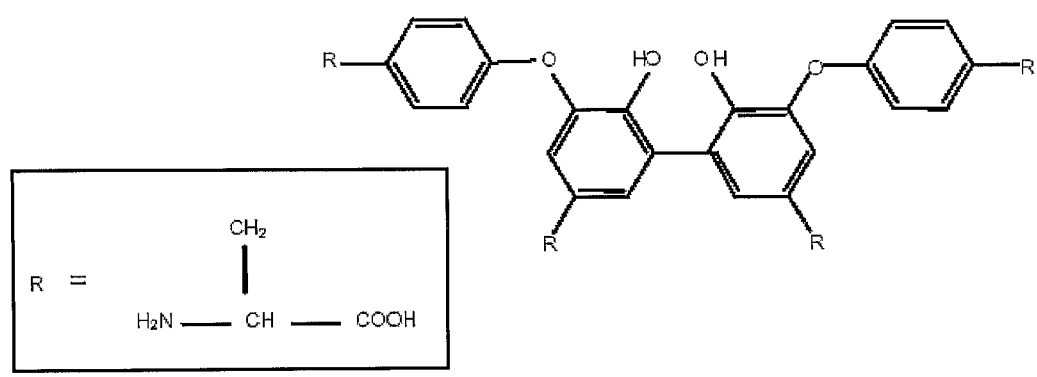
FIG. 3 shows the chemical structure of diisodityrosine (diIDT). (MW=718; (Brady, J. D. et al. 1996))
Figure 4:
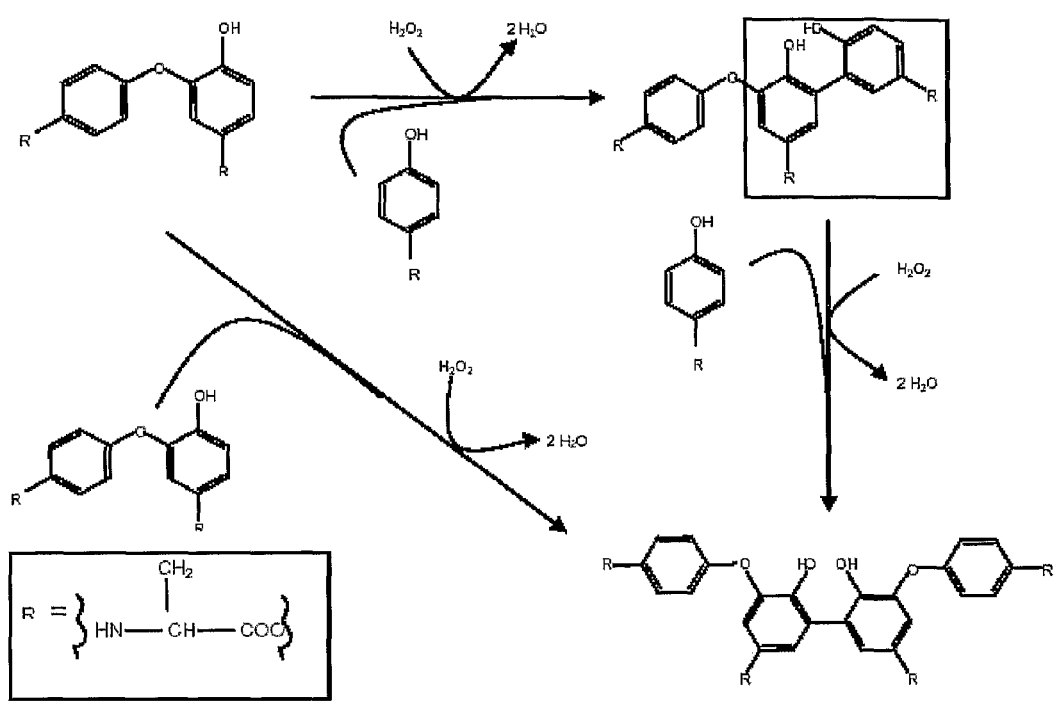
FIG. 4 illustrates a possible in muro mechanism of pulcherosine and diIDT formation. From Brady et al. 1996, 1997, and 1998, pulcherosine must come from the oxidative coupling of 1 IDT with yr; DiIDT must come from the oxidative coupling of either pulcherosine and Tyr or 2 IDTs, as biphenyl linked dityrosine (upper right, boxed) is not found in plants.

Reference will now be made in detail to the present embodiments (exemplary embodiments) of the invention.

The following abbreviations are used throughout this application: 1-D $^1$HNMR: 1-D proton nuclear magnetic resonance; ABTS: 2,2'-azino-bis(3-ethylbenzthiazoline-6-sulfonic acid); ACS: American chemical society; BAW: Butanol:acetic acid:water (12:3:5) by volume; bp: base pair; BSA: Bovine serum albumin; BY-2: Bright yellow-2 *Nicotiana tabacum*; CaMV 35S: Cauliflower mosaic virus 35S promoter; CHO: carbohydrate; Da: Daltons; ddH$_2$O: distilled deionized water; DEAE: diethylaminoethyl; diIDT: diisodityrosine; *E. Coli*: *Escherichia coli*; E1: crude peroxidase preparation from untransformed tobacco culture medium; E2: crude peroxidase preparation from salt-eluates of untransformed tobacco cells; % GC: percentage of guanine and cytosine base pairs; EGFP: enhanced green fluorescent protein; emm: emission wavelength; exc: excitation wavelength; Fry's diIDT: authentic diisodityrosine standard from Dr. Stephen C. Fry; HF: anhydrous hydrogen fluoride; HIC: Hydrophobic interaction chromatography; HMW: High molecular weight; HPLC: High performance liquid chromatography; HRGP: Hydroxyproline-rich glycoprotein; Hyp: Hydroxyproline; Hyp-O-Aran: O-linked hydroxyproline oligoarabinosides; Hyp-PS: O-linked hydroxyproline arabinogalactan polysaccharide; IDT: isodityrosine; LB: Luria broth; MALDI-TOF MS: Matrix assisted laser desorption ionization-time of flight mass spectrometry; MCS: Multiple cloning sequence; MS: Mass spectrometry; MW: Molecular weight; MWCO: Molecular weight cut-off; My diIDT: Diisodityrosine standard isolated by the inventor; NG-Hyp: Non-glycosylated Hydroxyproline; NOS pro: nopaline synthesis promoter; NOS ter: nopaline synthesis terminator; NPT II: Neomycin phosphotransferase II gene; Nt: *Nicotiana tabacum*; NT-1: *Nicotiana tabacum* 1 culture medium; P1: Precursor 1 extensin; P1XL: crosslinked P1 extensin; P2: Precursor 2 extensin; P3: Precursor 3 extensin; PCR: Polymerase chain reaction; PCV: Packed cell volume; PITC: phenylisothiocyanate; PTC-aa: phenylthiocarbamyl-amino acid derivative; Rf: relative to the solvent front; RSH: *Arabidopsis* mutant "Root-Shoot-Hypocotyl" defective; SEC: Size exclusion chromatography; Ser-O-gal: O-linked monogalactosylserine; SH: Schenk and Hildebrandt; SH*: SH medium lacking kinetin; SStob: tobacco signal sequence; TaOpt: Optimum annealing temperature; TFA: Trifluoroacetic acid; Tm: Melting temperature; uTob: untransformed tobacco BY-2 cells; YK20: YK20 glycomodules; and YK20XL: crosslinked YK20 glycomodule.

Earlier work using a synthetic gene approach allowed us to elucidate the codes that drive Hyp-O-glycosylation in plants (Shpak et al. 11272-78; Shpak, Leykam, and Kieliszewski 14736-41; Tan, Leykam, and Kieliszewski 1362-69). Here we have extended this work to the extensins, not only as another test of the Hyp contiguity hypothesis for glycosylation, but also to examine codes for other posttranslational modifications, including intra- and intermolecular extensin crosslinking, which is a long-standing and formidable problem relevant to plant growth, development, and disease resistance. Thus, we designed a series of crosslinking and non-crosslinking P3-type extensin analogs for their subsequent expression and isolation.

P3-type extensins play a crucial role in the cell wall, judging from their ubiquity and their highly conserved repetitive sequences that include palindromic (bolded) and IDT motifs (underlined): Ser-Hyp-Hyp-Hyp-Hyp-Ser-Hyp-Ser-Hyp-Hyp-Hyp-Hyp-Tyr-Tyr-Tyr-Lys (SEQ ID NO: 3). Such supersymmetry combined with potential intra- and intermolecular crosslink sites involving IDT may enhance self-assembly of tightly packed networks (Knupp and Squire 558-77). Likewise, the related RSH extensin required for cell plate orientation during cytokinesis (Hall and Cannon 1161-72) contains 14 IDT motifs and a repetitive symmetry that, although not palindromic, should favor close packing.

Figure 7:
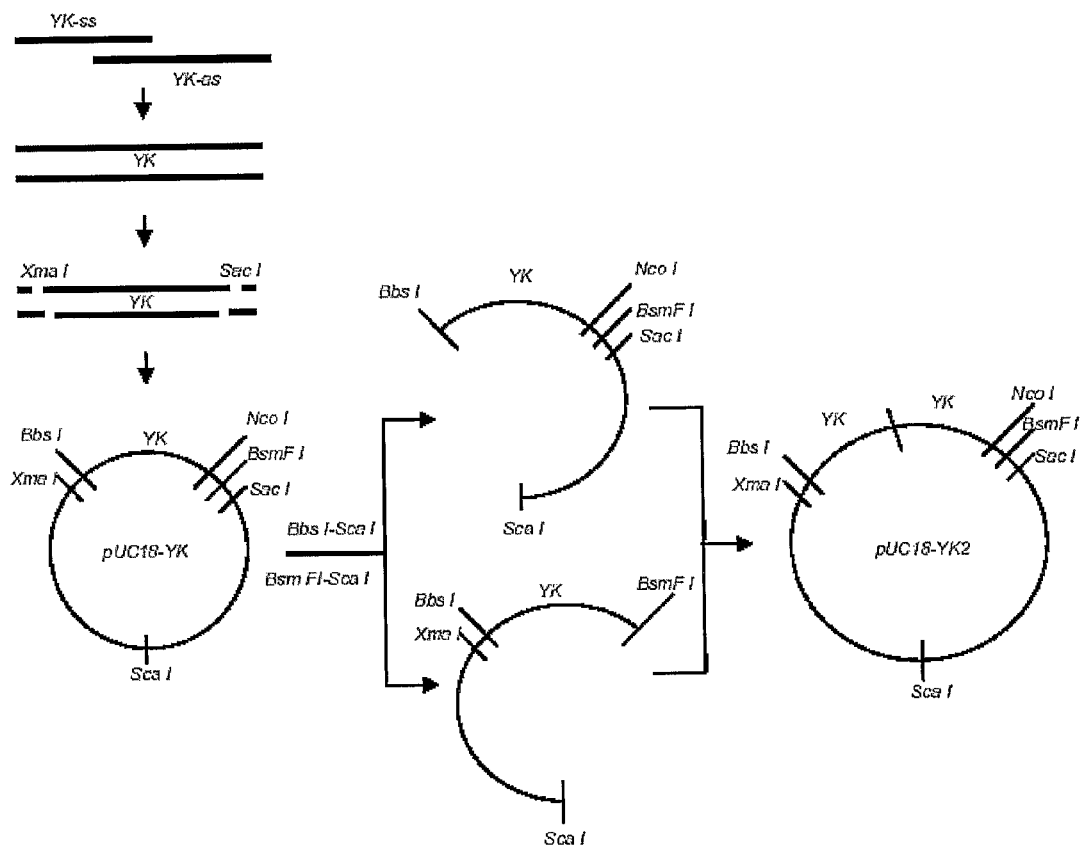
FIG. 7 illustrates the construction of the YK20, YK8, and YL8 using oligonucleotides containing complementary, non-regenerable restriction sites. This approach used general methods developed earlier (Lewis, R. V. et al. 1996). Primer extension of the sense and antisense overlapping oligonucleotide sets shown in FIGS. 5B, C, and D (here designated YK-ss and YK-as, respectively) initially gave genes having a single repeat (upper left) which were inserted into pUC18 as XmaI/SacI fragments and then sequenced. The resulting plasmid, here designated pUC18-YK, was divided into two aliquots; one aliquot was restricted with BbsI and ScaI and the other with BsmFI and ScaI. The BbsI/ScaI and BsmFI/ScaI fragments were isolated, annealed to each other through the complementary nonregenerable BbsI/BsmFI site and the ScaI site, then ligated to give rise to pUC18-YK2. Longer P3 analog genes were made by repeating the procedure.

Two methods were used to make the synthetic genes. One involved polymerization of duplex DNA oligomer sets (the FK set in FIG. 1A) (McGrath et al. 186-92; Shpak, Leykam, and Kieliszewksi 14736-41), the result being small genes containing at most only nine internal repeats. A second approach (Lewis et al. 400-06) was used to make the YK20, YK8, and YL8 genes and allowed precise control of the sizes. This strategy involved compatible but nonregenerable restriction sites to generate a gene with double the number of repeats of the starting gene (FIG. 7). Judging from extensin genes, it was estimated that 20 repeats represented a 'full length' extensin, containing about 320 amino acids (Zhou, Rumeau, and Showalter 5-17), although there is considerable variation in extensin lengths. Therefore, one construction, YK20, was made containing 20 palindromic P3 crosslinking modules. Shorter variants, namely YK8, YL8 and FK9, were also made to determine if the number of repeats influenced crosslinking rates and to determine the amino acid requirements for crosslinking. This method is completely amenable to any insert sequence (HRGP or other), for example, by using BbsI and BsmFl restriction enzymes that have separate recognition and restriction sites. This method also allows the design of synthetic genes having more than one consensus sequence. For instance, repeat units can be combined to control crosslink densities and/or to create modules such as AGP/extensin chimeras.

Transformation of tobacco BY2 cells with the synthetic genes yielded several cell lines for each construction. Cell lines releasing the most fusion protein into the medium were chosen for isolation and biochemical characterization of the transgene products. The yields were on the level of those previously reported (Shpak et al. 11272-78; Tan L 1362-69; Zhao et al. 431-44). Transformed tobacco cells were maintained in SH medium lacking kinetin as this seemed to improve secretion and overall fusion protein yields as compared with SH medium (not empirically determined).

A combination of HIC, gel filtration, and reversed phase chromatographies (FIG. 18) gave pure fusion proteins judging by N-terminal sequence analyses that yielded a single sequence for each protein (Table 5). The amino acid compositions of the isolated YK20, YK8, YL8, and FK9 glycoproteins were also consistent with those predicted by the genes (Table 4) although values for Hyp/Pro and Ser were somewhat lower than predicted. Virtually every Pro residue was hydroxylated and the modules containing Tyr showed conversion of Tyr to IDT. The PTC-isodityrosine was extremely hydrophobic and eluted with and was indistinguishable from the reagent peaks at the end of the gradient during amino acid analysis. Therefore, IDT was quantified from acid hydrolysates fractionated on a gel filtration column (Schnabelrauch et al. 477-89) (FIG. 21) compared to an authentic IDT standard (a gift from Dr. Derek Lamport). Putative IDT motifs of extensins are widespread and quite variable throughout plant species (Table 15). Comparison of the amounts of IDT in YK8 and YL8, show that not all -Y-Y-Y-X-motifs form IDT to the same extent. In other words, the flanking X residue (K or L) appears to

TABLE 15

Putative IDT motifs found in extensin genes of various plants.

| Putative IDT Motif (SEQ ID NOS 7-69) | Plant species |
|---|---|
| YYYK | Brassica napus, Phaseolus vulgaris, Solanum tuberosum, Vigna unguiculata, Glycine max, Manihot esculenta, Lycospersicon esculenta, Cicer arietinum, Bromheadia finlaysonia, Petroselinum crispum, Medicago trucatula, Pisum sativum, Vicia faba |
| YYYH | Brassica napus, Phaseolus vulgaris, Glycine max, Manihot esculenta, Lycospersicon esculenta, Cicer arietinum, Arabidopsis thaliana |
| YYYS | Brassica napus, Lycospersicon esculenta, Petroselinum crispum, Arabidopsis thaliana, Nicotiana sylvestris, Oryza saliva |
| YYYQ | Brassica napus, Phaseolus vulgaris, Petroselinum crispum, Pisum sativum, Lupinus angustifolius |
| YYYN | Brassica napus, Phaseolus vulgaris, Vigna unguiculata, Arabidopsis thaliana |
| YYYY | Phaseolus vulgaris, Oryza sativa, Lupinus angustifolius |
| YYYT | Solanum tuberosum, Petroselinum crispum, |
| YYYV | Phaseolus vulgaris |
| YYYI | Bromheadia finlaysonia |
| YYYL | Arabidopsis thaliana |
| YHY | Brassica napus, Phaseolus vulgaris, Glycine max, Lycospersicon esculenta, Cicer arientinum, Arabidopsis thaliana, Pisum sativum, Nicotiana tabacum |
| YHYV | Phaseolus vulgaris ,Glycine max, Cicer arietinum, |
| YHYS | Pisum sativum, Catharanthus roseus |
| YHYT | Glycine max, Cicer arietinum |
| YHYY | Catharanthus roseus, Nicotiana sylvestris, |
| YHYQ | Cicer arietinum |
| YHYH | Arabidopsis thaliana |
| YHYE | Daucus carrota |
| YVYK | Brassica napus, Solanum tuberosum, Vigna unguiculata, Glycine max, Lycospersicon esculenta, Arabidopsis thaliana, Lupinu angustifolius, Adiantum capillus-veneris, Catharanthus roseus |
| YVYS | Vigna unguiculata, Arabidopsis thaliana, Pisum sativum, Nicotiana sylvestris |
| YVYQ | Brassica napus |
| YVYG | Vigna unguiculata |
| YVY | Arabidopsis thaliana |
| YVYN | Arabidopsis thaliana |
| YVYH | Arabidopsis thaliana |
| YVYA | Nicotiana tabacum |
| YKYK | Phaseolus vulgaris, Solanum tuberosum, Vigna unguiculata, Glycine max, Pisum sativum, Adiantum capillus-veneris, Catharanthus roseus, Nicotiana sylvestris, Daucus carota |
| YKYS | Phaseolus vulgaris, Pisum sativum, Catharanthus roseus |
| YKYP | Phaseolus vulgaris, Glycine max, Pisum sativum, Vicia faba |
| YKYN | Phaseolus vulgaris, Pisum sativum |
| YKYY | Lycospersicon esculenta |
| YKYQ | Pisum sativum |
| YIYK | Phaseolus vulgaris, igna unguiculata, Glycine max, Cicer arietinum, Arabidopsis thaliana, Lupinus angustifolius, Adiantum capillus-veneris, Catharanthus roseus |
| YIYA | Phaseolus vulgaris, Glycine max, Manihot esculenta, Cicer arietinum, Arabidopsis thaliana, Pisum sativum |
| YIYS | Phaseolus vulgaris, Glycine max, Bromheadia finlaysonia, Arabidopsis thaliana |
| YIYG | Lycospersicon esculenta |
| YIYN | Arabidopsis thaliana |
| YLYK | Arabidopsis thaliana, Lupinus angustifolius, Adiantum capillus-veneris, Nicotiana tabacum |
| YLYS | Cicer arietinum, Arabidopsis thaliana, Pisum sativum, Lupinus angustifolius |
| YLYN | Vigna unguiculata |
| YLYT | Lycospersicon esculenta |
| YLYA | Nicotiana tabacum |
| YSYS | Phaseoulus vulgaris, Vicia faba |
| YSYA | Phaseoulus vulgaris |
| YSYD | Lycospersicon esculenta |
| YSYN | Oryza sativa |
| YSYT | Daucus carota |
| YPYL | Vigna unguiculata |
| YPYT | Arabidopsis thaliana |
| YPYS | Arabidopsis thaliana |

TABLE 15-continued

Putative IDT motifs found in extensin genes of various plants.

Putative IDT Motif
(SEQ ID NOS 7-69) Plant species

| Motif | Plant species |
|---|---|
| YDYT | Lycospersicon esculenta |
| YDYN | Arabidopsis thaliana |
| YEYK | Brassica napus, Vigna unguiculata, Arabidopsis thaliana |
| YEYS | Arabidopsis thaliana, Oryza sativa |
| YGYT | Zea diploperennis |
| YGYG | Zea mays |
| YQYK | Vigna unguiculata, Adiantum capillus-veneris |
| YQYS | Nicotiana tabacum |
| YAYK | Lupinus angustifolius |
| YFYS | Brassica napus, Adiantum capillus-veneris |
| YMYK | Brassica napus |
| YNYS | Arabidopsis thaliana |
| YTYS | Lycospersicon esculenta, Daucus carota |

A short-nearly exact protein blast of http://www.ncbi.nlm.nih.gov/BLAST/ with the query "SPPPPYYYK" revealed extensin genes having putative IDT motifs in at least 23 different plant species.

Because endogenous P3 extensins are normally insoluble in muro, their precursor forms have not been isolated. Thus, P3 glycosylation profiles can only be inferred from P3 extensin genes (Zhou, Rumeau, and Showalter 5-17) and from Hyp-glycoside profiles of P3 glycopeptides enzymatically released from the walls (Lamport 79-115). The Hyp-contiguity hypothesis (Kieliszewski et al. 2541-49; Kieliszewski and Lamport 157-72; Shpak et al. 11272-78; Shpak, Leykam, and Kieliszewski 14736-41) predicts that P3 extensins, with their abundant contiguous Hyp and non-clustered single Hyp residues, should be extensively arabinosylated mainly with tetra- and triarabinooligosaccharides but lack arabinogalactan polysaccharides (Tables 2 and 3). The monosaccharide compositions and Hyp-glycoside profiles of YK20-EGFP, YK8-EGFP, YL8-EGFP, and FK9-EGFP were consistent with earlier P3 glycopeptide profiles (Lamport 1155-63) and with the predictions for Hyp-glycosylation, the exception being a small amount of Hyp-polysaccharide in YL8-EGFP (Table 3). Judging by earlier Hyp-glycosylation profiles of HRGP analogs having only tandem repeats of the pentapeptide (Ser-Hyp-Hyp-Hyp-Hyp)$_n$ or the dipeptide (Ser-Hyp)$_n$ (Shpak et al. 11272-78; Shpak, Leykam, and Kieliszewski 14736-41), it was inferred that the arabinogalactan polysaccharide probably occurs on 2 out of the 8 lone Hyp residues occupying the center (underlined) of the palindromic repeats: Ser-Hyp-Hyp-Hyp-Hyp-Ser-Hyp-Ser-Hyp-Hyp-Hyp-Hyp-Tyr-Tyr-Tyr-Leu (SEQ ID NO: 71).

As essentially all of the Pro residues in the isolated modules were hydroxylated (Table 4), it was determined that YK20 contained about 180 Hyp residues, YK8 and YL8 contained about 72, and FK9 about 81. Of the total Hyp residues in each glycoprotein, only 3-8 percent (i.e. 3 to 7 Hyp residues/glycoprotein) were not glycosylated, which indicated that often all Hyp residues in the 16-residue repeats were arabinosylated, including the non-contiguous Hyp. This is consistent with earlier work which demonstrated that although contiguous Hyp residues are preferred arabinosylation sites, non-clustered, lone Hyp residues can be arabinosylated or remain non-glycosylated (Kieliszewski et al. 2541-49).

In addition to arabinosides, extensins generally contain monogalactosylated Ser (Lamport 1155-63; Lamport, Katona, and Roerig 125-31; Smith, Muldoon, and Lamport 1233-39) and this seems to be true for YK20, YK8, FK9, and probably for YL8, although at least some of the Gal in YL8 occurs in the occasional arabinogalactan adduct present. The monosaccharide composition of YK20, YK8, and FK9 shows they contained about 1 mole of Gal for every 10-11 moles of Ara, which suggested monogalactose occurred on about 72-90% of the Ser residues in the P3-type module (Tables 7 and 9). This also is in agreement with native P3 glycopeptides isolated and characterized earlier from tomato cell walls (Lamport 27-31).

In Vitro Crosslinking of the P3 Extensin Glycomodules

Figure 25:
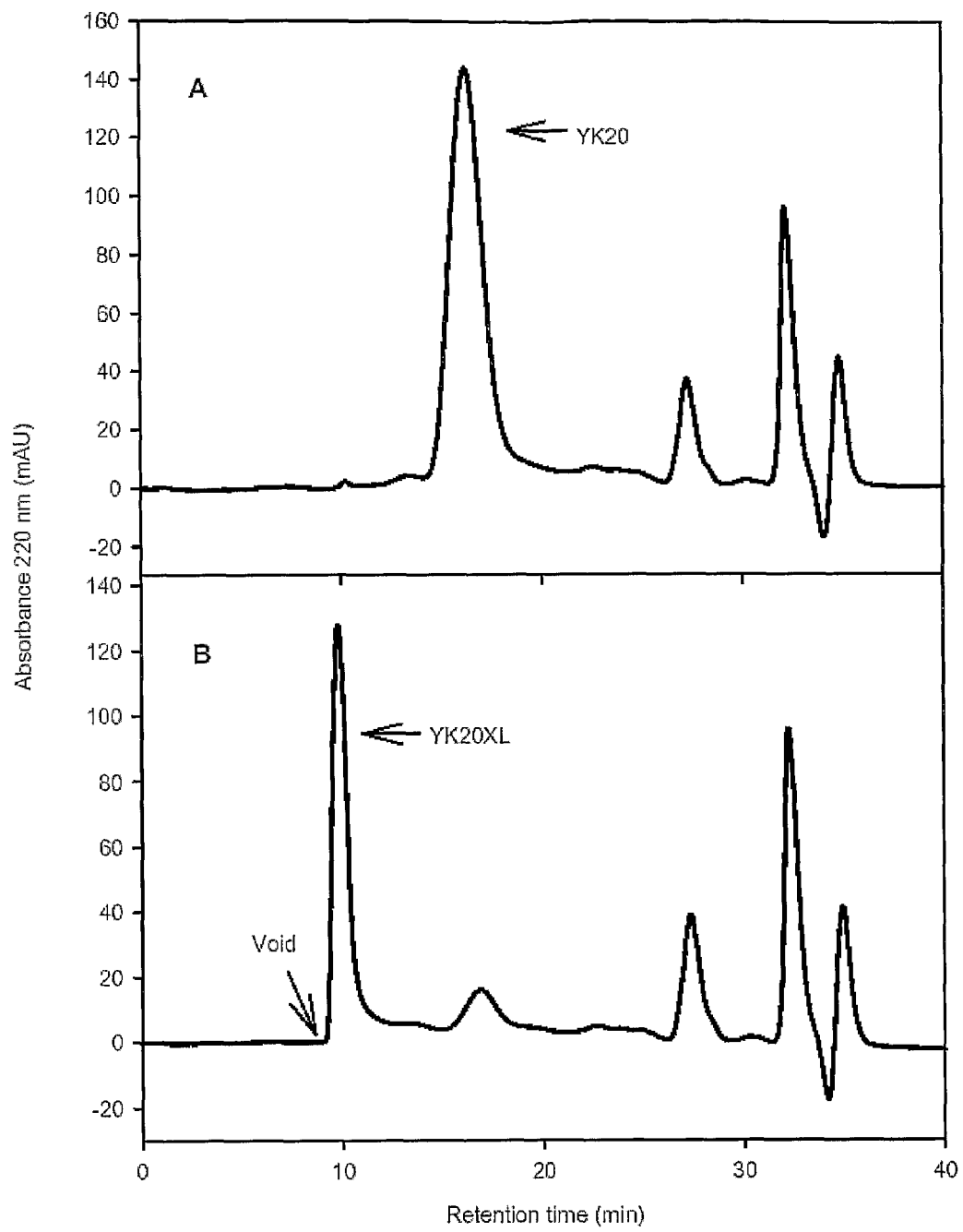
FIG. 25 shows in vitro crosslinking of YK20 (40 µg) by the pI 4.6 extensin peroxidase. Crosslinking reactions at time zero (A) and after 15 minutes of incubation (B) were separated by Superose-6 gel filtration chromatography. YK20, monomeric YK20; YK20XL, crosslinked YK20. The pI 4.6 extensin peroxidase crosslinks YK20 in vitro.
Figure 31:
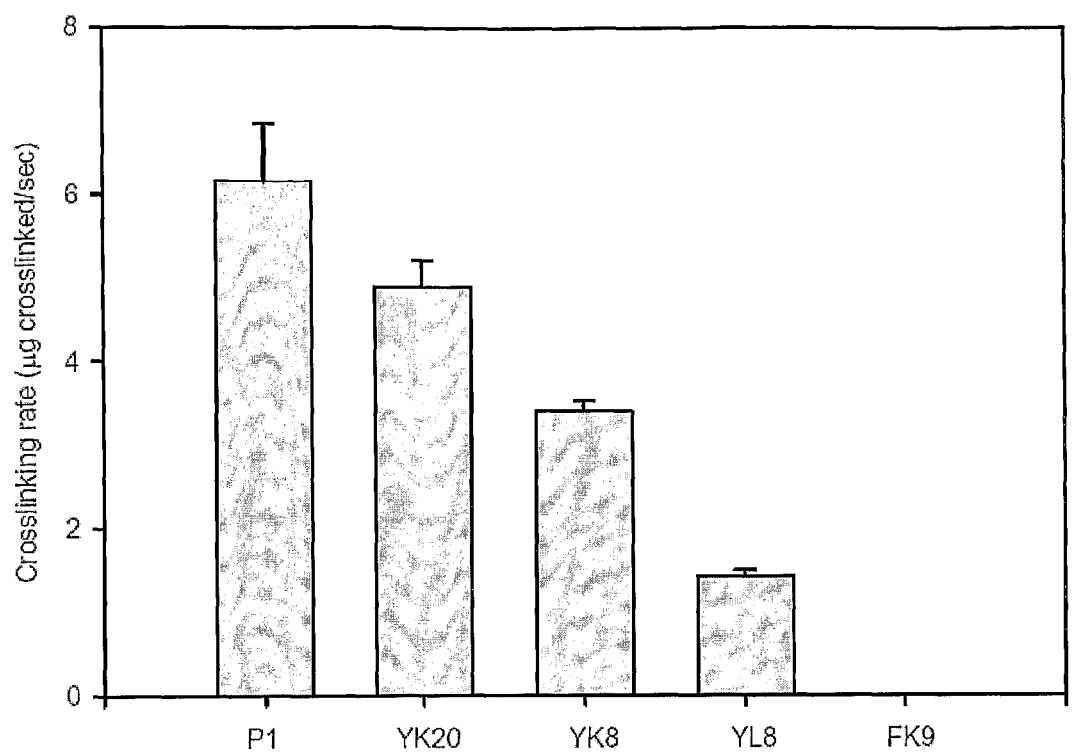
FIG. 31 shows crosslinking rates of P1, YK20, YK8, YL8, and FK9. Crosslinking rates were calculated as described earlier (Everdeen, D. S. et al. 1988) using the first order rate equation $A=A_o*e^{-kt}$ where A is the monomer remaining (µg) after t (sec) of incubation; Ao is the amount of monomer (µg) at time zero; k is the first order rate constant.

It was discovered that YK20 was an excellent crosslinking substrate for the well-characterized tomato pI 4.6 extensin peroxidase (Schnabelrauch et al. 477-89), with rates only somewhat lower than those for tomato extensin P1, which is presumably a natural substrate of the enzyme (FIGS. 25 and 31). Earlier it was proposed that valine, as in the putative P1 crosslinking motif Val-Tyr-Lys, was a requirement for intermolecular crosslinking of extensins by the pI 4.6 extensin peroxidase (Kieliszewski and Lamport 157-72). However, YK20 contained no valine.

Figure 16:
FIG. 16 is a visualization of plasmolyzed SS-EGFP, uTob, and YK20-EGFP cells by fluorescence microscopy. The (A) SS-EGFP, (B) uTob, (C and D) YK20-EGFP cells were plasmolyzed with 750 mM mannitol. The (E) YK20-EGFP cells were plasmolyzed with 500 mM potassium phosphate pH 7. Slides shown here are an overlay of the laser scanned image (exc. 488 nm, emm. 510 nm) and the transmitted light image. Green fluorescence in the cell walls after plasmolysis was not observed for cells expressing YK8-EGFP, YL8-EGFP, and FK9-EGFP.

Without wishing to be bound by any particular theory, the underlying principle driving both P3 and P1 self-assembly/ molecular recognition for subsequent crosslinking may involve the inherent hydrophobicity of the putative crosslinking sites (Brady, Sadler, and Fry 323-27; Whitesides, Mathias, and Seto 1312-19), Val-Tyr-Lys in P1 and Tyr-Tyr-Tyr in the P3 motif. Polymers containing separate hydrophilic and hydrophobic regions, a characteristic of the extensins, self-assemble in aqueous solution largely due to the hydrophobic effect which drives non-polar regions away from water and toward each other (Whitesides, Mathias, and Seto 1312-19). Thus, it is believed that P1, YK20, YK8, and YL8 crosslinking is facilitated by the alignment of the hydrophobic crosslinking motifs with one another, which might be further favored by the concurrent alignment of the highly regular and hydrophilic Ser-Hyp$_4$ glycomodules (Brady, Sadler, and Fry 323-27; Kieliszewski and Lamport 157-72). The rapid rate of P3 crosslinking may partially explain why no one has isolated an endogenous P3-type extensin monomeric precursor to the wall network: it is very rapidly insolubilized in muro. Consistent with this likelihood was the incorporation of YK20-EGFP into the tobacco cell wall, presumably through crosslinking as the walls retained green fluorescence after plasmolysis in mannitol or in salt at concentrations that normally remove non-covelently bound material from the wall (FIG. 16). Since both YK8-EGFP and YL8-EGFP are able to undergo in vitro crosslinking, it had been expected to see them in the wall as well. This could be due to their size, which has an impact on crosslinking rates (FIG. 31). It is possible that such a small amount of YK8-

EGFP and YL8-EGFP is actually crosslinked into the wall that visualization was not possible by fluorescence microscopy, as the relatively low pH of the cell wall could have significantly decreased EGFP fluorescence (CLONTECH).

Two other parameters appeared to influence the crosslinking rates of the P3 analogs. The first is molecular length of the substrate. The rates of YK20 crosslinking, with 320 amino acids per molecule, were much greater than those of YK8, which possessed only 128 amino acids/molecule although both had the same number of potential crosslink sites per milligram (~0.17 mole/mg) of material and similar glycosylation profiles (Tables 2 and 3). Secondly, the presence of lysine in the Tyr-Tyr-Tyr-Lys (SEQ ID NO: 7) motif favored crosslinking judging by the rates for YK8, which were double those of YL8. It is possible that the lysine residue facilitates enzyme recognition of the crosslink site or assists catalysis.

Identification of the P3 Intermolecular Crosslink

Figure 26:
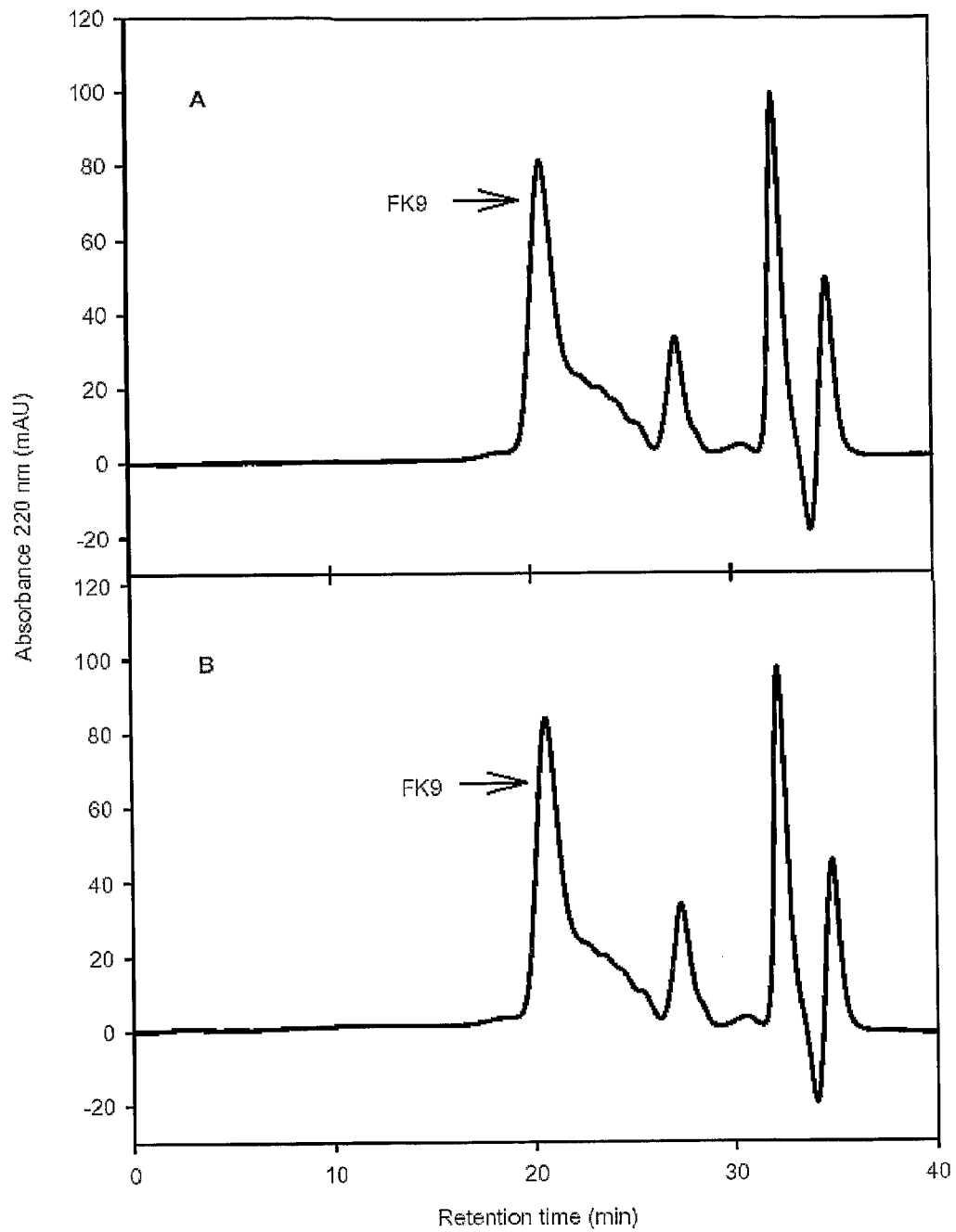
FIG. 26 shows in vitro crosslinking reactions of FK9 (40 µg). Crosslinking reactions at time zero (A) and after 15 minutes of incubation (B) were separated by Superose-6 gel filtration chromatography. Note FK9 did not crosslink in vitro. FK9 mono, monomeric.

The question of the crosslink identity arises and the enzyme or enzymes involved. Given the number of peroxidases in the extracellular matrix, including those that crosslink extensin in vitro (Jackson et al. 1065-76); (Price et al. 41389-99), it is likely that multiple extensin peroxidases exist having different affinities for different types of extensins and catalyzing a range of crosslinks. This might explain why peroxidases from tomato crosslink extensins at different rates: the basic peroxidase characterized earlier by Everdeen and colleagues (Everdeen et al. 616-21)) has a specific activity that is 2 to 3 orders of magnitude lower for P1 than the acidic pI 4.6 extensin peroxidase characterized later (FIG. 32) (Schnabelrauch et al. 477-89). All of the P3 analogs that contained tyrosine could be crosslinked by extensin peroxidase while FK9, which lacked tyrosine but had lysine, did not crosslink at all (FIGS. 26 and 31). Thus, in the modules tested here, Tyr, but not Lys, is directly involved in crosslinking. These results also indicated that the Val-Tyr-Lys motif is not required for all extensin crosslinking by the pI 4.6 extensin peroxidase (Schnabelrauch et al. 477-89) and suggest that different intramolecular crosslinks occur in extensin as the motif present in P1 (putatively Val-Tyr-Lys) differs substantially from the P3 motif (Tyr-Tyr-Tyr).

The exclusive involvement of Tyr in crosslinking of the P3 analogs described here raises questions about the involvement of the crosslink amino acid diisodityrosine (Brady, Sadler, and Fry 323-27). Characterized hydrolysates of crosslinked YK20 identified diisodityrosine as the crosslink amino acid produced during crosslinking (FIG. 33), judging by its atomic mass determined by MS (FIG. 34) and other properties (Brady and Fry 87-92) including NMR spectra of the isolated amino acid (Table 14 and FIGS. 34 and 35). Thus, these results lend strong support to the suggestion of Brady et al. (Brady, Sadler, and Fry 323-27) that diisodityrosine crosslinks are a mechanism for extensin insolubilization in muro.

Finally, this work demonstrates the general utility of a synthetic gene approach for elucidating the codes that direct the post-translational modifications of HRGPs, including glycosylation (Shpak et al. 11272-78; Shpak, Leykam, and Kieliszewksi 14736-41; Tan, Leykam, and Kieliszewski 1362-69) and crosslinking. The ramifications range beyond the roles of extensin in the wall to the module-by-module design of new glycoprotein-based biopolymers that combine the special properties conferred by glycosylation and crosslinking.

EXAMPLES

Example 1

Technical Basis for Crosslinking

Materials and Methods
Construction of P3-Type Synthetic Genes
Oligonucleotide Design The oligonucleotides coding for synthetic P3 extensin genes (FIG. 5) were designed taking into consideration known codon biases of native tobacco extensins (Showalter and Rumeau 247-81). Appropriate restriction sites for cloning and/or polymerization were designed into the oligonucleotides as described earlier (Lewis et al. 400-06; Shpak, Leykam, and Kieliszewski 14736-41). The oligonucleotide sequences were analyzed for secondary structure formation (i.e. hairpin and dimer formation), annealing temperature optimum (TaOpt), melting temperature (Tm), and false priming sites using Primer Premier software (Biosoft International, Palo Alto, Calif.) (Shpak, Leykam, and Kieliszewski 14736-41). The oligonucleotide sets were ordered from Integrated DNA Technologies (IDT, Coraliville, Iowa).
Construction of the FK9 Synthetic Gene
Annealing of the FK Oligonucleotide Pair Oligonucleotides for the sense and antisense FK internal repeats (FK-s and FK-as respectively; FIG. 5a) were each dissolved to 0.5 mM in sterile distilled, deionized water (ddH$_2$O). The FK-s and FK-as oligonucleotides (1.5 nmol each) were combined in 30 µl (total volume) of 1×T4 DNA ligase buffer (Promega, Madison, Wis.) and placed in a heating block at 97° C. for 5 min, slowly cooled to 60-65° C. over a period of 30 min, then cooled further to 55-60° C. over 30 min. The heating block was stabilized at the optimum annealing temperature (58° C., calculated using Primer Premier software) for 1 h. The annealed FK internal repeat pairs were stored at −20° C.
Annealing of the 5' Linker Oligonucleotide Pairs The 5' linker pair contained unique restriction sites for subcloning and was prepared by the annealing of oligonucleotides (5'-SP3-s) and (5-SP3-as) as previously described (Shpak, Leykam, and Kieliszewski 14736-41). Briefly, 4 nmol each of (5'-SP3-s) and (5'-SP3-as) were combined in 1×T4 DNA ligase buffer to a final volume of 80 µl. The reaction was heated to 95° C. for 5 min, cooled over 1.15 h to 47° C., then held at 47° C. for 1.3 h. The annealed 5' linker pairs were cooled to room temperature then stored at −20° C.
Ligation of the 5' Linker to the Annealed FK Internal Repeat Pair The annealed FK internal repeat pairs (0.5 nmol) were combined with the annealed 5' linker pairs (0.25 nmol) in 1×T4 DNA ligase buffer in a sterile screw cap microtube. The sample was heated to 68° C. for 25 min, then 45° C. for 5 min. After cooling to room temperature, 3 U of T4 DNA ligase (Promega) was added to the sample (40 µl final vol.). The reaction was incubated at ambient temperature for 3.6 h, and then cooled to 4° C. for 4.2 h. An additional 1.5 µl (0.075 nmol) of the annealed 5' linker pairs was added and the reaction mixture was incubated further at 4° C. overnight (~14 h). The extent of polymerization was assayed by agarose gel electrophoresis. Excess 5' linker pairs were removed by Sephacryl S-400 microspin column purification according to the manufacturer's instructions (Amersham Pharmacia Biotech, Piscataway, N.J.). Column eluates yielded 5' linker-FK internal repeats.

To maximize the number of contiguous FK internal repeat pairs ligated to each 5' linker pair, an additional 0.4 nmol of FK internal repeat pairs was added to the purified 5' linker-FK internal repeats along with ligase buffer. To re-initiate elongation, the reaction was heated to just under the Tm (70° C.) for 10 min, followed by 60° C. for 10 min, then 50° C. for 3 h, and finally cooled to room temperature. DNA Ligase (3U, Promega #M1801) was added in a final volume of 50 µl. The reaction was incubated 30 min at ambient temperature then held at 4° C. overnight.

Ligation of the Annealed 3' Linker Pair to 5' Linker-FK Internal Repeats

The annealed 3' linker pair (FIG. 5a) was prepared as described for the 5' linker pair. The 5' linker-FK internal repeats (1.17 nmol) was heated to 75° C. for 10 min. The annealed 3' linker pair (0.35 nmol) was added to the tube while still at 75° C. then returned to the heat block for an additional 10 min. The sample was slowly cooled, then held at 50° C. for 3 h. DNA ligase (3 U) was added at room temperature where it was incubated 3 h before being transferred to the refrigerator (4° C.). Unincorporated 3' linkerpairs were removed by Sephacryl S-400 microspin columns (Amersham Pharmacia). The purified 5' linker-FK internal repeats-3' linker synthetic gene was eluted from the column and stored at −20° C.

Creation of Plasmid pUC18-FK9

Figure 6:
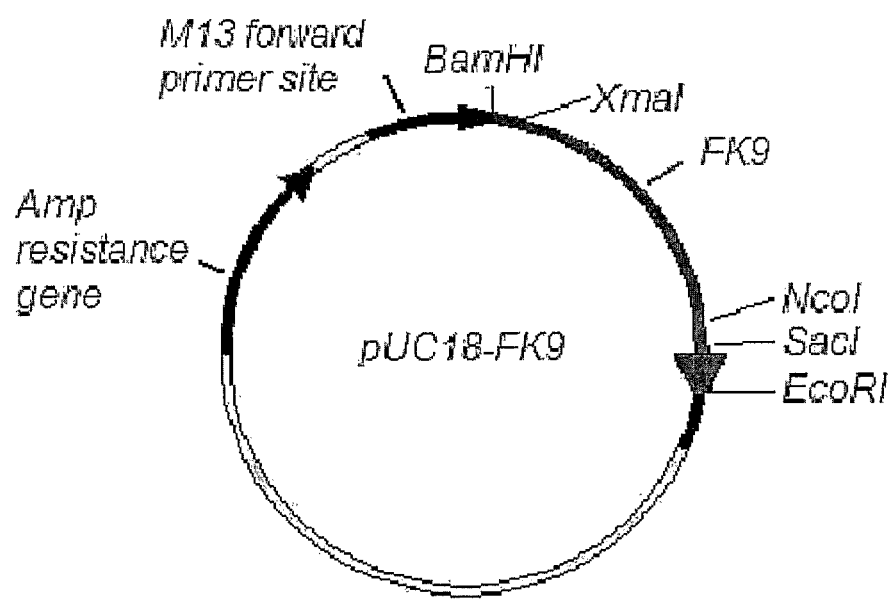
FIG. 6 illustrates a plasmid map of the pUC18-FK9 plasmid. The FK9 synthetic gene was inserted as BamHI-EcoRI fragment into a pUC18 vector.

The 5' linker-FK internal repeats-3' linker synthetic gene was subcloned into a pUC18 plasmid vector as a BamHI-EcoRI fragment (FIG. 6) (Shpak, Leykam, and Kieliszewski 14736-41). Plasmids were transformed into competent E. coli (XL1-Blue, Stratagene La Jolla, Calif.) and selected for ampicillin resistance. Positive transformants were cultured in 3.5 ml LB medium liquid cultures supplemented 50 µg/ml with ampicillin (220 rpm, 37° C.), from which pUC18-FK internal repeats plasmids were isolated using the Wizard Plus Minipreps, DNA Purification System (Promega, Madison, Wis.). Plasmids were screened for insert size by XmaI-NcoI digestion followed by 1% (w/v) agarose gel electrophoresis. A plasmid having nine contiguous FK internal repeats was selected (FK9), and sequenced.

Construction of YK, YL, and FL Synthetic Genes

A second method was used to build synthetic genes more similar in size to native extensins. This method was adapted from an existing method (Lewis et al. 400-06) and was used to build YK, YL, and FL gene constructs from new sets of oligonucleotide pairs (FIGS. 5B, C, and D). Restriction sites for BbsI, BsmFI, XmaI, NcoI, and SacI were engineered at the 5' and 3' ends of these new oligonucleotides for subcloning and polymerization (FIGS. 5B, C, and D).

Dried oligonucleotides were dissolved in ddH$_2$O to a concentration of 1 mg/ml. Corresponding sense (ss) and antisense (as) oligonucleotide pairs (34 µmol each) were combined, and diluted to 20 µl with ddH$_2$O. Oligonucleotide pairs were heat denatured at 94° C. for 7 min, then annealed to their respective complimentary 24 base pair annealing sites (60° C. for 5 min, followed by 45° C. for 10 min; FIGS. 5B, C, and D underlined). Samples were cooled to room temperature and primer extension was performed using DNA Polymerase I (Klenow) large fragment (Promega) according to manufacturers instructions (room temperature for 15 min, then heat stopped at 75° C. for 10 min). Reactions were loaded onto Sephacryl S-200 microspin purification columns (Amersham Pharmacia Biotech) to change the buffer and remove unincorporated nucleotides. Column eluates yielded duplex DNAs designated YK, YL, and FL (FIG. 7).

Creation of Plasmids pUC18-YK, pUC18-YL, and pUC18-FL

Figure 8:
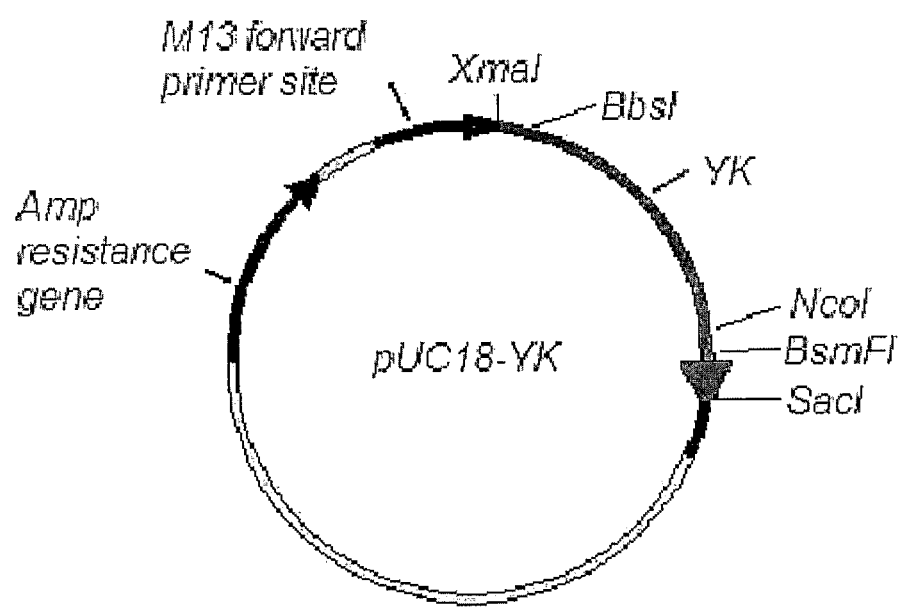
FIG. 8 illustrates a plasmid map of pUC18-YK. The YK synthetic gene was inserted as an XmaI-SacI fragment into the pUC18 plasmid. This procedure was also employed for the synthesis of pUC18-YL and pUC18-FL.

The YK, YL, and FL duplex DNAs were each digested with XmaI-SacI, followed by Sephacyl S-400 microspin column purification (Amersham Pharmacia Biotech) to remove the small restriction fragment ends (retained on the columns) from duplex DNA monomers. The YK, YL, and FL XmaI-SacI fragments were subcloned to pUC18 to yield plasmids pUC18-YK, pUC18-YL, and pUC18-FL (FIG. 8). Plasmids were sequenced with an M13 forward primer.

Creation of Plasmids pUC18-YK20, pUC18-YK8, pUC18-YL20, pUC18-YL8, and pUC18-FL8

Non-regenerable, complimentary sticky ends were produced by separate BsmFl-ScaI and BbsI-ScaI restrictions (New England Biolabs, Beverly, Mass.) of plasmid preparations harboring one repeat of the synthetic genes (FIG. 7). Ligation of the insert containing BsmFl-ScaI fragment with the insert containing BbsI-ScaI fragment produced plasmids possessing 2 repeats designated pUC18-YK2 and pUC18-YL2 respectively. This process was repeated to achieve plasmids of 8 and 20 internal repeats (pUC18-YK20, pUC18-YK8, and pUC18-YL8).

Figure 9:
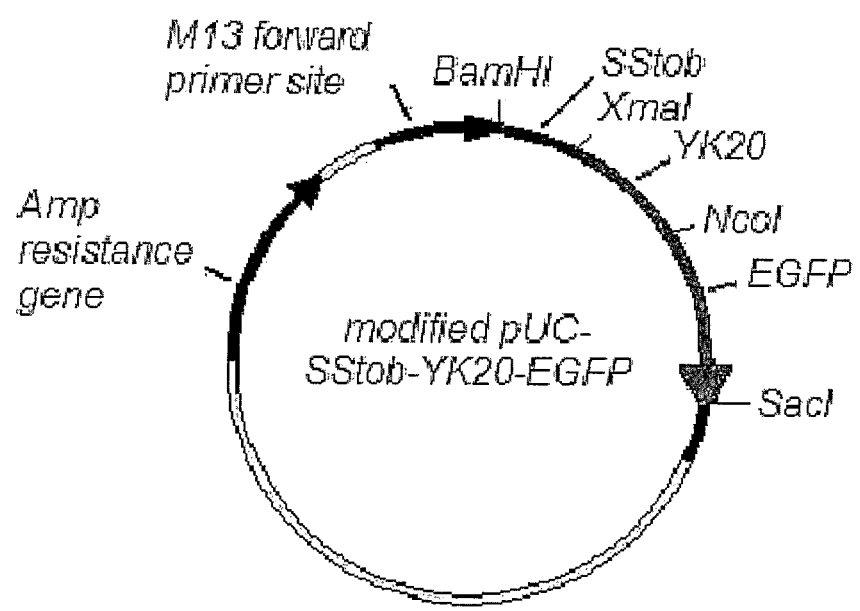
FIG. 9 illustrates a plasmid map of the modified pUC-SStob-YK20-EGFP. Synthetic genes YK20 (shown here), YK8, YL20, YL8, and FL8 were inserted as XmaI-NcoI fragments into the modified pUC-SStob-EGFP vector between SStob and the EGFP reporter gene.
Figure 10:
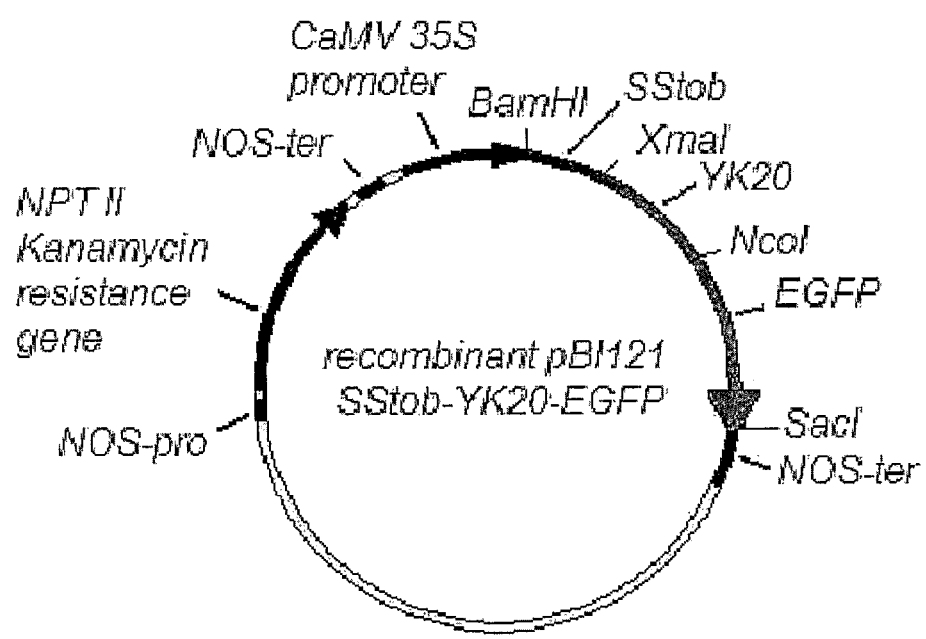
FIG. 10 illustrates a plasmid map of recombinant pBI121-SStob-YK20-EGFP. Synthetic genes SStob-YK20-EGFP (shown here), SStob-YK8-EGFP, SStob-YL20-EGFP, SStob-YL8-EGFP, SStob-FL8-EGFP, and SStob-FK9-EGFP were inserted as BamHI-SacI fragments into the pBI121 binary plant transformation vector replacing the β-glucuronidase gene as described by Shpak, E. et al. 1999. Nos-pro: nopaline synthesis promoter; NOS-ter: nopaline synthesis terminator; NPTII: Neomycin Phosotransferase II gene.

Creation of Plasmids pUC18-SStob-YK20-EGFP, pUC18-SStob-YK8-EGFP, pUC18-SStob-YL20-EGFP, pUC18-SStob-YL8-EGFP, pUC18-SStob-FL8-EGFP and pUC18-SStob-FK9-EGFP Synthetic genes YK20, YK8, YL20, YL8, FL8 and FK9 were inserted between a tobacco extensin signal sequence (SStob) and the enhanced green fluorescent protein gene (EGFP) as XmaI-NcoI fragments in the modified pUC plasmid (FIG. 9; modified pUC plasmid courtesy of Dr. Elena Shpak) (De Loose et al. 95-100; Shpak, Leykam, and Kieliszewski 14736-41; Tan L 1362-69). Plasmids modified pUC-SStob-YK20-EGFP, modified pUC-SStob-YK8-EGFP, modified pUC-SStob-YL20-EGFP, modified pUC-SStob-YL8-EGFP, modified pUC-SStob-FL8-EGFP, and modified pUC-SStob-FK9-EGFP were thus created. These plasmids were again sequenced from the 5' end using the M13 forward primer and from the 3' end using the 566asEGFP primer (Integrated DNA Technologies). Creation of plasmids pBI121-SStob-YK20-EGFP, pBI121-SStob-YK8-EGFP, pBI121-SStob-YL20-EGFP, pBI121-SStob-YL8-EGFP, pBI121-SStob-FL8-EGFP and pBI121-SStob-FK9-EGFP The synthetic genes were subcloned into the binary plant transformation vector pBI121 as BamHI-SacI fragments replacing the β-glucuronidase reporter gene to form plasmids pBI121-SStob-YK20-EGFP, pBI121-SStob-YK8-EGFP, pBI121-SStob-YL20-EGFP, pBI121-SStob-YL8-EGFP, pBI121-SStob-FL8-EGFP, and pBI121-SStob-FK9-EGFP (FIG. 10) which were then transformed to competent E. coli. Positive transformants were selected on solid LB plates supplemented with kanamycin (30 µg/ml). Plasmids were prepared from 3.5 ml liquid LB culture supplemented with 30 µg/ml kanamycin. The control plasmid pBI21-SStob-EGFP, created by Dr. Elena Shpak, was also freshly prepared. Plasmids were screened to confirm insert size by both BamHI-SacI digestion and XmaI-NcoI digestions followed by agarose gel electrophoresis (0.7% w/v). Plasmids that yielded bands of predicted size in both digestions were selected for transformation to Agrobacterium tumefaciens.

DNA Sequencing of Synthetic Genes

DNA Sequencing of Synthetic Genes Using the M13 Forward Primer

We verified insert sequences of pUC18-YK, pUC18-YL, pUC18-FL, pUC18-FK9, modified pUC-SStob-YK20-EGFP, modified pUC-SStob-YK8-EGFP, modified pUC-SStob-YL20-EGFP, modified pUC-SStob-YL8-EGFP, modified pUC-SStob-FL8-EGFP and modified pUC-SStob-FK9-EGFP by Big Dye Terminator DNA sequencing (Applied Biosystems, Foster City, Calif.) using the M13 forward primer (FIG. 11). Cycle sequencing reactions were prepared according to manufacturer's instructions and cycled using either a Stratagene-Robocyler Gradient 40-Thermal Cycler or an Applied Biosystems GeneAmp PCR system 2400. The tubes were placed in the thermocycler and incubated as in Table 1.

TABLE 1

Thermocycler program for DNA sequencing using the M13 forward primer.

| Step | Hold 1 | Hold 2 | Hold 3 | Hold 4 | Cycles |
|------|--------|--------|--------|--------|--------|
| 1 | 98° C./5 min | — | — | — | 1 |
| 2 | 98° C./30 sec | 50° C./15 sec | 60° C./4 min | — | 25 |
| 3 | — | — | — | 4° C./ 99:99 min | — |

Sequencing reactions were transferred to a sterile eppendorf tube and adjusted to 20 µl total volume with ddH$_2$O, Sequencing products were ethanol precipitated by combining 20 µl of sequencing product with 16 µl of sterile water, and 64 µl of 95% non-denatured, ACS grade ethanol. The precipitation was incubated at room temperature for 15 min then centrifuged at room temperature for 20 min at 12,000×g. The supernatants were removed and discarded. The pellets were washed with 250 µl of 70% ethanol then centrifuged 10 min at 12,000×g. Sequencing products were dried in a heat block at 90° C. for 1 min then delivered for sequencing to Dr. Morgan V is of the Automatic DNA Sequencing Facility of the Department of Environment and Plant Biology, Ohio University.

DNA Sequencing of Synthetic Genes Using the EGFP566 as Primer

The plasmids pUC18-SStob-YK20-EGFP, pUC18-SStob-YK8-EGFP pUC18-SStob-YL20-EGFP, pUC18-SStob-YL8-EGFP, pUC18-SStob-FL8-EGFP, and pUC18-SStob-FK9-EGFP were sequenced from the 3' end using the EGFP566 as primer (FIG. 11; Integrated DNA Technologies) to verify in-frame ligation of synthetic genes between SStob and EGFP. Sequencing reactions using the 566asEGFP primer were performed as described for the M13 forward primer except the annealing temperature (Table 1-Step 2, Hold 2) was lowered to 47° C.

Transformation of Agrobacterium tumefaciens and Tobacco Cells Transformation of Agrobacterium tumefaciens We transformed Agrobacterium tumefaciens (strain LBA4404) with plasmids pBI121-SStob-FK9-EGFP, pBI121-SStob-YK20-EGFP, pBI121-SStob-YK8-EGFP, pBI121-SStob-YL20-EGFP pBI121-SStob-YL8-EGFP, pBI121-SStob-FL8-EGFP, and pBI121-SStob-EGFP by the freeze-thaw method (An et al. 1-19). The plasmids were isolated from LB liquid cultures (3-5 ml) supplemented with kanamycin (30 µg/ml) using Wizard minipreps (Promega). Approximately 35-40 µl of plasmid was added directly to 100 µl of competent, frozen Agrobacterium. The mixture was thawed, then quickly frozen in N$_2$ (I). The frozen tubes were heated to 37° C. for 5 min. LB was then added to a final volume of 1 ml and the tubes were incubated at 28° C. for 2-4 h with shaking at ~100 rpm. The cells were then plated onto solid LB plates supplemented with kanamycin (30 µg/ml) and streptomycin (40 µg/ml). The plates were incubated in the dark at 28° C. for 2-3 days. Positive transformants were picked and cultured in 3.5-5 ml of LB medium having 30 µg/ml kanamycin and 40 µg/ml streptomycin at 28° C. with gentle shaking at (100-175 rpm) for about 16-20 h. The cultures were then pelleted by centrifugation (1000×g for 5-10 min) and the supernatants removed and discarded. The pellets were resuspended in 1 ml of fresh LB medium.

Transformation of Nicotiana tabacum Bright Yellow-2 (BY-2) Suspension Cultures

Tobacco cell-suspension cultures (Nicotiana tabacum, BY-2) were transformed by Agrobacterium infection as previously detailed (McCormick et al. 81-84). Untransformed tobacco BY-2 cells were cultured (500 ml in a 1 L flask) for 4-5 days on a gyrotary shaker (88-94 rpm) at room temperature in NT-1 medium. The flask of cells was removed from the shaker and the cells were settled. Tobacco cells (10 ml) were transferred under strerile conditions to empty Petri dishes. From section 2.2.1, 100 µl of the transformed Agrobacterium suspension was mixed with the cells. The cultures were parafilmed and incubated in the dark for 2-3 days at 28° C. Excess A. tumefaciens was removed from the cells by washing 3 times with 10-15 ml of sterile culture medium either NT-1 medium, Schenk and Hildebrandt medium (SH), or modified SH medium (SH*, SH sans kinentin). Washed tobacco cells were then plated on solid medium (phytagel 2 g/L in either NT-1, SH, or SH*) supplemented with kanamycin (200 µg/ml) for selection and timentin (400 µg/ml) to kill the A. tumefaciens. Tobacco transformants appeared as small bumps on the plates after 3-5 weeks. These bumps were chosen for further propagation on kanamycin and timentin supplemented plates (2-4 generations) to ensure complete eradication of the A. tumefaciens before the cells were transferred to plates having only kanamycin.

Identification of Cell Lines Expressing Synthetic Genes and Localization of Synthetic Gene Products
Fluorescence Microscopy Aliquots (5-10 ml) of suspension cultured cells were withdrawn directly from liquid cell cultures (5-20 d). Expression of EGFP in transformed cell lines was viewed using a Zeiss LSM 510 confocal laser scanning microscope set for EGFP visualization (488 nm excitation; 510 nm emission).

Plasmolysis of Transformed and Untransformed Tobacco Cells for Visualization of EGFP by Fluorescence Microscopy Suspension cultured YK20-EGFP, YK8-EGFP, YL8-EGFP, and FK9-EGFP, and SS-EGFP tobacco cells (5-20 d) were pipetted (10 ml) to 15 ml graduated tubes. The cells were centrifuged and the packed cell volume was recorded. The cells were plasmolyzed by the addition of either of 1 M potassium phosphate buffer pH 7 to a final concentration of 500 mM or 1 M mannitol to a final concentration of 750 mM. The plasmolyzed cells were viewed by fluorescence microscopy.

Verification of Transgene Insertion by PCR
Isolation of Genomic DNA from Suspension-Cultured Tobacco Cells Genomic DNA was prepared from tobacco suspension cultured cells using the DNAzol ES method (Molecular Research Center, Inc. Cincinnati, Ohio) according to manufacturer's instructions. Purity and concentration were estimated by their 260/280 nm ratio and 260 nm absorbances respectively.

PCR Amplification of Transgenes from Genomic DNA

Insertion of our transgenes SStob-YK20-EGFP and SStob-YL8-EGFP into tobacco was verified by PCR amplification using SSeq4Sen (TaOpt=43° C.; Tm=68° C.) and EGFP566 as (TaOpt=47° C.; Tm=73.1° C.) primers (FIG. 11). Master mixes were created so that each reaction (25 µl) contained 12.5 µl of 2× Promega PCR master mix (Promega), 0.125 nmol of SSeq4Sen primer, 0.125 nmol EGFP566 as primer, 10% (v/v) glycerol, and 0.14-0.21 ng of genomic template DNA. Due to a high % GC content in both primer and template DNA, a preincubation step of 98° C. for 5 min was employed. The optimized PCR program is shown in Table 2. After completion of the PCR cycles, the reactions were separated by 1% agarose gel electrophoresis, eluted from the gel, and DNA sequenced using the SSeq4Sen oligonucleotide primer.

TABLE 2

Thermocycler program for synthetic gene amplification by PCR.

| Step | Hold 1 | Hold 2 | Hold 3 | Cycles |
|---|---|---|---|---|
| 1 | 98° C./5 min | — | — | 1 |
| 2 | 98° C./30 sec | 55° C./1 min | 74° C./3 min | 25 |
| 3 | — | — | 74° C./5 min | 1 |

PCR amplicfication reactions were performed using primers SSeq4Sen and EGFP566as on an Applied Biosystems GeneAmp PCR system 2400.

Isolation and Purification of Synthetic Gene Products
Liquid Cell Culture

Figure 12:
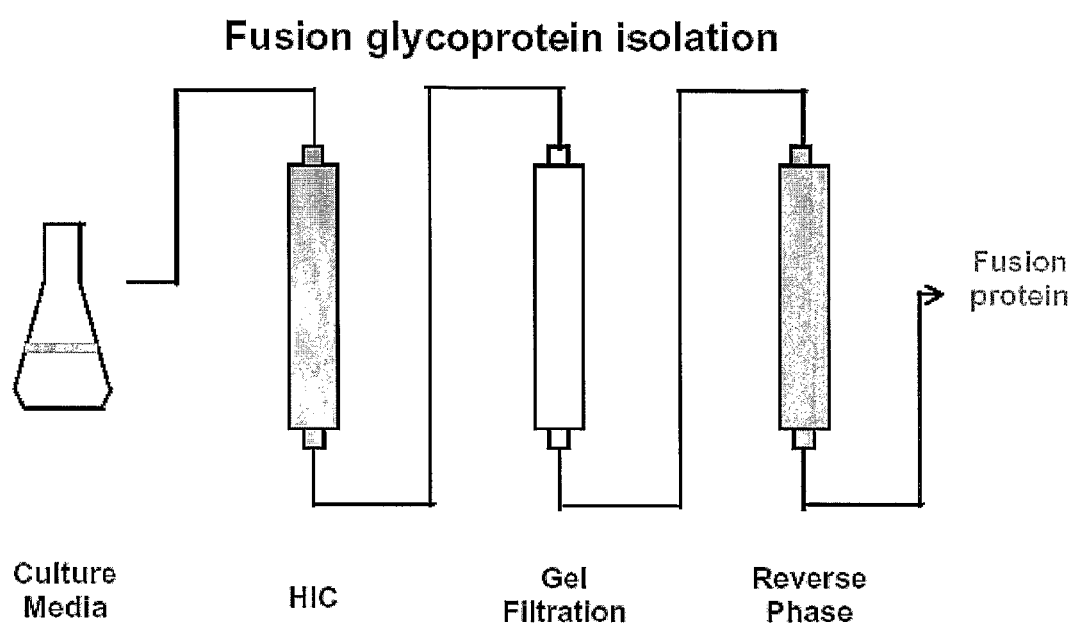
FIG. 12 is a flowchart for the isolation of EGFP fusion glycoprotein. (diagram courtesy of Dr. Li Tan). Culture medium of transformed tobacco cells was concentrated and processed by HIC, gel filtration and reversed phase HPLC.

Transformed tobacco cells were cultured in 500 ml of SH* media supplemented with kanamycin (150 µg/ml) in 1 L Erlenmeyer flasks at ambient temperatures on a gyratory shaker set to 88-94 rpm. Cells were subcultured every 14-21 days (FIG. 12).

Culture Medium Harvest

Liquid cell cultures (10-21 days) were filtered on a sintered glass funnel (Pyrex 40-60 ASTM). The culture media was collected, concentrated by rotary evaporation to 50-250 ml, then dialyzed in 3,500 Da molecular weight cut-off (MWCO) dialysis tubing (Spectrum Laboratories, Inc., Rancho Domingo, Calif.) against ddH$_2$O at 4° C. for 36 h.

Isolation of Fusion Glycoproteins by Hydrophobic Interaction Chromatography

Dialyzed medium was re-concentrated by rotary evaporation to 50-250 ml, adjusted to 2 M NaCl (aq) then centrifuged at 20,000×g for 20 min. Supernatants were loaded onto a Butyl-Sepharose 4 Fast Flow hydrophobic interaction chromatography (HIC) column (FIG. 12; 1.6 cm i.d.×40 cm, Amersham Pharmacia Biotech) equilibrated in 2 M NaCl (aq). Elution proceeded stepwise from 2 M NaCl (aq) to 1 M NaCl (aq), and finally to ddH$_2$O at flow rates of 1-2 ml/min. Visibly green fractions eluting in 1 M NaCl were collected, dialyzed against ddH$_2$O (3,500 Da MWCO or 6-8,000 Da MWCO dialysis tubing for 36 h at 4° C.; Spectrum Laboratories, Inc.) and then lyophilized.

Fractionation of Fusion Glycoproteins by Gel Filtration Chromatography

The HIC fractionated fusion glycoproteins were dissolved ~30 mg/ml in 200 mM sodium phosphate, 0.005% (w/v) sodium azide, pH 7 (Superose buffer) then chromatographed on either a semi-preparative Superose-12 column or Superose-6 gel filtration column (FIG. 12; 16 mm i.d.×500 mm, Amersham Pharmacia Biotech) equilibrated in Superose buffer, pH 7. Spectrophotometric detection was monitored at 220 nm. Flow rates were between 0.5-1 ml/min. Visibly green fractions corresponding to peaks absorbing at 220 nm were pooled and either stored at −20° C. or dialyzed, lyophilized, then stored at −20° C.

Isolation of Fusion Glycoproteins by Reversed Phase HPLC

The fusion glycoproteins isolated after gel filtration chromatography typically were directly injected onto a semi-preparative C4 reversed-phase HPLC column (FIG. 12; 10 mm i.d.×250 mm, Vydac, Hesperia, Calif.) equilibrated in 0.1% (v/v) TFA (aq) and eluted with a linear gradient to 100% end buffer (0.1% (v/v) TFA (aq) in 80% (v/v) acetonitrile) at 2 ml/min over 60 min. UV detection was monitored at 220 nm. The major peak absorbing at 220 nm corresponded to each fusion glycoprotein and was collected and lyophilized. A Hewlett-Packard series 1050 HPLC was used for purification chromatography.

Removal of the EGFP Tag by Tryptic Digestion

Fusion glycoproteins (5-100 mg) were dissolved in water to 28.6 mg/ml and heated to 100° C. for 2-3 min. Once cool, samples were diluted to 5 mg/ml in buffer containing 10 mM CaCl$_2$ (aq) and 2% (w/v) NH$_4$HCO$_3$ (aq). Trypsin was added 100:1 (w/w) substrate to enzyme. Reactions were incubated 16-24 h at room temperature with constant stirring. The digestion reactions were lyophilized, then fractionated by Superose-12 gel filtration chromatography and C4 reversed phase chromatography as described above. Peaks corresponding to YK20, YK8, YL8, and FK9 glycomodules (designated YK20, YK8, YL8, and FK9, respectively) were collected and lyophilized. The purified glycomodules were used for amino acid composition analyses and as substrates for in vitro crosslinking.

Anhydrous Hydrogen Fluoride (HF) Deglycosylation of Fusion Glycoproteins

The dried fusion glycoproteins YK20-EGFP, YK8-EGFP, and YL8-EGFP (5-10 mg) were deglycosylated with anhydrous HF as described earlier (Sanger and Lamport 66-70). Briefly, anhydrous HF containing 10% (v/v) anhydrous methanol at 0° C. was added (2-10 mg/ml) to fusion glycoprotein samples. Reactions were incubated on ice for 1 h with constant stirring then quenched by adding them to 6 volumes of ice-cold ddH$_2$O. The deglycosylated samples were dialyzed at 4° C. against ddH$_2$O, then lyophilized. Dried, deglycosylated fusion glycoproteins designated dYK20-EGFP, dYK8-EGFP, and dYL8-EGFP were isolated by analytical C4 reversed phase chromatography as described above for semi-preparative C4 HPLC, except the gradient was eluted over 40 min.

Characterization of Transgene Products
Amino Acid Composition Analyses

Glycomodules YK20, YK8, and YL8, and crosslinked YK20 (YK20XL) were analyzed for amino acid composition as described by (Bergman, Carlquist, and Jornvall 45-55). Briefly, samples were hydrolyzed at 110° C. for 18-24 h in constant boiling 6 N HCl (aq) (Pierce, Rockford, Ill.) containing 10 mM phenol (Pierce). Hydrolyzed samples were cooled to room temperature then dried under a stream of N$_2$ (g). Hydrolysates (20 µg) were derivatized with phenyl-isothiocyanate (PITC) for 15-30 min to form phenylthiocarbamyl-amino acid (PTC-aa) derivatives. The PTC-aa derivatives were separated by reversed phase HPLC on a Prodigy ODS (3) C18 analytical column (4.6 mm i.d.×150 mm, 3 µm particle size, 10 nm pore size, Phenomenex, Torrance, Calif.) with UV detection at 254 nm. The IDT quantity was determined from the same hydrolysates using a separate assay described earlier (Schnabelrauch et al. 477-89).

The amino acid composition of FK9 was determined by Dr. Joseph F. Leykam of the Macromolecular Facility at Michigan State University, East Lansing, Mich.

Partial N-Terminal Sequencing

Partial N-terminal sequences of the fusion glycoprotein FK9-EGFP and anhydrous HF deglycosylated fusion proteins dYK20-EGFP, dYK8-EGFP, and dYL8-EGFP were obtained by Joseph F. Leykam on a 477A Applied Biosystems, Inc. gas-phase sequencer by automated Edman degradation.

Colorimetric Hydroxyproline Estimation

Samples (100-1000 µg) were hydrolyzed in 6 N HCl (aq) (not more than 4 mg/ml) at 110° C. for 18-24 h. Hydrolysates were dried under N$_2$ (g) then redissolved in 0.5 ml distilled deionized water. Hydroxyproline estimation was determined by colorimetric assay as described earlier (Lamport and Miller 454-56; Lamport and Northcote 665-66).

Detection and Quantification of Isodityrosine (IDT)

Acid hydrolysates of YK20, YK8, YL8, FK9, and YK20XL were fractionated (10 μg each) on a PolyHYDROXYETHYL A column (9.4 mm i.d.×200 mm, 5 μm particle size, 10 nm pore size, PolyLC Inc., Columbia, Md.) eluted isocratically in size exclusion mode (SEC) with 50 mM formic acid at 0.8 ml/min. UV detection was monitored at 280 nm for tyrosine absorbance (Schnabelrauch et al. 477-89). IDT was partially identified by co-chromatography with an authentic external IDT standard (courtesy of Dr. Derek T. A. Lamport). A three level calibration was performed using peak areas of known amounts of the external IDT standard, from which an average molar response factor was calculated. This response factor was used to quantify IDT from peak areas of our transgene products.

Hydroxyproline-O-Glycoside Profiles of the Transgene Products

We determined the Hyp-O-glycosylation profiles of YK20-EGFP, YK8-EGFP, YL8-EGFP, and FK9-EGFP as previously described (Lamport and Miller 454-56). The fusion glycoproteins YK20-EGFP (2.20 mg), YK8-EGFP (4.10 mg), YL8-EGFP (2.25 mg), and FK9-EGFP (2.21 mg) were each dissolved at 5 mg/ml in 0.44 N NaOH (aq) and hydrolyzed at 105° C. for 18 h. Samples were cooled on ice, neutralized with ice-cold 1 M $H_2SO_4$ (aq), and then lyophilized. Dried hydrolysates were redissolved in ddH$_2$O, loaded onto a cation exchange column (6 mm i.d.×750 mm, Chromobeads C-2, Technicon) equilibrated in water, and eluted with a linear gradient to 0.5 M HCl (aq). An automated, in-line post-column hydroxyproline assay provided the detection of Hyp-glycosides at 560 nm.

Neutral Sugar Composition Analyses

The neutral sugar compositions of YK20-EGFP, YK8-EGFP, YL8-EGFP, FK9-EGFP, and YK20XL (100 μg each) were determined as alditol acetate derivatives (Albersheim et al. 340-45) using myo-inositol (50 nmol) as an internal standard as previously described (Shpak, Leykam, and Kieliszewski 14736-41). Briefly, samples containing internal standard were hydrolyzed in 200 μl of 2 N trifluoroacetic acid at 121° C. for 1 h. Hydrolysates were dried under $N_2$ (g) at 50° C. Aldehyde groups of the free aldose sugars were reduced to aiditols with sodium borohydride (NaBH$_4$ 20 mg/ml in 3 M NH$_4$OH) at room temperature for 1 h. This reaction was neutralized with glacial acetic acid, and dried thoroughly under $N_2$ (g) at 40° C. then dessicated overnight. Samples were acetylated with acetic anhydride (121° C. for 1 h.) then separated by gas chromatography (GC). GC was performed on an HP 5890 Series II GC using an HP-5 column (Crosslinked 5% PH ME Siloxane; 30 m (L) X 0.32 mm (I.D.) X 0.25 μm film thickness; Hewlett Packard, USA) programmed from 130° C. to 177° C. at a rate of 1.2° C./min then from 177 to 200° C. at a rate of 10° C./min.

Uronic Acid Estimations

Uronic acids were detected by a manual colorimetric assay (Blumenkrantz and Asboe-Hansen 484-89). The glycomodules YK20, YK8, YL8, FK9, YK20XL (100 μg) were dissolved in concentrated sulfuric acid having 12.5 M sodium tetraborate, and then cooled on ice for 5 min. The samples were hydrolyzed at 100° C. for 5 min and again cooled on ice. The m-Hydroxydiphenyl reagent (150 mg m-hydroxydiphenyl in 100 ml 0.5% (w/v) NaOH) was reacted with the samples for 5 min at room temperature and then the 520 nm absorbances were recorded. Uronic acid quantities were estimated from the 520 nm absorbances of external galacturonic acid standards.

Confirmation of Hyp-O-Arabinogalactan Polysaccharide in YL8-EGFP by Gel Filtration of Base Hydrolysates To confirm that YL8-EGFP contained O-linked Hyp arabinogalactan polysaccharide (Hyp-PS), 10.9 mg of reverse-phase purified YL8-EGFP was dissolved 5 mg/ml in 0.44N NaOH (aq) and hydrolyzed at 105° C. for 18 h. This cleaves the peptide backbone, but leaves the Hyp-O-linked glycosides intact. The hydrolysate was cooled on ice, neutralized with 1 NH$_2$SO$_4$ (aq) to pH 8.3, then lyophilized. The dried hydrolysate was dissolved in 1 ml of 20% (v/v) acetonitrile (aq) and then centrifuged 20 min at 10,300×g. Supernatants (500 μl) were separated on a Superdex-75 gel filtration column equilibrated and eluted isocratically (0.4 ml/min) in 20% (v/v) acetonitrile (aq). Fractions were collected (1 min/fraction), lyophilized, and then analyzed for hydroxyproline content (Lamport and Miller 454-56; Lamport and Northcote 665-66).

In Vitro Crosslinking of Extensin Precursors

Isolation of the pI 4.6 Extensin Peroxidase from Tomato

Untransformed Bonnie Best tomato cell suspension cultures (500 ml) were grown 10-30 days in SH* medium. The spent culture medium was filtered on sintered glass funnels, immediately shell frozen (350 ml) and lyophilized. Dry culture medium was redissolved in ice-cold ddH$_2$O to 50 ml and ultra-centrifuged at 250,000×g (60,000 rpm) for 4 h. at 10° C. to remove pectin contaminants. Supernatants were adjusted to 95% saturation with ammonium sulfate (s), gently stirred at 4° C. for 16-20 h, and then centrifuged at 27,000×g for 20 min. The pellets were dissolved in and dialyzed against 4×1 L volumes of ice-cold 20 mM sodium acetate buffer pH 6 for 18-24 h. at 4° C. in Spectra-Por 3,500 Da MWCO dialysis tubing (Spectrum Laboratories Inc.). Samples were centrifuged at 12,100×g for 15 min at 4° C. Supernatants were injected onto a preparative DEAE Sepharose Fast Flow (Amersham Pharmacia) anion exchange column (14 mm i.d.×9.6 cm) equilibrated in 20 mM sodium acetate buffer, pH 6 and eluted at a flow rate of 1 ml/min for 1 h. A linear gradient to 2M NaCl in 20 mM sodium acetate buffer, pH 6 was then applied by a gradient maker. Fractions (1 ml) were collected and assayed for peroxidase activity by 2,2'-azino-bis(3-ethylbenzthiazoline-6-sulfonic acid) (ABTS) assay as described earlier (Everdeen et al. 616-21). Active fractions were pooled and concentrated by Centricon YM-30 centrifugal filter devices (Millipore, USA). Retentates were pooled, adjusted to 10% (v/v) glycerol, frozen with $N_2$ (l) in 100-250 μl aliquots, and stored at (–80)° C.

Purification of pI 4.6 Extensin Peroxidase from Tomato by HPLC

Anionic peroxidase fractions from preparative DEAE anion exchange chromatography were further separated by normal-phase ion exchange HPLC on a DEAE-5PW column (Tosohaas, 7.5 mm i.d.×750 mm). The column was equilibrated in 20 mM sodium acetate pH 6 and eluted by a linear gradient to 500 mM NaCl (aq) in 20 mM sodium acetate pH 6 over 100 minutes with a flow rate of 1 ml/min. Heme group absorbance, typical of class III plant peroxidases (Welinder et al. 6063-81), was monitored at 405 nm.

Quantification of Peroxidase Activity by 2,2'-azino-bis(3-ethylbenzthiazoline-6-sulfonic Acid) (ABTS) Assay Peroxidase activity was quantified by ABTS assay as described earlier (Everdeen et al. 616-21; Schnabelrauch et al. 477-89), whereby 12 ng of peroxidase will produce an absorbance change of 1 $A_{405\ nm}$ unit per minute.

In Vitro Crosslinking of P3 Glycomodules with Tomato Extensin Peroxidase

Tomato P1 extensin was isolated as described earlier for use as a positive crosslinking control (Smith et al. 1021-30;

Smith, Muldoon, and Lamport 1233-39). Reversed phase HPLC purified glycomodules YK20, YK8, YL8, and FK9 and native tomato P1 extensin were used as substrates for in vitro crosslinking reactions. Extensin substrate stock solutions (6 mg/ml) were prepared by diluting 10 mg/ml substrates in ddH$_2$O with McIlvaine buffer pH6. Crosslinking reactions were performed at room temperature by combining substrate (3 mg/ml), extensin peroxidase enzyme (1 ng per 60 μg of substrate), and H$_2$O$_2$ (60 μM). Reaction time was initiated upon addition of H$_2$O$_2$. The stopping reagent (50 mM 2-mercaptoethanol) was added prior to H$_2$O$_2$ in time zero reactions to prevent crosslinking from occurring. Reactions were stopped by the addition of 50 mM 2-mercaptoethanol (16.7 mM final concentration) after specified times.

Detection of in vitro crosslinking and rate estimations were provided by analytical Superose-6 gel filtration chromatography eluted isocratically in pH 7 Superose buffer (Amersham Pharmacia; 0.75 ml/min; OD 220 nm detection). Crosslinking rates were calculated by the decrease in peak area of the monomer after 1 min of incubation versus an equal amount of the time zero reaction using the first order rate equation (Schnabelrauch et al. 477-89). Rates were expressed as the amount of substrate crosslinked (μg) per sec (Schnabelrauch et al. 477-89).

Detection of Extensin Peroxidase Activity in Tobacco Cell Suspension Cultures

Untransformed tobacco BY-2 suspension cultured cells were grown 10 days in NT-1 culture medium to 17% PCV. The cells (100 ml) were filtered on a sintered glass funnel, washed with 1.25 L of water, and then eluted with 500 ml of 1 M KCl (aq) in 20 mM sodium acetate buffer, pH 6. This salt-eluted fraction was designated (E2). Spent culture medium (350 ml) was lyophilized then redissolved to 50 ml with ice-cold water. This crude medium fraction was designated (E1). Subsequent steps were kept at or below 4° C. The salt-eluate E2 sample was then dialyzed (24-36 h; 4° C.; 3,500 Da MWCO tubing) against 20 mM sodium acetate buffer, pH 6. A 250 ml aliquot of the dialyzed E2 was lyophilized, and then redissolved to 1 ml with water. Enzyme activity was estimated by ABTS assay. The E1 and E2 samples were then examined for extensin crosslinking.

In Vitro Crosslinking with Crude Cationic Tomato Peroxidases

Crude tomato culture medium was prepared as described for pI 4.6 extensin peroxidase preparation. The preparative DEAE void fraction (non-binding) was collected. An aliquot (10-15 ml) was concentrated to 3.2 ml using Centricon YM-30 centrifugal filter devices (Millipore). The concentrated void peroxidases were adjusted to 10% (v/v) glycerol and then stored at −80° C. The void peroxidases were quantified by ABTS assay then tested for in vitro crosslinking. Crosslinking reactions were incubated with substrates (3 mg/ml), enzyme (1.7 ng/60 μg substrate), and H$_2$O$_2$ (60 μM) for 0 and 30 min. The reactions were separated by gel filtration on an analytical Superose-6 column (Amersham Pharmacia) eluted at 0.5 ml/min with UV detection at 220 nm.

Analysis of Crosslinked Extensin Products
Isolation of Diisodityrosine (di-IDT) From Untransformed Tomato Cell Walls
Isolation of Cell Walls Untransformed Bonnie Best tomato cell suspension cultures were filtered on a sintered glass funnel. The cell walls were isolated as described earlier (Lamport 151-218; Lamport and Northcote 52P).

Acid Hydrolysis of Untransformed Tomato Cell Walls

In a closed reflux apparatus, 1.55 g of untransformed tomato cell walls were added to 465 ml of 6 N HCl (aq) containing 10 mM phenol (Pierce). The hydrolysis vessel was purged of air by vacuum then flushed with N$_2$ (g). The cell walls were refluxed for 24 h then cooled. The hydrolysate was concentrated by rotary evaporation then dried completely under a stream of N$_2$ (g).

Strong Cation Exchange Chromatography of Cell Wall Hydrolysates

The cell wall hydrolysate was redissolved in 100 ml of ddH$_2$O then chromatographed on Whatman P11 strong cation exchange column eluted by gravity as described earlier (Brady, Sadler, and Fry 323-27). Fractions 0-9 were collected (100 ml each) and concentrated to dryness by rotary evaporation. Fractions 0-9 were each redissolved in 1 ml of ddH$_2$O. A 1 μl aliquot of fractions 0-9 was spotted on Whatman 3 mM chromatography paper and examined under UV light (254 nm). The spots were then exposed to NH$_4$OH vapor and reexamined under 254 nm light.

Paper Chromatography

Paper chromatography was performed as previously described (Brady, Sadler, and Fry 323-27). An authentic diIDT standard was a gift from Dr. Stephen C. Fry of the University of Edinburgh and was chromatographed to detect diIDT in fraction 7.

Size Exclusion Chromatography

Fraction 7 (500 μl) from P11 cation exchange chromatography was filtered with Millipore spin filters (0.45 μm pore size; filter type HV; Nihon Millipore Kogyo K.K. Japan). The filtrate (250 μl per injection) was fractionated on a PolyHYDROXYETHYL A column (9.4 mm i.d.×200 mm; 5 μm particle size, 20 nm pore size, PolyLC Inc.) eluted isocratically in size exclusion mode (SEC) with 50 mM formic acid at 0.8 ml/min and UV detection at 280 nm (Schnabelrauch et al. 477-89). Six fractions, designated SEC1 F1-6, were collected, checked for blue fluorescence as described in section 2.7.1.3, and then lyophilized.

SEC1 F4 was redissolved in 0.1 ml of ddH$_2$O and refractionated by SEC on a PolyHYDROXYETHYL A column (9.4 mm i.d.×200 mm; 5 μm particle size, 10 nm pore size, PolyLC Inc.; 10 μl per injection) as described above (Schnabelrauch et al. 477-89). Five fractions, designated SEC2 F1-5, were collected, checked for blue fluorescence, and then lyophilized.

Reverse-Phase HPLC Purification of Diisodityrosine

Diisodityrosine (my diIDT) was purified from SEC2 F4 by reversed phase chromatography on a Waters Spherisorb ODS-2 C18 column (4.6 mm i.d.×250 mm; 5 μm particle size; Alltech Associates, Inc., Deerfield, Ill.). Briefly, SEC2 F4 was redissolved in 50 μl of ddH$_2$O and injected onto the C18 column equilibrated in ddH$_2$O. The column was washed with water for 15 min then eluted at 0.8 ml/min with a linear gradient to 60% (v/v) acetonitrile (aq) over 25 min. A peak absorbing at 280 nm eluted at 24.8 min was collected. Further fractionation of this peak on the 10 nm pore size Polyhydroxyethyl A column confirmed its retention time at 10.4 min.

Isolation of YK20 Crosslinking Amino Acids
In Vitro Crosslinking of YK20 for Isolation of Crosslinking Amino Acids YK20 (20 mg) was crosslinked overnight under the conditions described in section 2.6.4 with pI 4.6 extensin peroxidase isolated from tomato suspension cultures. The reaction was stopped with 50 mM 2-mercaptoethanol then lyophilized. The dried crosslinking reaction was dissolved in a minimal volume of water then centrifuged at 10,300×g for 20 min. The insoluble pellet (YK20XL) was washed with ddH$_2$O until the conductivity of the supernatants was equal to that of water.

Acid Hydrolysis of YK20XL and YK20 for the Isolation of Crosslinking Amino Acids The YK20XL and YK20 samples (2.2 mg and 1 mg respectively) were dissolved to 2 mg/ml in 6N HCl with 10 mM phenol in sealed glass conical vials and then hydrolyzed for 20 h. at 110° C. in a heating block. Hydrolysates were dried under $N_2$ (g) then resuspended in 100 µl dd$H_2O$, Size Exclusion Chromatography for the Purification of the Crosslinking Amino Acids Hydrolysates of YK20XL and YK20 were fractionated by SEC on a PolyHYDROXYETHYL A column (9.4 mm id X 200 mm; 5 µm particle size; 10 nm pore size; PolyLC) as previously described. UV detection was monitored at 280 nm for tyrosine (and tyrosine derivative) absorbance. The peaks were collected and lyophilized.

Molecular Mass Determination of the YK20 Crosslinking Amino Acid by MALDI TOF Mass Spectrometry The unknown crosslinking amino acid candidate was identified by MALDI-TOF mass spectrometry by Dr. Michael Hare at Oregon State University.

Identification of the Crosslinking Amino Acid Unknown by 1-D $^1$HNMR

The unknown crosslinking amino acid from hydrolysate of YK20XL was characterized by 1-D $^1$HNMR techniques by Dr. Li Tan of Ohio University.

Results

Synthetic Gene Construction

The synthetic genes SStob-YK20-EGFP, SStob-YK8-EGFP, SStob-YL20-EGFP, SStob-YL8-EGFP, SStob-FK9-EGFP, and SStob-FL8-EGFP were assembled from oligonucleotide primers and sequenced (Lewis et al. 400-06; Shpak 179; Shpak, Leykam, and Kieliszewski 14736-41; Tan L 1362-69) (FIG. 13). The synthetic gene SStob-EGFP was kindly donated by Dr. Elena Shpak. These synthetic genes were inserted into the binary plant transformation vector pBI121 under the promotion of the CaMV 35 S constitutive promoter forming plasmids pBI121-SStob-YK20-EGFP, pBI121-SStob-YK8-EGFP, pBI121-SStob-YL20-EGFP, pBI121-SStob-YL8-EGFP, pBI121-SStob-FK9-EGFP, pBI121-SStob-FL8-EGFP, and pBI121-SStob-EGFP (Shpak, Leykam, and Kieliszewski 14736-41).

Transformation of A. tumefaciens and Tobacco Cells with Synthetic Genes

Agrobacterium tumefaciens was transformed with plasmids pBI121-SStob-YK8-EGFP, pBI121-SStob-YK20-EGFP, pBI121-SStob-YL8-EGFP, pBI121-SStob-YL20-EGFP, pBI121-SStob-FL8-EGFP, pBI121-SStob-FK9-EGFP, and pBI-SStob-EGFP (McCormick et al. 81-84). Tobacco BY-2 cell suspension cultures were subsequently transformed with these synthetic genes by A. tumefaciens infection yielding cell lines designated NtYK20-EGFP, NtYK8-EGFP, NtYL20-EGFP, NtYL8-EGFP, NtFK9-EGFP, NtFL8-EGFP, and NtSS-EGFP.

Verification of Synthetic Gene Insertion by PCR

Figure 14:
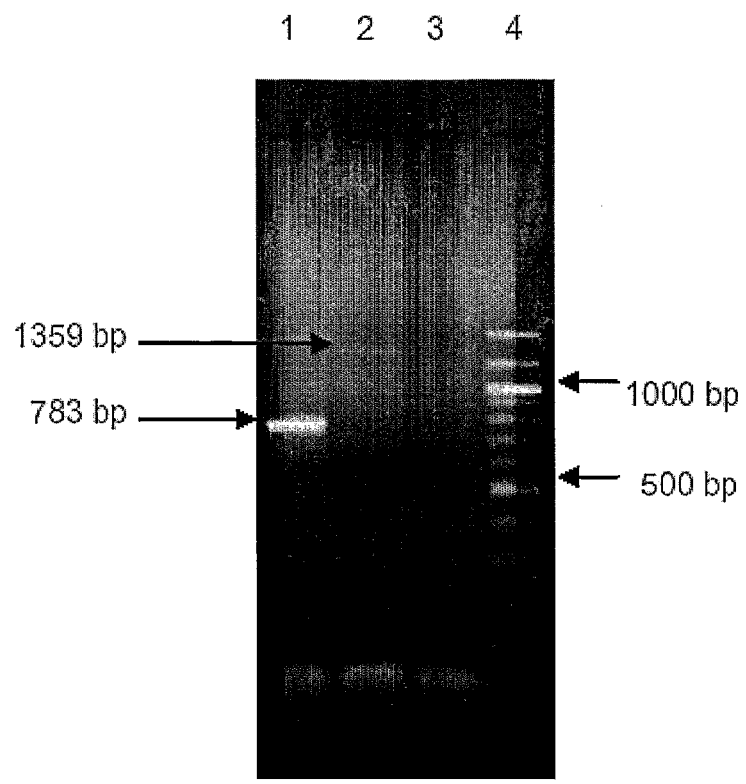
FIG. 14 shows PCR amplification of genomic DNA from cell lines NtYK20-EGFP and NtYL8-EGFP. Insertion of the synthetic genes SStob-YK20-EGFP and SStob-YL8-EGFP into the tobacco genome was verified by PCR amplification with oligonucleotide primers complimentary to the antisense strand of SStob and the sense strand of EGFP. Bands at 783 bp and 1359 bp from lanes 1 and 2 respectively were eluted from the gel and sequenced. Lane 1: SStob-YL8-EGFP PCR product; Lane 2: SStob-YK20-EGFP PCR product; Lane 3: untransformed tobacco PCR product (control); Lane 4: 100 bp ladder.
Figure 15:
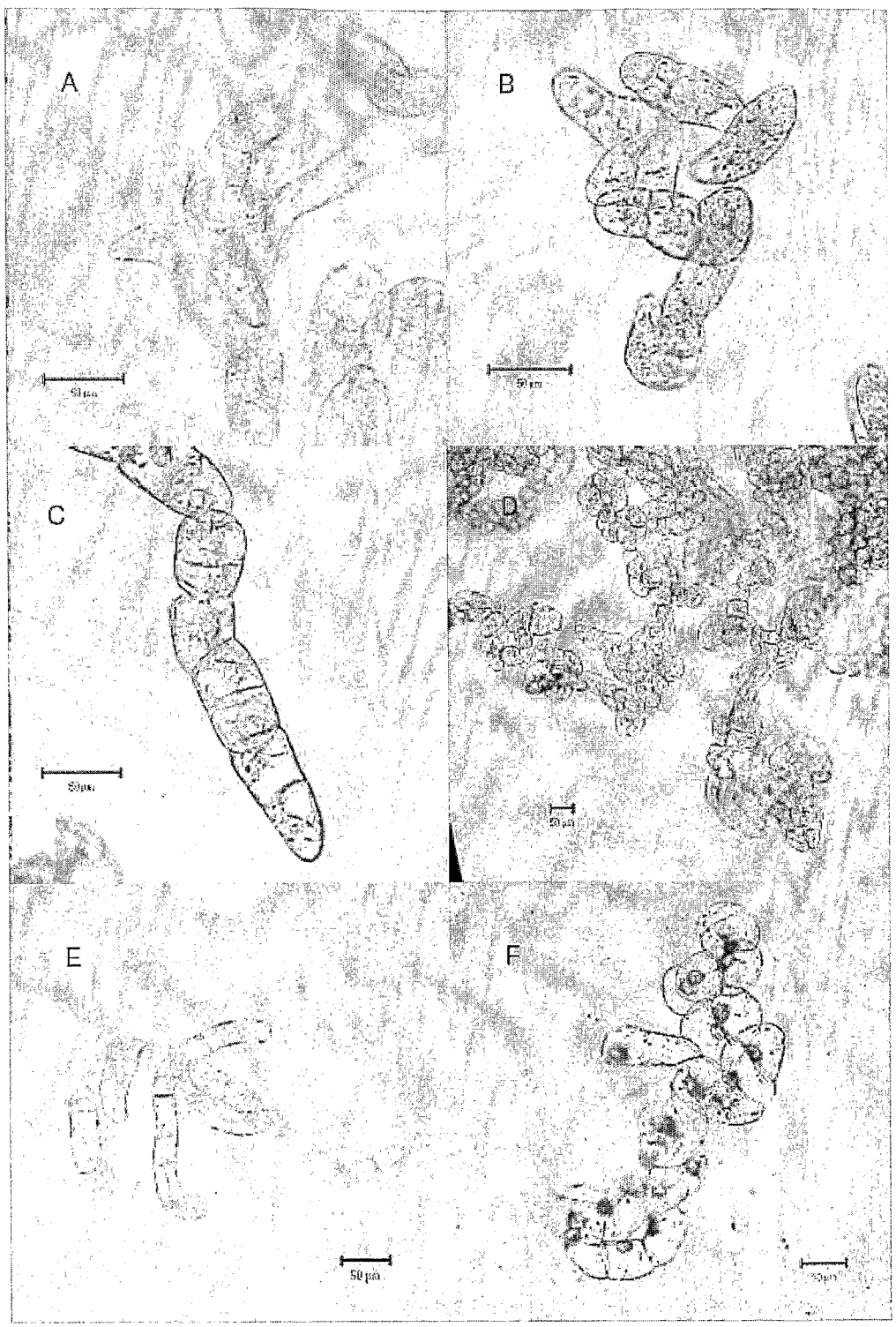
FIG. 15 is a visualization of cell lines (A) NtYK20-EGFP, (B) NtYK8-EGFP, (C) NtYL8-EGFP, (D) NtFK9-EGFP, (E) uTob, and (F) NtSS-EGFP by fluorescence microscopy. Slides shown here are an overlay of the laser scanned image (exc. 488 nm, emm. 510 nm) and the transmitted light image.

Insertion of the synthetic genes SStob-YK20-EGFP and SStob-YL8-EGFP into tobacco cells was verified by PCR of genomic DNA with oligonucleotide primers complimentary to SStob and EGFP (FIG. 14). Synthetic gene expression of YK20-EGFP, YK8-EGFP, YL8-EGFP, and FK9-EGFP The transformed cell lines NtYK20-EGFP, NtYK8-EGFP, NtYL8-EGFP, NtFK9-EGFP, NtSS-EGFP demonstrated EGFP expression when viewed by fluorescence microscopy (FIG. 15). Untransformed tobacco (uTob) cells were viewed as a control. Although NtSS-EGFP and NtYL20-EGFP- demonstrated EGFP expression when viewed by fluorescence microscopy (not shown), no fusion glycoprotein was able to be isolated from the culture medium of these cell lines. The FL8-EGFP cell line was never observed to exhibit green fluorescence (not shown).

Cellular Localization of YK20-EGFP to the Cell Wall

The YK20-EGFP, SS-EGFP, and uTob cells were plasmolyzed to determine the cellular localization of their respective transgene products. The fluorescence in YK20-EGFP cells was localized to the cell wall, with a concentration in the crosswall, whereas SS-EGFP was localized to intracellular compartments (FIG. 16). Plasmolysis of YK8-EGFP, YL8-EGFP, or FK9-EGFP cells did not demonstrate visible fluorescence in the cell wall (not shown). The YK20-EGFP fusion proteins remained with the cell wall after plasmolysis with 500 mM potassium phosphate pH 7 (FIG. 16E).

Figure 17:
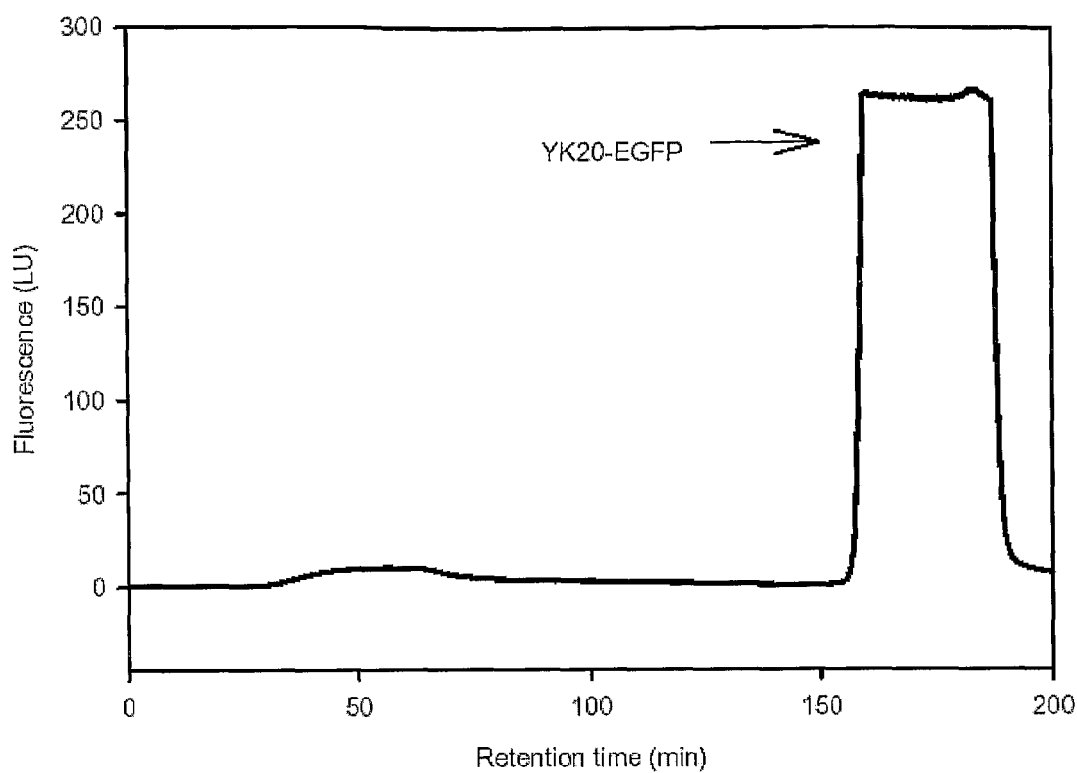
FIG. 17 shows a fractionation of transgenic NtYK20-EGFP culture medium by HIC. Concentrated and desalted NtYK20-EGFP (shown here), NtYK8-EGFP, NtYL8-EGFP, and NtFK9-EGFP culture media were loaded onto a HIC column and eluted stepwise from 2 M NaCl to 1 M NaCl and then to water. The eluate was monitored by in-line fluorescence detection (exc. 488 nm, emm. 510 nm; Hewlett Packard, USA). A single green peak eluted in 1 M NaCl.

Isolation of the Fusion Glycoproteins YK20-EGFP, YK8-EGFP, YL8-EGFP and FK9-EGFP Transformed YK20-EGFP, YK8-EGFP, YL8-EGFP, and FK9-EGFP cells demonstrated EGFP secretion into the culture medium. Concentrated culture medium was fractionated by HIC (FIG. 17). Fluorescent green fractions were collected, desalted by dialysis, and then lyophilized.

To further purify the HIC-fractionated YK20-EGFP, YK8-EGFP, YL8-EGFP, and FK9-EGFP fusion glycoproteins, gel filtration chromatography was performed using either a Superose-6 or 12 column. Chromatographs typically showed two fluorescent green peaks absorbing at 220 nm. The larger molecular weight peak corresponded to the P3-EGFP fusion glycoprotein and the smaller for cleaved EGFP (not shown).

Figure 18:
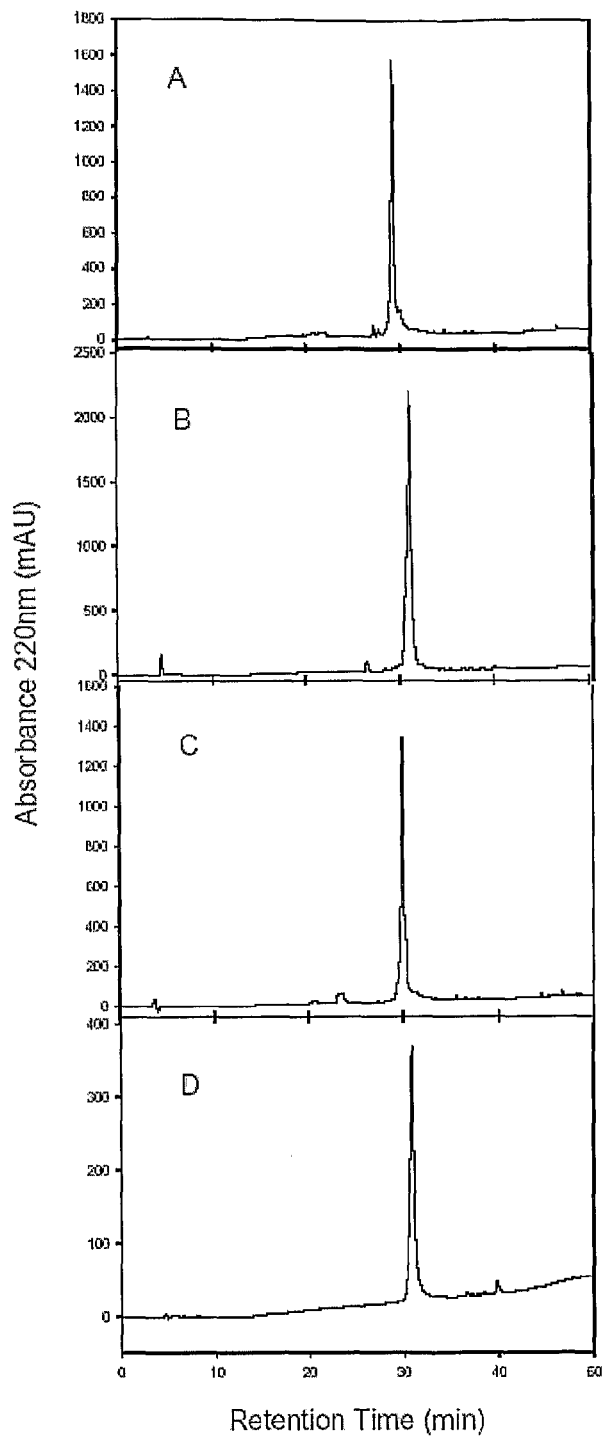
FIG. 18 shows purification of the YK20-EGFP, YK8-EGFP, YL8-EGFP, and FK9-EGFP fusion glycoproteins by C4 reversed phase HPLC. (A) YK20-EGFP (300 µg), (B) YK8-EGFP (200 µg), (C) YL8-EGFP (200 µg), and (D) FK9-EGFP (45 µg) were injected onto an analytical C4 reversed phase HPLC column. The fusion glycoproteins eluted between 28 and 32 min (58% and 68% end buffer).

The YK20-EGFP, YK8-EGFP, YL8-EGFP, and FK9-EGFP fusion glycoproteins eluted between 55-65% end buffer as single peaks upon C4 reversed phase HPLC fractionation (FIG. 18). Typically, the fusion glycoprotein yields ranged from 3-27 mg/l medium for YK20-EGFP, from 4-7 mg/l for YK8-EGFP, and from 6-23 mg/l for YL8-EGFP. Yields for FK9-EGFP were lower at 0.1 to 3.3 mg/l.

Isolation of the Glycomodules YK20, YK8, YL8, and FK9

Figure 19:
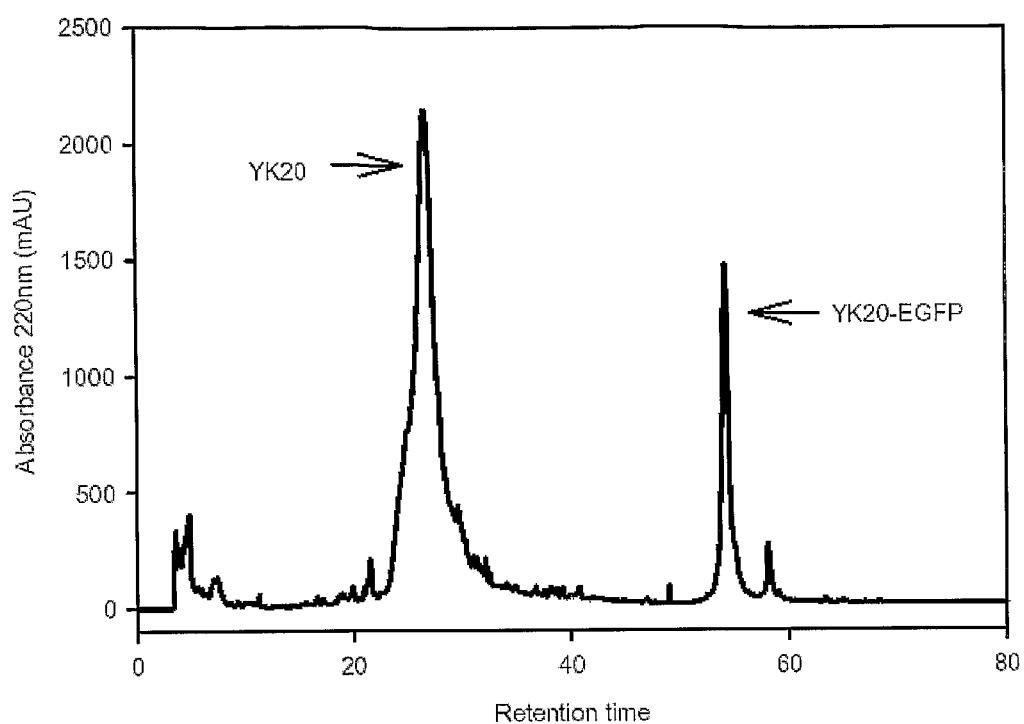
FIG. 19 shows the isolation of glycomodules YK20, YK8, YL8, and FK9 by C4 reversed phase HPLC. Glycomodules YK20, YK8, YL8, and FK9 eluted between 30-40% end buffer, prior to their respective undigested fusion glycoproteins.

Fractionation of tryptic digestions of YK20-EGFP, YK8-EGFP, YL8-EGFP and FK9-EGFP by gel filtration followed by reversed phase HPLC yielded pure glycomodules designated YK20, YK8, YL8, and FK9 (FIG. 19). Trypsin was not able to cleave lysine residues within the P3 modules, presumably due to the protection of the peptide backbone by the Hyp-O-oligoarabinosides (Lamport 1155-63; Smith et al. 1021-30; Stafstrom and Staehelin 242-46).

Figure 20:
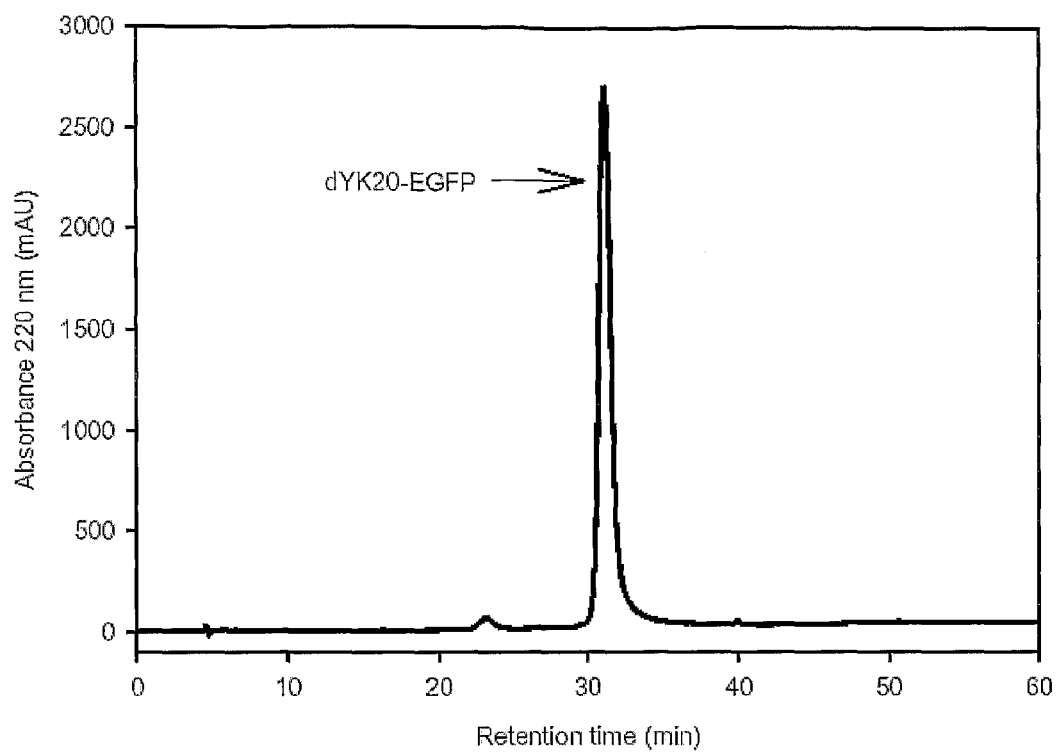
FIG. 20 shows a C4 reversed phase HPLC purification of dYK20-EGFP. Deglycosylated YK20-EGFP (200 µg) was purified on a C4 analytical column. The dYK20-EGFP fusion protein showed a slightly increased retention time (~69% end buffer) compared to the respective fusion glycoprotein.

Deglycosylation of the Fusion Glycoproteins YK20-EGFP, YK8-EGFP, and YL8-EGFP by Anhydrous Hydrogen Fluoride Solvolysis Deglycosylated fusion proteins were purified by C4 reversed phase HPLC (FIG. 20). Protein weight recoveries were recorded to estimate the mass of carbohydrate removed (Table 3). FK9-EGFP was not deglycosylated by anhydrous HF solvolysis.

TABLE 3

Estimated percent weight carbohydrate of YK20-EGFP, YK8-EGFP, and YL8-EGFP.

| Sample | Protein wt. recovery (%) | Carbohydrate wt. recovery (%) |
|---|---|---|
| YK20-EGFP | 42 | 68 |
| YK8-EGFP | 49 | 51 |
| YL8-EGFP | 48 | 52 |

Protein weight recoveries were recorded after HF deglycosylation, from which the percent carbohydrate was estimated.

Amino Acid Composition Analyses of the YK20, YK8, YL8, and FK9 Glycomodules

Figure 21:
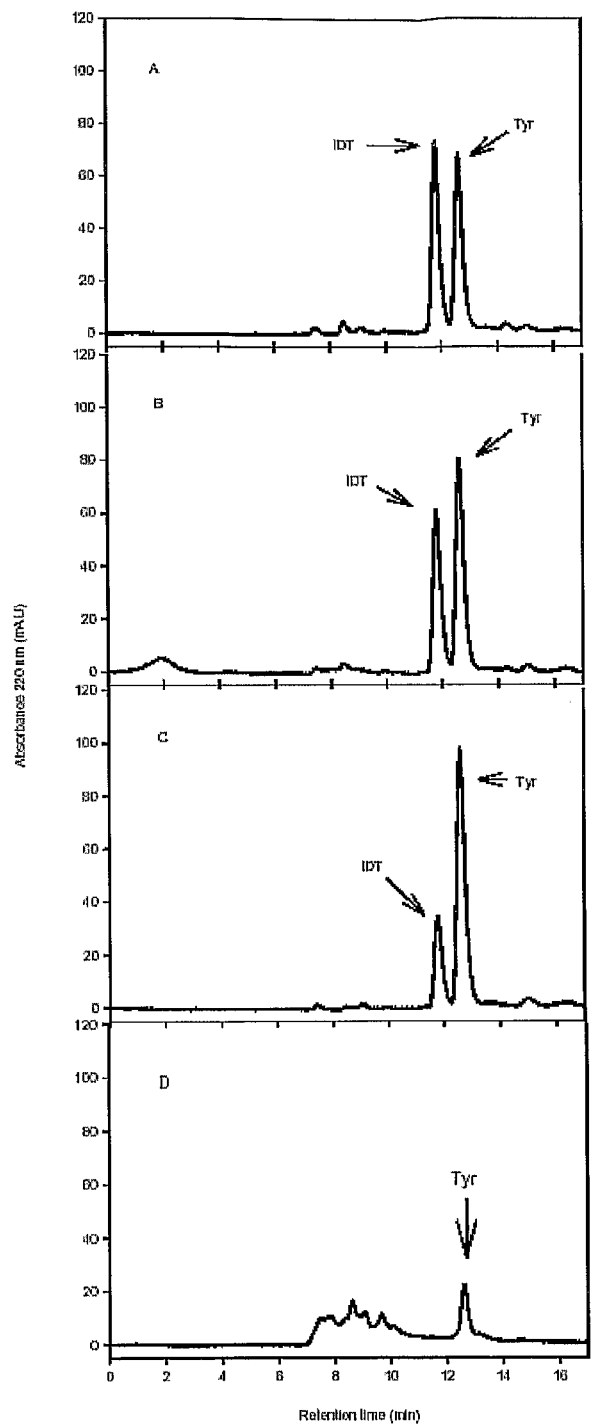
FIG. 21 demonstrates an examination of acid hydrolysates of (A) YK20, (B) YK8, (C) YL8 glycomodules and (D) FK9-EGFP fusion glycoprotein for IDT. Acid hydrolysates (10 µg each) were fractionated by SEC. The YK20, YK8, and YL8 glycomodules contained IDT whereas FK9-EGFP did not.

Amino acid compositions of the purified glycomodules YK20, YK8, YL8 and FK9 were determined (Table 4). All of the samples exhibited nearly complete hydroxylation of proline residues. Isodityrosine (IDT), a diphenyl ether-linked tyrosine dimer (FIG. 1) was observed in the hydrolysates of YK20, YK8, and YL8, but not in FK9 (FIG. 21).

TABLE 4

Amino acid compositions of the glycomodules YK20, YK8, YL8, and FK9.

| Amino Acid | Amino Acid Composition (mol %) | | | | | | | |
|---|---|---|---|---|---|---|---|---|
| | YK20 | | YK8 | | YL8 | | FK9 | |
| | Protein | Gene | Protein | Gene | Protein | Gene | Protein | Gene |
| Hyp | 59.8 | 0 | 60 | 0 | 56 | 0 | 52.5 | 0 |
| Pro | 0 | 55.4 | 0 | 54.1 | 0 | 54.1 | 0 | 55.3 |
| Ser | 18.2 | 19 | 18 | 19.3 | 20 | 19.3 | 17.8 | 19.5 |
| Tyr | 9 | 18.3 | 9 | 17.8 | 13 | 17.8 | 0 | 0 |
| 1/2IDT | 8.7 | 0 | 8 | 0 | 5 | 0 | 0 | 0 |
| Phe | 0 | 0 | 0 | 0 | 0 | 0 | 21 | 17.5 |
| Lys | 4.3 | 6.4 | 5 | 6.7 | 0 | 0.7 | 7 | 6.5 |
| Leu | 0 | 0 | 0 | 0 | 6 | 6 | 0.6 | 0 |
| Thr | 0 | 0.3 | 0 | 0.7 | 0 | 0.7 | 0 | 0 |
| Met | 0 | 0.3 | 0 | 0.7 | 0 | 0.7 | 0.9 | 0.6 |
| Val | 0 | 0.3 | 0 | 0.7 | 0 | 0.7 | 0.2 | 0.6 |
| Total | 100 | 100 | 100 | 100 | 100 | 100 | 100 | 100 |

Actual compositions (Protein) are compared to the deduced compositions (Gene) from synthetic gene translations.

Partial N-Terminal Sequencing of dYK20-EGFP, dYK8-EGFP, dYL8-EGFP and FK9-EGFP by Automated Edman Degradation The partial N-terminal sequences of dYK20-EGFP, dYK8-EGFP, dYL8-EGFP and FK9-EGFP matched those predicted from the gene sequences (Table 5). The two terminal Arg residues of dYK20-EGFP, dYK8-EGFP, and dYL8-EGFP fusion proteins were a result of restriction site design. Originally, YK20-EGFP and YL8-EGFP were sent for sequencing, but the sequences did not exactly match those predicted from their genes. Deglycosylation of these fusion glycoproteins prior to N-terminal sequencing, however, yielded their predicted sequences.

TABLE 5

Partial N-terminal sequences of dYK20-EGFP, dYK8-EGFP, dYL8-EGFP, and FK9-EGFP.

| Fusion protein | Partial N-terminal sequence (SEQ ID NOS 72-75) |
|---|---|
| dYK20-EGFP | RRPSOOOOYYYKSOOOOSOS |
| dYK8-EGFP | RROSOOOOYYYKSOOOOSOS |
| dYL8-EGFP | RRPSOOOOYYYLSOOOOSOS |
| FK9-EGFP | SOOOOSOSOOOOFFFKSOOOOSOSOOOO |

Hyp-O-Glycoside Profiles of the YK20-EGFP, YK8-EGFP, YL8-EGFP and FK9-EGFP Fusion Glycoproteins All of the fusion glycoproteins showed greater than 82% of the total Hyp residues possessed O-linked tri or tetraoligoarabinosides (Table 6) as predicted by the Hyp Contiguity Hypothesis (Kieliszewski and Lamport 157-72). With the exception of YL8-EGFP, Hyp-PS was not detected in the fusion glycoproteins.

TABLE 6

Hyp-O-glycoside profiles of the YK20-EFGP, YK8-EFGP, YL8-EGFP and FK9-EGFP fusion glycoproteins.

| Hyp-Glycoside[a] | Percentage of total hydroxyproline | | | |
|---|---|---|---|---|
| | YK20-EGFP | YK8-EGFP | YL8-EGFP | FK9-EGFP |
| Hyp-PS | 0 | 0 | 3 | 0 |
| Hyp-Ara$_4$ | 56 | 56 | 55 | 42 |
| Hyp-Ara$_3$ | 32 | 31 | 27 | 40 |
| Hyp-Ara$_2$ | 4 | 4 | 6 | 5 |
| Hyp-Ara$_1$ | 5 | 5 | 4 | 5 |
| NG-Hyp | 3 | 4 | 5 | 8 |

EGFP does not contain Hyp and is not glycosylated (Shpak E. et al. 1999).
[a]Hyp-PS, Hyp polysaccharide; Hyp-Ara$_n$, Hyp-arabinoside$_{1-4}$; NG-Hyp, non-glycosylated Hyp.

Neutral Sugar Composition Analyses of the Fusion Glycoproteins YK20-EGFP, YK8-EGFP, YL8-EGFP, and FK9-EGFP At least 84% of the neutral sugar carbohydrate attached to our fusion glycoproteins was arabinose (Table 7). Significant amounts of galactose were observed in all of the fusion glycoproteins indicating the presence of monogalactosyl-serine (Ser-O-gal). A lower ratio of arabinose:galactose was observed for YL8-EGFP. Essentially no uronic acids were detected in any of the fusion glycoproteins or glycomodules. Thus, we estimated that YK20-EGFP was 39% wt carbohydrate (CHO), YK8-EGFP was 48% wt. CHO, YL8-EGFP was 45% wt. CHO, and FK9-EGFP was 32% wt. CHO.

TABLE 7

Neutral sugar compositions of the YK20-EGFP, YK8-EGFP, YL8-EGFP, and FK9-EGFP fusion glycoproteins.

| Glycosyl residue | Glycosyl Composition (mol %) | | | |
|---|---|---|---|---|
| | YK20-EGFP | YK8-EGFP | YL8-EGFP | FK9-EGFP |
| Arabinose | 90 | 91 | 84 | 91 |
| Galactose | 8 | 7 | 12 | 9 |
| Rhamnose | 1 | 1 | 2 | 0 |
| Xylose | 0 | 0 | 1 | 0 |
| Glucose | 1 | 1 | 1 | 0 |

EGFP is not glycosylated (Shpak, E. et al 1999).

Detection of Hyp-PS in the YL8-EGFP Fusion Glycoprotein

Figure 22:
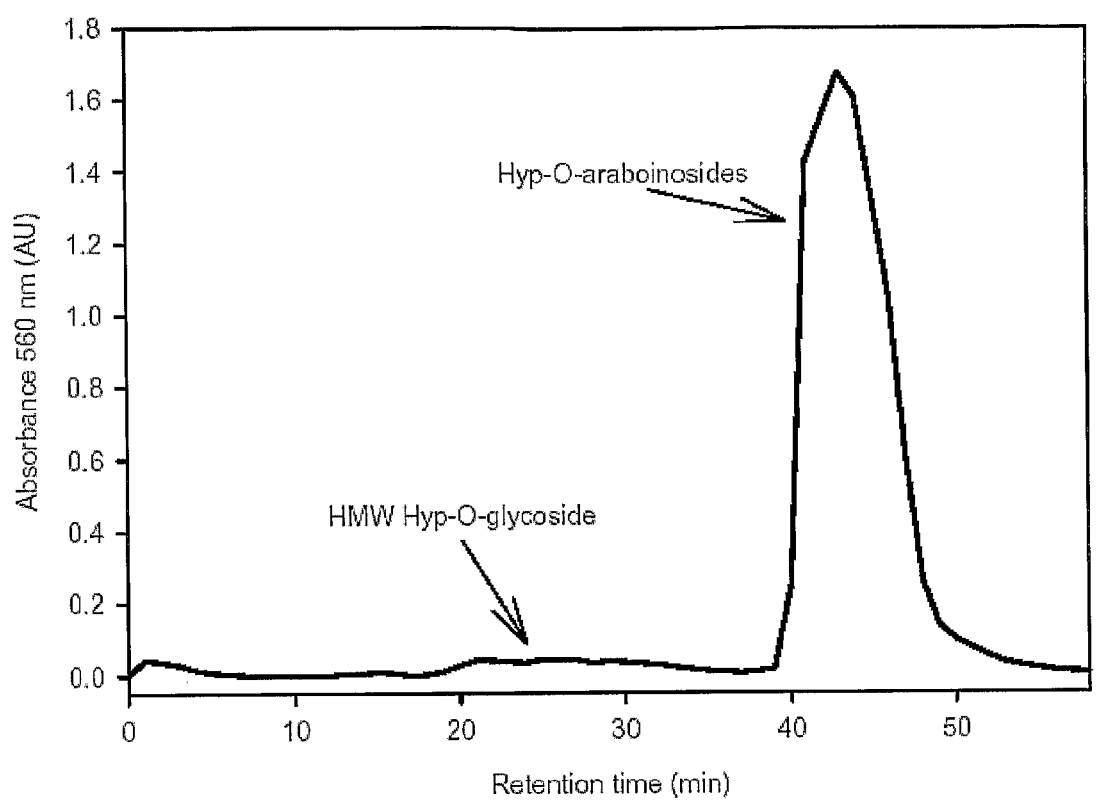
FIG. 22 shows the detection of Hyp-PS in base hydrolysates of YL8-EGFP fractionated by Superdex-75 gel filtration chromatography. A HMW Hyp-O-glycoside peak was observed in the hydrolysate of YL8-EGFP eluting between 18 and 38 min. This confirmed the presence of Hyp-PS attachment to YL8-EGFP.

Base hydrolysis followed by gel filtration chromatography indicated a high molecular wt. (HMW) Hyp-O-glycoside occurred in YL8-EGFP and comprised approximately 5.2% of the total Hyp as compared to 3% of the total Hyp calculated from the Hyp-O-glycoside profile (FIG. 22). This confirmed that YL8-EGFP contains a small amount of Hyp-PS.

Estimated Molecular Mass of the Fusion Glycoproteins YK20-EGFP, YK8-EGFP, YL8-EGFP, and FK9-EGFP Molecular masses of YK20-EGFP, YK8-EGFP, YL8-EGFP, and FK9-EGFP were estimated from the Hyp-O-glycoside data, the neutral sugar composition data, and the deduced amino acid composition data. EGFP contributes 26,924 Da to each fusion glycoprotein. The weight contributions of the arabinooligosaccharides were estimated from the Hyp-O-glycoside profiles (Table 8). Galactose was estimated from the neutral sugar compositions and the weight contribution of the arabinooligosaccharides (Table 9). The protein weight contributions of the modules were predicted from the deduced amino acid sequence (Table 10; as shown in FIG. 13). The sum of these values yielded predicted molecular weights of each fusion glycoprotein (Table 11).

TABLE 8

Weight contribution of the arabinooligosaccharides of YK20-EGFP.

| YK20-EGFP | % of Hyp | Number/molecule | MW of Arabinosides | Daltons |
|---|---|---|---|---|
| Hyp-(Ara)₄ | 56 | 101 | 528 | 53222 |
| Hyp-(Ara)₃ | 32 | 58 | 396 | 22810 |
| Hyp-(Ara)₂ | 4 | 7 | 264 | 1901 |
| Hyp-(Ara)₁ | 5 | 9 | 132 | 1188 |
| NG-Hyp | 3 | 5 | 0 | 0 |
| Totals | 100 | 180 | | 79121 |

Weight contributions of the O-linked arabinooligosaccharides were estimated from the Hyp-O-glycoside profile data. Reported here is YK20-EGFP only. The YK8-EGFP, YL8-EGFP, and FK9-EGFP fusion glycoprpteins were estimated the same way. MW, molecular weight (Da/mol)

TABLE 9

Weight contribution of the monogalactosides of YK20-EGFP.

| YK20-EGFP | Number/Molecule | MW of Gal | Daltons of Gal |
|---|---|---|---|
| Ser-O-Gal | 53 | 162.2 | 8642 |
| NG-Ser | 8 | 0 | 0 |
| Total Ser | 61 | | 8642 |

From table 6 we know that the weight contribution of the oligoarabinosides is 79121. From table 5 we know that the fusion glycoprotein is 90 mol % arabinose thus (599 mol equiv.). Galactose was 8 mol % galactose (53 mol equiv.) The weight contribution of galactose was calculated from these values. The weight contributions of galactosides in YK8-EGFP, YL8-EGFP, and FK9-EGFP fusion glycoproteins were estimated the same way. MW, molecular weight (Da/mol); NG-Ser, non-glycosylated Ser.

TABLE 10

Weight contribution of the protein of YK20.

| Amino acid | Number of residues | Residue wt. | Daltons | Module mol % |
|---|---|---|---|---|
| Ser | 61 | 87.08 | 5312 | 18.8 |
| Hyp | 180 | 113.10 | 20358 | 55.4 |
| Tyr | 60 | 147.18 | 8831 | 18.5 |
| Lys | 20 | 128.17 | 2563 | 6.2 |
| Pro | 1 | 97.12 | 97 | 0.3 |
| Thr | 1 | 101.11 | 101 | 0.3 |
| Arg | 2 | 156.19 | 312 | 0.6 |
| Total | 325 | | 37575 | 100.0 |

The deduced translation of the YK20 gene sequence in FIG. 1A was used to estimate the molecular wt. contribution of the polypeptide. The weight contributions of the polypeptide in YK8-EGFP, YL8-EGFP, and FK9-EGFP were estimated the same way.

TABLE 11

Estimated molecular weights (Da) of YK20-EGFP, YK8-EGFP, YL8-EGFP, and FK9-EGFP.

| Weight Contributors | YK20-EGFP | YK8-EGFP | YL8-EGFP | FK9-EGFP |
|---|---|---|---|---|
| Arabinosides | 79121 | 31152 | 30096 | 32208 |
| Galactosides | 8642 | 2945 | 5283 | 3914 |
| EGFP | 26924 | 26924 | 26924 | 26924 |
| Module | 37575 | 15387 | 15267 | 17237 |
| Total (Daltons) | 152262 | 76408 | 77570 | 80283 |

Summation of the wt contributions of the arabinosides, the galactosides and the polypeptide components yielded the estimated molecular weights of each fusion glycoprotein. Values are reported in Daltons.

These calculations indicate that YK20-EGFP is 152 kDa of which 58% is carbohydrate (CHO), YK8-EGFP is 76.4 kDa (45% wt. CHO), YL8-EGFP is 77.6 kDa (45% wt. CHO), and FK9-EGFP is 80 kDa (45% wt. CHO). These values compare well with the weight recoveries after HF deglycosylation (Table 3) and the neutral sugar compositions (Table 7), with the exception of YK20-EGFP and FK9-EGFP. The weight percent carbohydrate of these fusion glycoproteins appear to be underestimated from the neutral sugar compositions. Only YL8-EGFP has a Gal:Ser ratio>1, as some of the Gal residues are in a Hyp-PS linkage.

Isolation of pI 4.6 Extensin Peroxidase from Tomato

Figure 23:
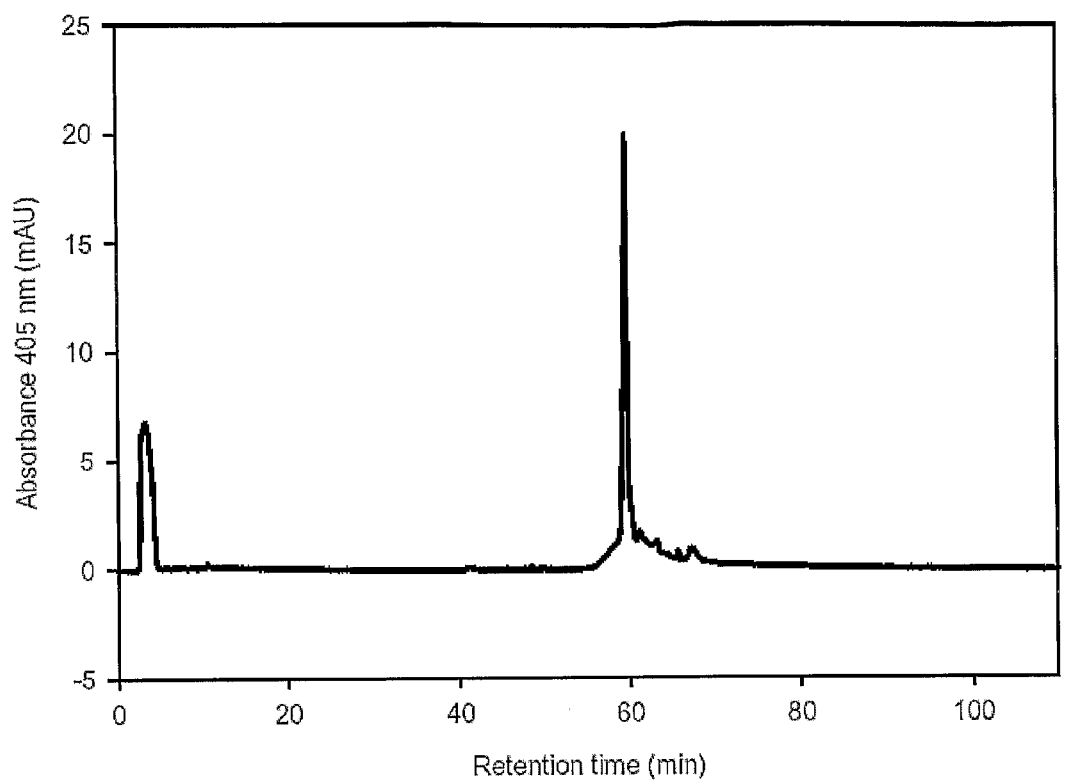
FIG. 23 shows the purification of the pI 4.6 extensin peroxidase by anion exchange HPLC. Heme absorbance was monitored at 405 nm, and a single peak eluted at ~50% B (250 mM NaCl).

A single extensin peroxidase peak was retained and then eluted from the DEAE-5PW anion exchange HPLC column (FIG. 23). Thus, preparative DEAE purified enzyme was used for all further crosslinking reactions.

In Vitro Crosslinking of Extensin Precursors with pI 4.6 Extensin Peroxidase

Figure 24:
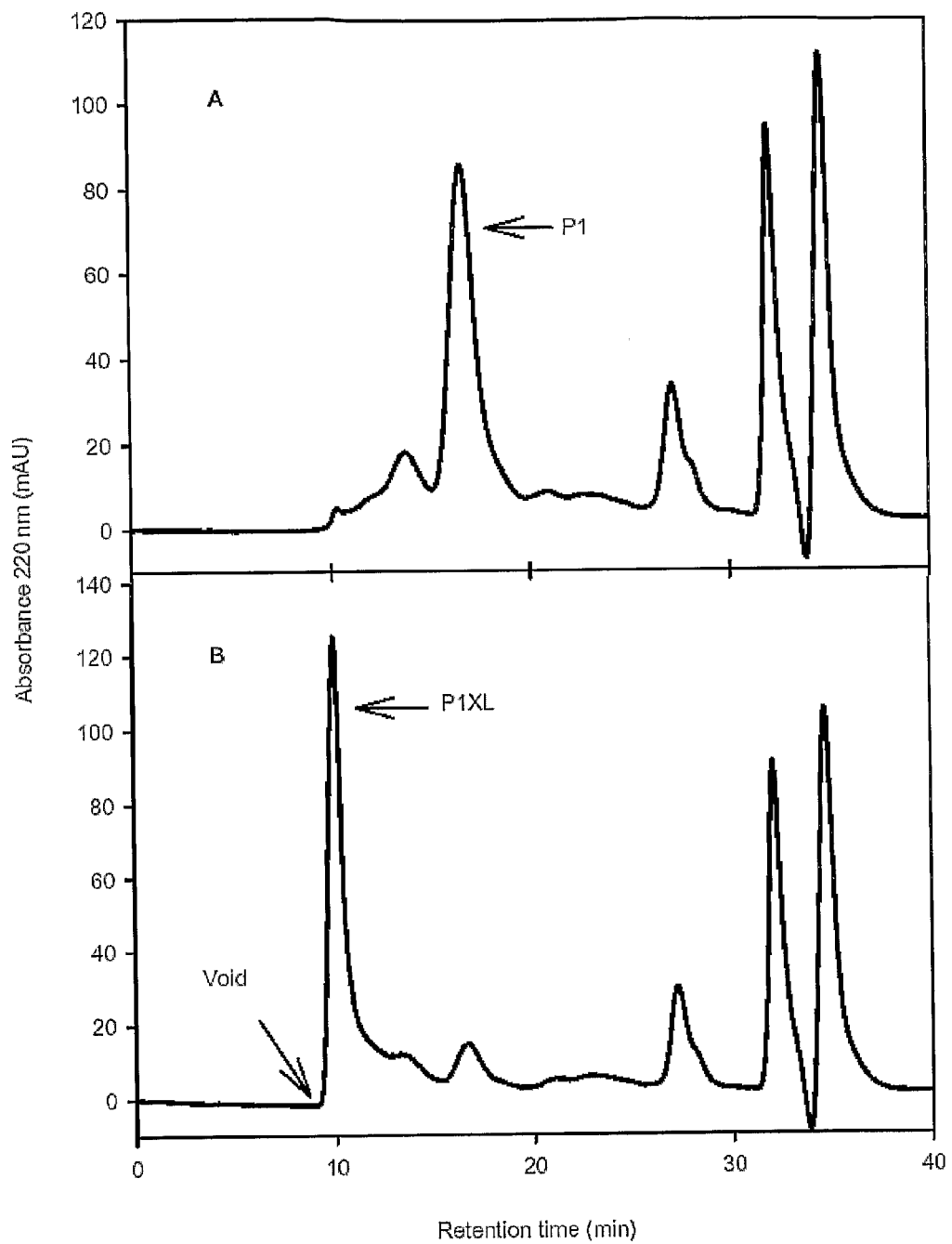
FIG. 24 shows in vitro crosslinking of P1 extensin (40 µg) by the pI 4.6 extensin peroxidase. Crosslinking reactions at time zero (A) and after 15 minutes of incubation (B) were separated by Superose-6 gel filtration chromatography. Peaks eluting after 22 min are a result of the crosslinking buffer and stopping reagent. P1, monomic P1 extensin; P1XL, crosslinked P1 extensin.
Figure 27:
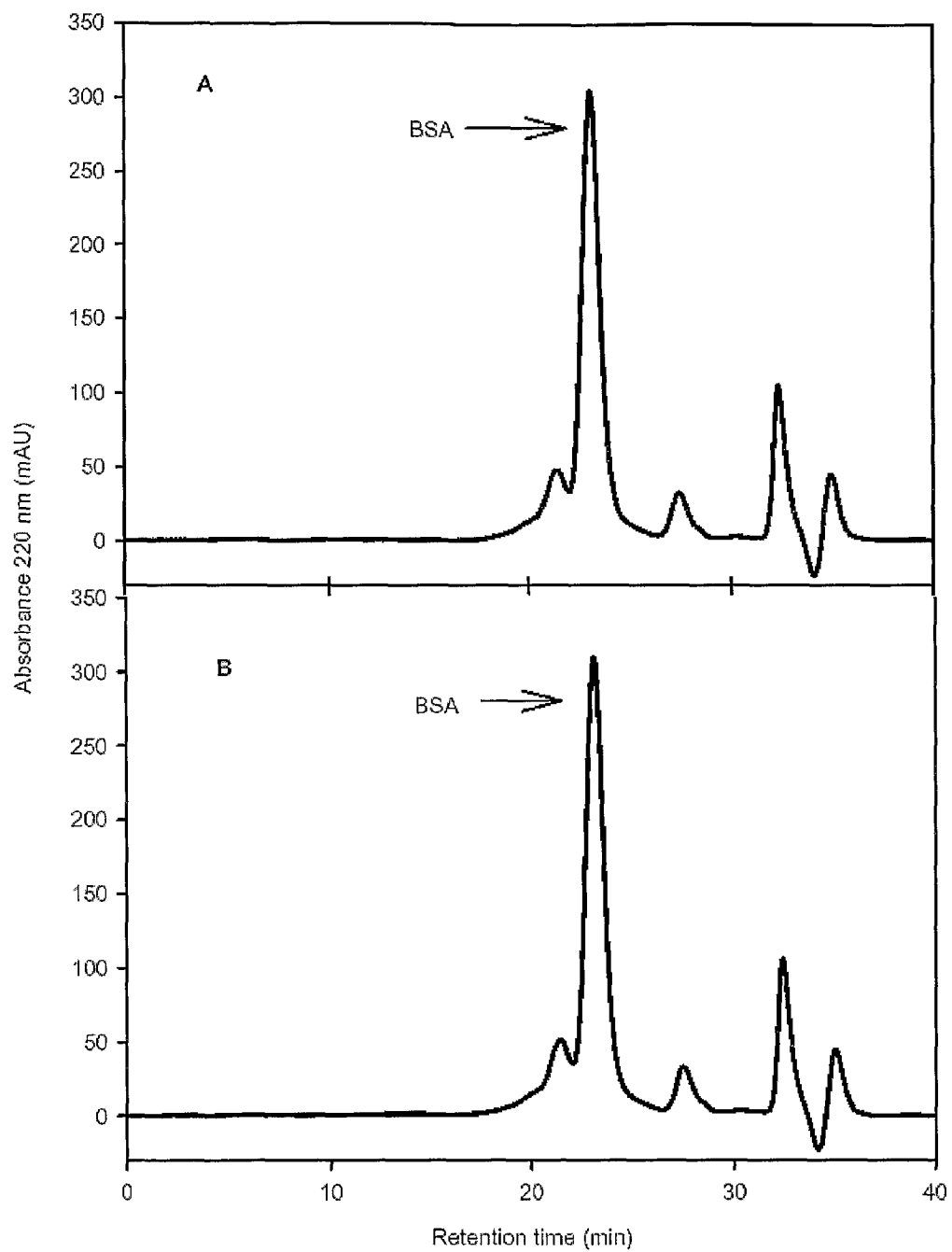
FIG. 27 shows in vitro crosslinking reactions using BSA (40 µg) as a control substrate. Crosslinking reactions were incubated 0 min (A) and 15 min (B) then separated by Superose-6 gel filtration chromatography. BSA did not crosslink.
Figure 28:
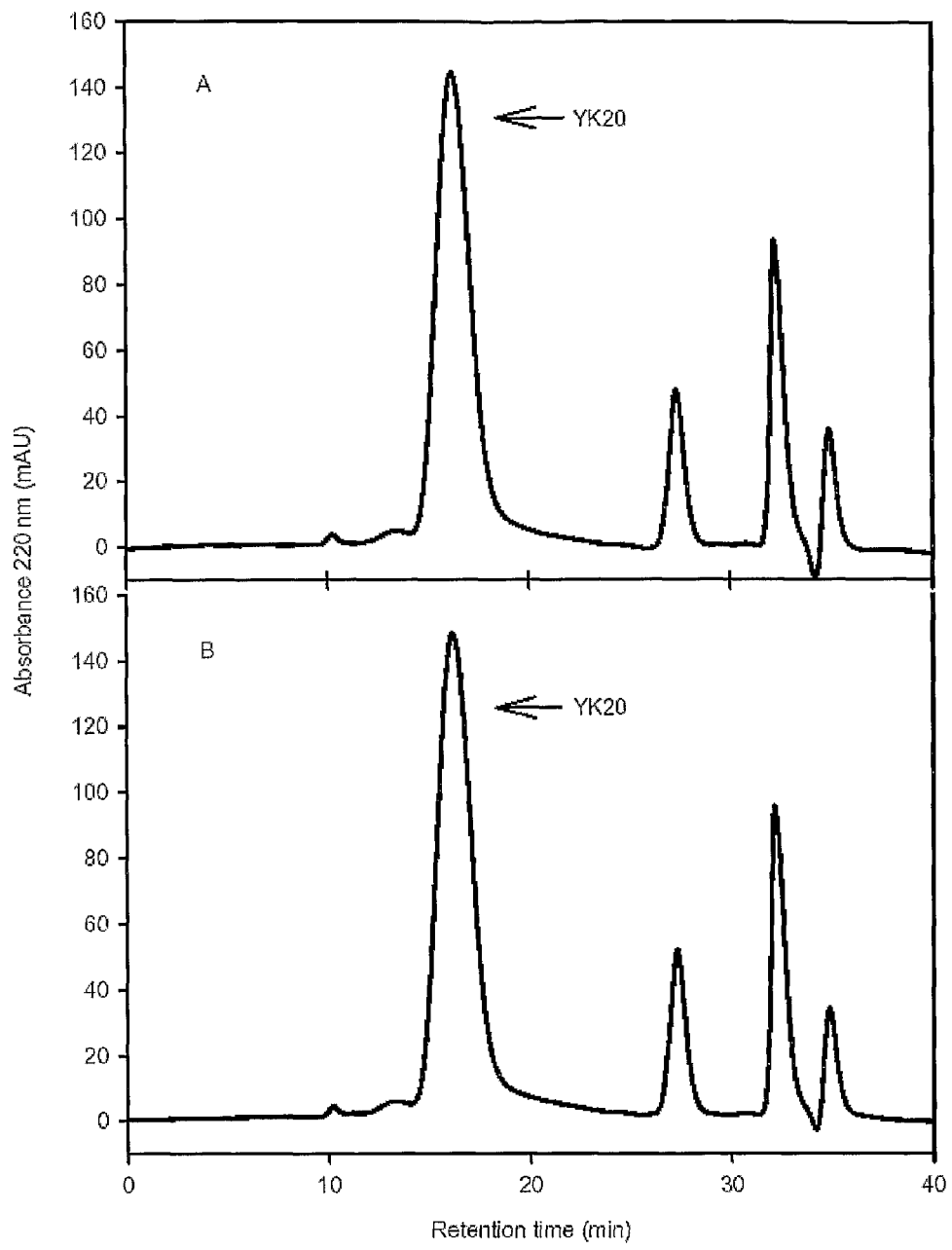
FIG. 28 shows in vitro crosslinking reactions of YK20 (40 µg) lacking the extensin peroxidase enzyme. Crosslinking reactions lacking the addition of peroxidase were incubated 0 min (A) and 15 min (B) then separated by Superose-6 gel filtration chromatography. YK20 does not crosslink in this time frame without the addition of extensin peroxidase.
Figure 29:
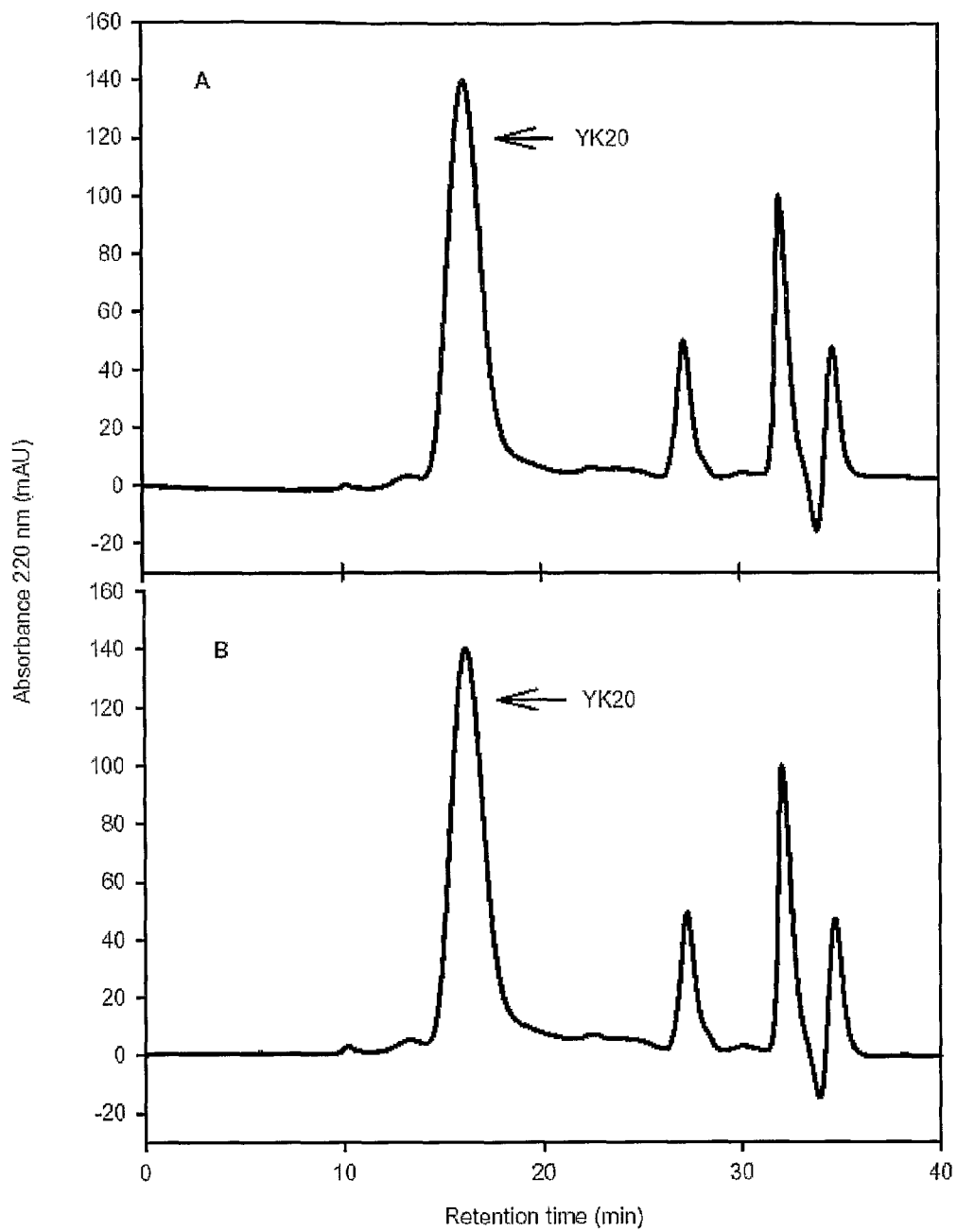
FIG. 29 shows in vitro crosslinking reactions of YK20 (40 µg) lacking the $H_2O_2$ co-substrate. Crosslinking reactions lacking the addition of hydrogen peroxide were incubated 0 min (A) and 15 min (B) then separated by Superose-6 gel filtration chromatography. YK20 does not crosslink with out the addition of $H_2O_2$.
Figure 30:
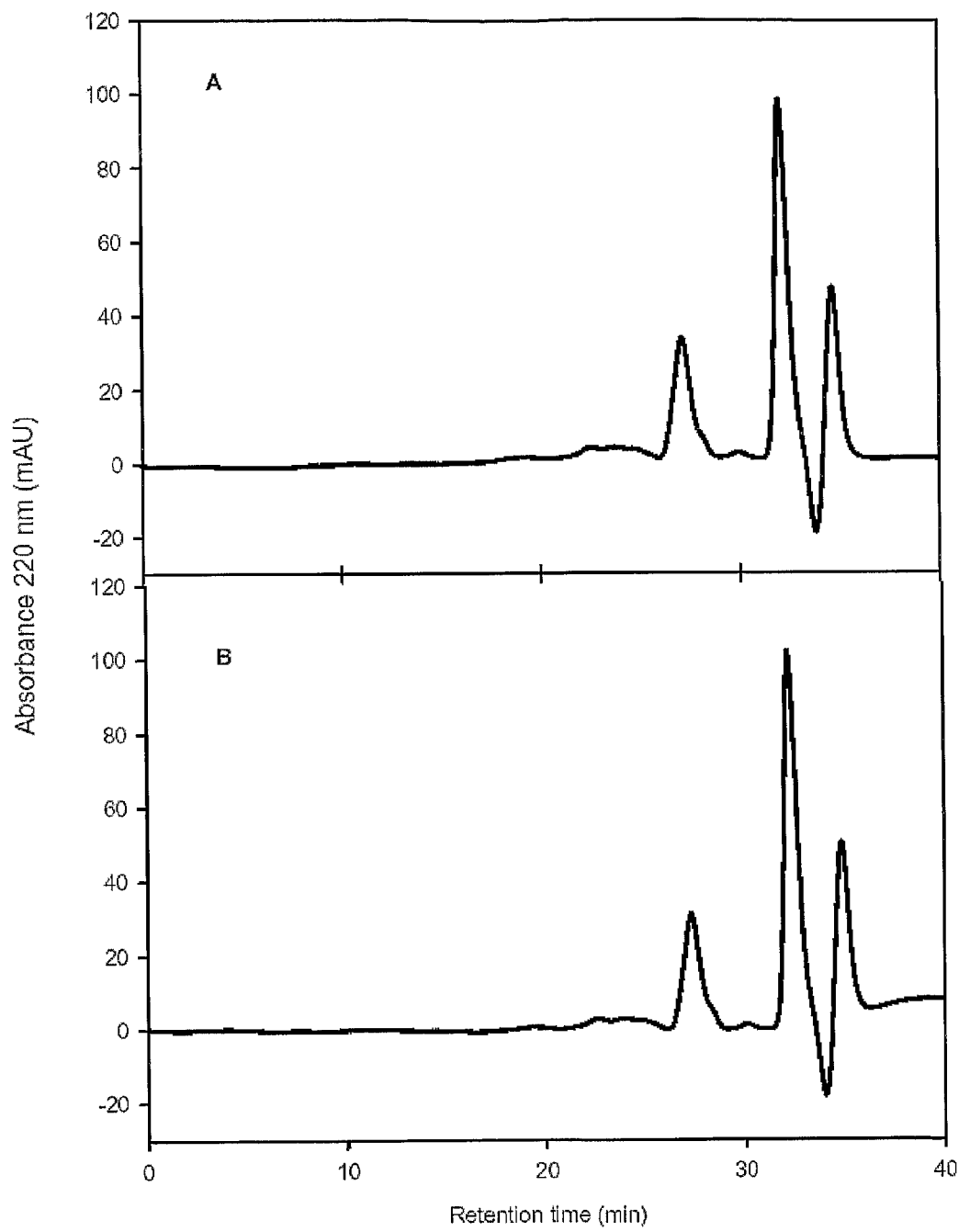
FIG. 30 shows in vitro crosslinking reactions lacking extensin substrate. Crosslinking reactions were incubated 0 min (A) and 15 min (B) then separated by Superose-6 gel filtration chromatography. Note that peaks eluting after ~22 min are a result of the buffer and stopping reagents.

Extensin peroxidase isolated from tomato cell suspension cultures was used to determine the substrate requirements for intermolecular covalent crosslinking in vitro. Native tomato P1 extensin was used as a positive crosslinking control substrate (FIG. 24) (Schnabelrauch et al. 477-89). Native tomato P1, YK20, YK8, and YL8 were able to be covalently crosslinked in vitro by the tomato pI 4.6 extensin peroxidase (FIG. 25). The FK9 glycomodule was not a substrate for the pI 4.6 extensin peroxidase nor was BSA (FIGS. 26 and 27). It was also shown that both the enzyme and peroxide were required for in vitro crosslinking of YK20 (FIGS. 28 and 29). Peaks eluting after 22 min are a result of the crosslinking buffers and stopping reagent (FIG. 30).

In Vitro Crosslinking Rate Determination for the P1, YK20, YK8, YL8 and FK9 Substrates In vitro crosslinking reaction rates were determined from freshly prepared substrate stocks of P1, YK20, YK8, and YL8 using a first order rate equation. Crosslinking reactions were performed in triplicate and the mean crosslinking rates (μg crosslinked per sec)+/− the estimated standard deviations were 6.2+/−0.68 for P1, 4.9+/−0.31 for YK20, 3.4+/−0.13 for YK8, 1.4+/−0.07 for YL8 (FIG. 31). Since FK9 does not crosslink, the reaction rate is reported as zero.

In Vitro Crosslinking of Extensin Precursors with Tobacco Salt-Eluates

To check for the presence of an extensin peroxidase in tobacco BY-2 cell suspension cultures, in vitro crosslinking assays using crude tobacco culture media (E1) and a salt-eluate of intact tobacco cells (E2) on native tomato P1 extensin and YK20 substrates. The amount of enzyme activity was quantified by ABTS assay for E1 and E2 and equal amounts of both enzymes (~35 ng, 7 times the normal amount) were used per standard amount of substrate (60 μg). I found that the E2 was able to catalyze the complete in vitro crosslinking of P1 and YK20 over a reaction time of 18 h, whereas E1 was not.

In Vitro Crosslinking of YK20 with Crude Cationic Tomato Peroxidases

Figure 32:
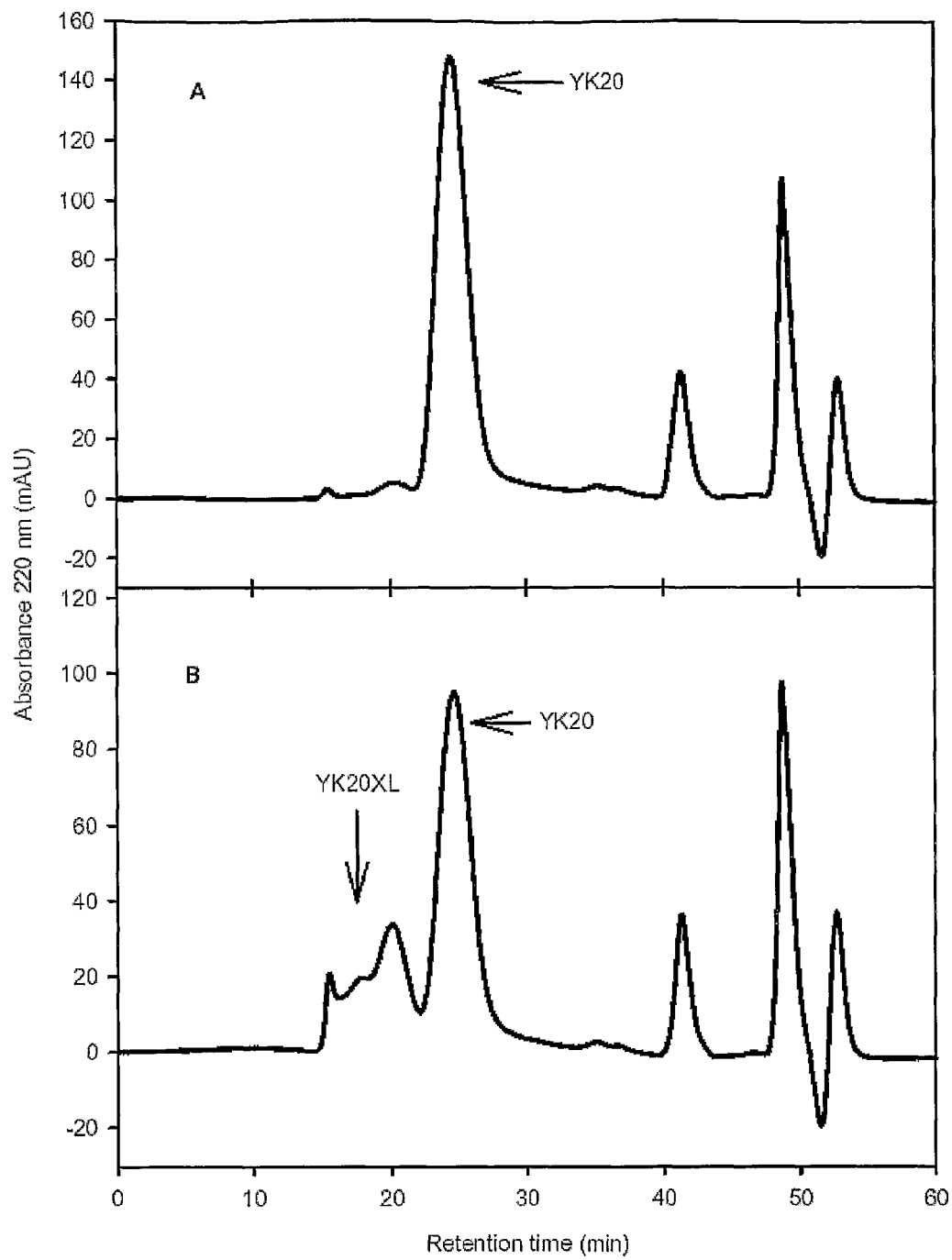
FIG. 32 shows in vitro crosslinking of YK20 by a crude cationic void peroxidase preparation. Reactions were incubated 0 min (A) and 30 min (B), then separated by Superose-6 gel filtration (0.5 ml/min; OD 220 nm). Some crosslinking was observed for YK20 (shown here), P1, and YL8.

The preparative DEAE void contained a significant amount of peroxidase activity. This fraction was tested for its ability to crosslink P1, YK20, and YL8 in vitro. The crosslinking reactions were the same as the standard reactions except, the enzyme concentration and the incubation times were doubled. A minor amount of crosslinking was observed for all three substrates (FIG. 32).

Amino Acid Composition of the Crosslinked YK20

Amino acid compositions of the crosslinked YK20 (YK20XL) were compared with the YK20 glycomodule (Table 12). The amino acid compositions showed a decrease in IDT and total Tyr equivalents after crosslinking.

TABLE 12

Amino acid compositions of YK20 and YK20XL.

| | Amino Acid Composition (mol %) | | |
|---|---|---|---|
| | YK20 | | YK20XL |
| Amino Acid | Protein | Gene | Protein |
| Hyp | 59.8 | 0 | 56.8 |
| Pro | 0 | 55.4 | 2.3 |
| Ser | 18.2 | 19 | 18.2 |
| Tyr | 9 | 18.3 | 11.3 |
| 1/2IDT | 8.7 | 0 | 2.6 |
| Phe | 0 | 0 | 0 |
| Lys | 4.3 | 6.4 | 6.4 |
| Leu | 0 | 0 | 0 |
| Thr | 0 | 0.3 | 2.4 |
| Met | 0 | 0.3 | 0 |
| Val | 0 | 0.3 | 0 |
| Total | 100 | 100 | 100 |

Losses of IDT and net Tyr equivalents were observed after in vitro crosslinking.

Neutral Sugar Composition of the Crosslinked YK20

There were no significant differences in the neutral sugar composition between the soluble YK20XL and the YK20 glycomodule (Table 13). Note Glc, Xyl, and Rha are most likely contaminants. We did not detect uronic acids in either YK20 or YK20XL.

TABLE 13

Neutral sugar compositions of YK20 and YK20XL.

| | Mol Percent | |
|---|---|---|
| Glycosyl Residue | YK20 | YK20XL |
| Ara | 91 | 88 |
| Gal | 7 | 9 |
| Rha | 1 | 0 |
| Xyl | 0 | 1 |
| Glc | 1 | 2 |

A slight decrease in the mol % of arabinose and increase in galactose were observed upon crosslinking.

Isolation of a Putative Crosslinking Amino Acid from Crosslinked YK20

Figure 33:
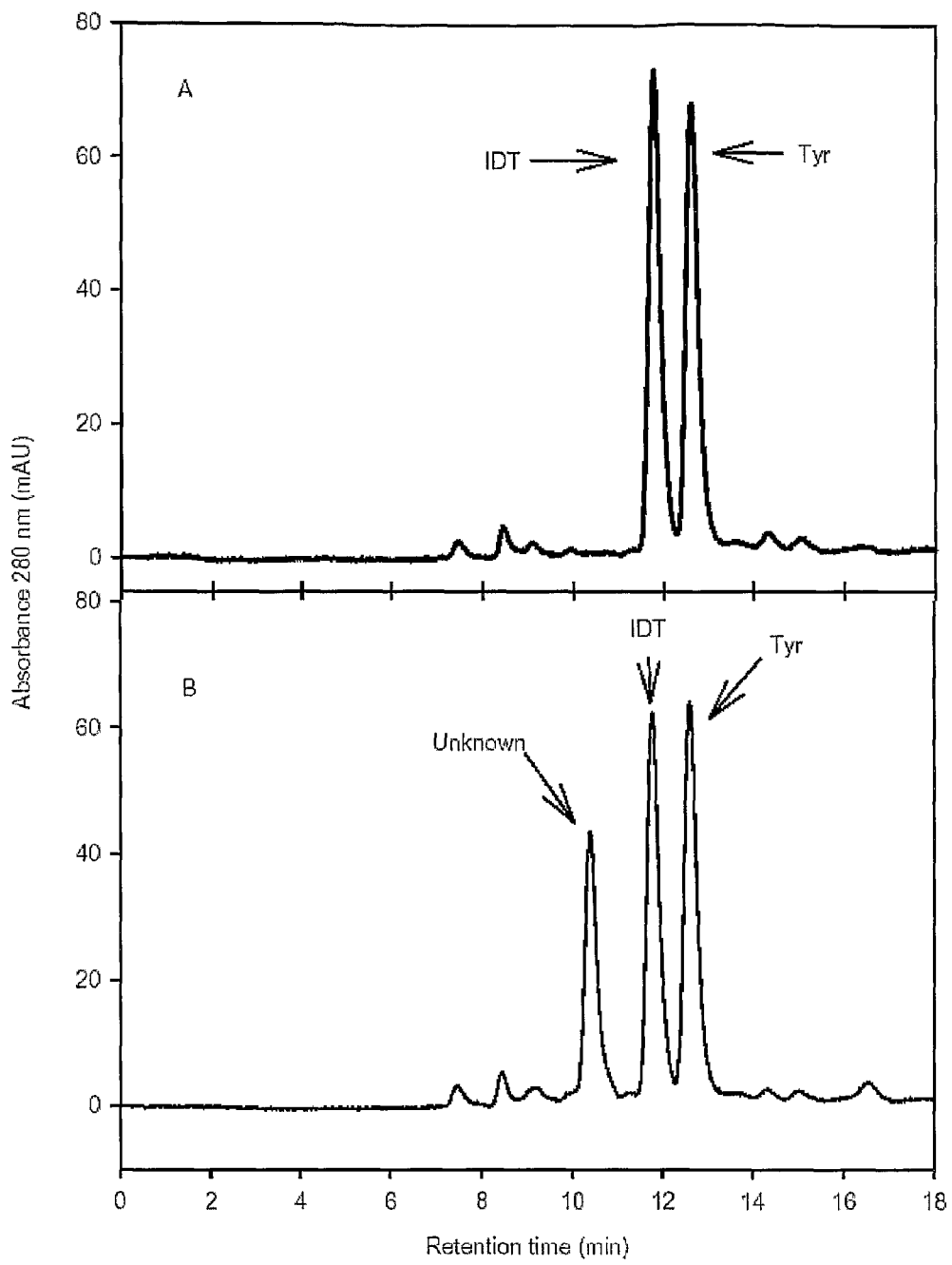
FIG. 33 shows size exclusion chromatography of (A) YK20 acid hydrolysate and (B) YK20XL acid hydrolysate. A putative crosslinking amino acid (unknown) eluting at 10.4 min was isolated from the hydrolysate of YK20XL.
Figure 34:
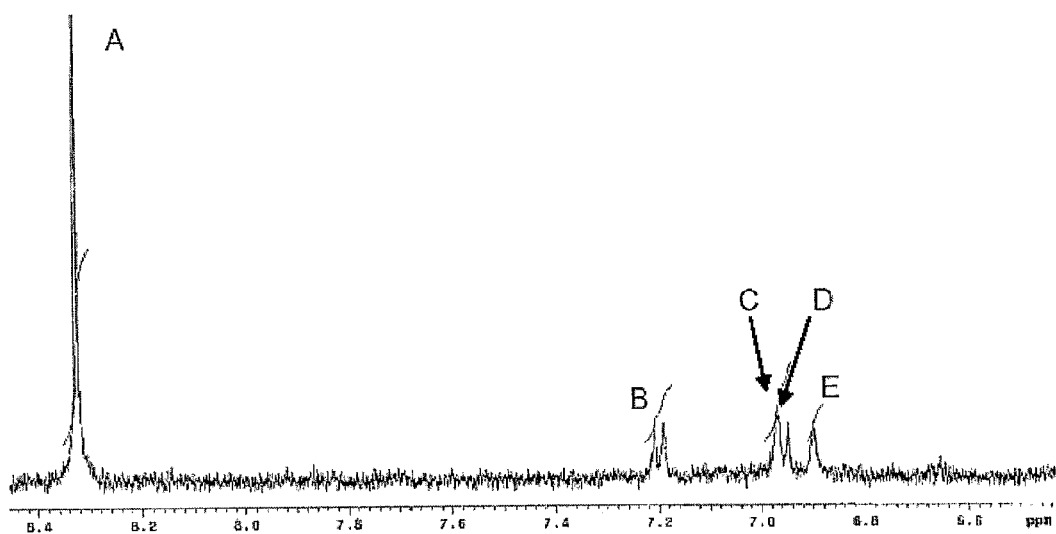
FIG. 34 shows a 1-D $^1$HNMR spectrum of the "unknown." The spectrum was obtained by Dr. Li Tan of Ohio University. (A) N-linked proton resonances, (B)-(E) aromatic proton resonances.

A putative crosslinking amino acid, designated "unknown", was detected in the acid hydrolysates of YK20XL, but not in the YK20 glycomodule (FIG. 33). The unknown was collected and then fractionated again by size exclusion chromatography.

Identification of Crosslinking Amino Acid (Unknown) by Paper Chromatography

Paper chromatography of the "unknown" compound from FIG. 33 and an authentic diisodityrosine standard (Fry's diIDT) demonstrated that they had the same Rf value (Table 14). A putative diIDT standard (my diIDT) freshly prepared from tomato cell wall hydrolysates, also co-chromatographed with the unknown and the authentic standard.

TABLE 14

Paper chromatography of Fry's diIDT, "unknown", and my diIDT in BAW.

| Sample | Rf value | Fluorescence* |
|---|---|---|
| Fry's diIDT | 0.06 | + |
| Unknown | 0.06 | + |
| My diIDT | 0.06 | + |

*Vivid blue fluorescence was observed when viewed under short-wave (254 nm) UV light after exposure with $NH_3$ vapor.

Identification of Crosslinking Amino Acid (Unknown) by Size Exclusion Chromatography The Fry's diIDT standard and the unknown were fractionated by size exclusion chromatography. The authentic diIDT standard co-eluted with the unknown (not shown).

Identification of Crosslinking Amino Acid (Unknown) MALDI-TOF Mass Spectrometry The unknown was sent to Dr. Michael Hare of Oregon State University for molecular weight determination by MALDI-TOF mass spectrometry. The theoretical molecular mass of diIDT is $[M+H]=719$. The mass spectrum of the unknown peak contained a molecular ion of $[M+H]=719$. The same molecular ion was observed in Fry's diIDT both here and as reported earlier (Brady, Sadler, and Fry 323-27) and my diIDT standard. Thus, the putative crosslinking amino acid formed in vitro was diIDT.

Identification of Crosslinking Amino Acid (Unknown) 1-D $^1$HNMR

The 1-D $^1$HNMR spectrum of the "unknown" sample showed 4 groups of resonances from the aromatic region. The resonances at 7.203 (dd, J=8.4 Hz, 2.2 Hz) and 6.965 (dd, 8.4 Hz, 2.2 Hz) ppm (peaks B and D in FIG. 34) suggested this sample contained 1,4-substituted benzene ring(s). Two mutually coupled single-proton doublet resonances (J=2.2 Hz) at 6.900 and 6.970 ppm (peaks E and C in FIG. 34) suggested the existence of 1,2,3,5-substituted benzene ring(s). The N-linked protons showed at 8.330 ppm (peak A in FIG. 34). Furthermore, the ratio of integrated area of signals A:B:C:D:E was 12:4:2:4:2. These results strongly suggested that the "unknown" sample corresponded to diDT, in which all the N atoms were fully protonated.

By using the ChemDraw program, the predicted data of diDT showed similar spectrum pattern and chemical shifts as those of the "unknown" also indicated that it was diIDT (FIG. 35).

APPLICATION OF THE TECHNOLOGY

Example 2

Fiber Formation

Crosslinking extensin modules (SOOOOTOVYK (SEQ ID NO: 76); see Tables 16 and 17) (Note: here onward the single letter codes are used to denote amino acids, with O representing Hyp) are placed at the N- and C-termini, and a central stretch composed of rigid SOOOO repeats (bolded below) flanked on either side with elastin sequences (italicized below; See Table 18). This construction should produce tough, rigid, protease-resistant, elastic fibres of high tensile strength, analogous to fibres found in mussel byssus threads but with enhanced water-holding ability in the glycosylated regions.

Each of the repetitive modules in Examples 2A and 2B, including the elastin module, has already been successfully expressed in plants. Peroxidase-catalyzed intermolecular crosslinking of the Thr-Hyp-Val-Tyr-Lys (SEQ ID NO: 77) module at the ends of the molecules should produce long fibres. (Note: the Lys residues in P1 extensin sequences are resistant to trypsin).

Example 2A

SOOOOTOVYKSOOOOTOVYKSOOOO[*VGVPG VGVPG*]$_5$

[SOOOOSOOOOSOOOO]$_6$[*VGVPG VGVPG*]$_5$-

SOOOOTOVYKSOOOOTOVYKSOOOO (SEQ ID NO: 78)

The variant below replaces the central rigid, arabinosylated SOOOO repeats with the more flexible SOSOSO repeats (Bolded below), or AOAOAO repeats, that serve as arabinogalactan polysaccharide addition sites. These polysaccharide additions sites greatly increase the amount of carbohydrate on the molecule, impart a negative charge due to the abundance of uronic acids in the polysaccharide, and promote an extended conformation.

Example 2B

SOOOOTOVYKSOOOOTOVYKSOOOO[*VGVPG VGVPG*]$_5$

[SOSOSOSOSOSOSOSOSOSOSOSO]$_6$[*VGVPG VGVPG*]$_5$

SOOOOTOVYKSOOOOTOVYKSOOOO (SEQ ID NO: 79)

Example 3

HRGP-Based Emulsifiers

Gum arabic glycoprotein is an excellent emulsifier (J-F Xu and M. Kieliszewski, unpublished data). Features of GAGP as well as other HRGPs can be exploited to create novel emulsifiers. Example 3 is very similar to Example 2, except it lacks crosslinking motifs and the elastin repeats of Example 2 have been replaced with a smaller (12 residues, italicized below), extended (Pro-rich) but flexible, hydrophobic module. Charge repulsions and steric interference produced by the rhamnoglucuronoarabinogalactan polysaccharide sidechains attached to the AOAO repeats should help stabilize an oil in water emulsion by preventing aggregation/flocculation of the emulsion particles. Further stabilization can be achieved by adding crosslinking modules. Variations include glycoproteins having only a single hydrophobic module and a single glycosylated HRGP module or many of each type dispersed regularly throughout the chain.

Example 3

(SEQ ID NO: 80)
*VPGVPGVPGVPG*[AOAOAOAOAOAOAOAOAOAO]$_3$*VPGVPGVPGVPG*

Example 4

This Example exploits variations of the GAGP repeat and the extensin TOVYK intermolecular crosslinking motif (underlined) to create a crosslinked emulsifier. The C-terminus variation of the GAGP repeat (italicized and bolded) has decreased glycosylation, increased flexibility, and increased hydrophobicity, which will allow the molecule to interact with the surface of an oil droplet. Such a molecule might facilitate slow-release drug delivery from an oil-in-water emulsion.

(SEQ ID NO: 81)
SOOOTLSOSOTOTOOLGPHSOOOTLSOSOTOTOOLGPH<u>TOVYK</u>SOOOTLS

OSOTOTOOLGPHSOOOTLSOSOTOTOOLGPH<u>TOVYK</u>SOOOTLSOSOTOTO

OLGPHSOOOTLSOSOTOTOOLGPH<u>TOVYK</u>SOOOTLSOSOTOTOOLGPH

*SOLPTLSOLPTOTOOLLPH SOLPTLSOLPTOTOOLLPH*

Methods to test the properties of the inventive materials include:

1. Crosslinking—cross-linking of monomers to form multimers can be tested several ways:
    a. Size exclusion chromatography is an effective assay as already demonstrated by Schnabelrauch et al. (Schnabelrauch, L. S., Kieliszewski, M. J., Upham, B. L., Alizedeh, H., and Lamport, D. T. A. (1996) *Plant J.,* 9, 477-489.)
    b. Assay of free Lys in crosslinks putatively involving Lys residues by the use of the highly reactive acrylonitrile for the cyanoethylation of all the freely available —NH$_2$ groups.
    c. Dityrosine or isodityrosine formation for crosslinks involving Tyr residues (Epstein, L. and Lamport, D. T. A. (1984) *Phytochem.,* 23, 1241-1246).
    d. Surface hydrophobicity measurements using cis-parinaric acid as a fluorescent probe (Liu, M. and Damodaran, S. (1999) *J. Agric. Food Chem.,* 47, 1514-1519; Kato, A. and Nakai, S. (1980) *Biochim. Biophys. Acta,* 624, 13-20).
2. Mechanical properties of biopolymer films
    a. Compression isotherms via Langmuir film balance (Fauconnier, M. L., Blecker, C., Groyne, J., Razafindralambo, H., Vanzeveren, E., Marlier, M., and Paquot, M. (2000) *J. Agric. Food Chem.,* 48, 2709-2712).
3. Emulsifying properties will be evaluated as follows:
    a. At different pH
    b. Different ionic strengths (Popineau, Y., Pineau, F., Evon, P., and Berot, S. (1999) *Nahrung,* 43, 361-367)
    c. Stability of the emulsion (Liu, M. and Damodaran, S. (1999) *J. Agric. Food Chem.,* 47, 1514-1519)
    d. Droplet size and surface charge: Emulsions containing the smallest globules tend to be the most stable (200-500 nm), as do emulsions that have a high surface charge. Droplet size will be measured in a Coulter counter as described by Dickenson et al. (Dickenson, E., Rolfe, S. E., and Dalgleish, D. G. (1988) *Food Hydrocolloids,* 2, 397-405). Zeta potential measurements are typically carried out using a Doppler electrophoresis apparatus or via moving-boundary electrophoresis (Washington, C. (1990) *Int. J. Pharm.,* 66, 1-21).
4. Fiber formation and Fiber properties—
    Extrusion of crosslinked products through an appropriately sized nozzle will yield fibers. After a curing stage, the physical properties of the fibers will be determined in an extensometer to measure their elastic modulus and tensile strength (Cosgrove, D. J. (1993) *New Phytol.,* 124, 1-23).
5. Elastic properties/viscoelasticity can be measured using a rheometer as described by Larre et al (Larre, C., Denery-Papini, S., Popineau, Y., Deshayes, G., Desserme, C., and Lefebvre, J. (2000) *Cereal Chem.* (2000), 77, 121-127).
6. Lipid encapsulation—lipid exposed at the surface of a microcapsule can be measured via extraction with chloroform as in: Minemoto, Y., Adachi, S., and Matsuno, R. (1999) *Food Sci. Technol. Res.,* 5, 289-293.

TABLE 16

Repetitive Sequences Common in Hydroxyproline-rich Glycoproteins

| Characteristic Sequence | HRGP |
|---|---|
| Ser-Hyp-Hyp-Hyp-Hyp-Thr-Hyp-Val-Tyr-Lys (SEQ ID NO: 1) | P1-type extensin |
| Ser-Hyp-Hyp-Hyp-Hyp-Ser-Hyp-Ser-Hyp-Hyp-Hyp-Hyp-Hyp-Tyr-Tyr-Tyr-Lys (SEQ ID NO: 3) | P3 extensin |
| Pro-Hyp-Val-Tyr-Lys (SEQ ID NO: 82) | Proline-rich protein |
| Ala-Hyp-Ala-Hyp | Arabinogalactan-protein |

TABLE 17

HRGP repetitive glycomodules, peptide modules and their corresponding properties

| Repetitive module | Properties |
|---|---|
| X-Hyp-Hyp-Hyp-Hyp | Glycomodule common in extensins; this module has a polyproline-II extended conformation; Extensive arabinosylation of Hyp enhances the polyproline-II conformation and rigidifies the module (X = Ser, Ala, Thr). |
| X-Hyp-Hyp | Glycomodule common in arabinogalactan- proteins; Less polyproline II conformation than the X-Hyp-Hyp-Hyp-Hyp glycomodule; First Hyp is always arabinosylated, the second is occasionally. (X = Ser, Ala, Thr) |
| X-Hyp-X-Hyp | Glycomodule which defines the arabinogalactan-proteins (i.e. clustered non-contiguous Hyp); An extended random coil conformation further enhanced by arabinogalactan-polysaccharide addition to each Hyp (X = Ser, Ala). |
| X-Hyp-Val-Tyr-Lys | Peptide module of extensins and PRPs; adhesion; peroxidase-catalyzed intermolecular cross-linking; Possible reverse β-turns; tandem repeats of this module may increase elasticity. (X = Thr, Glu, Pro, His, Ile). |
| Tyr-Tyr-Tyr-Lys (SEQ ID NO: 7) | Peptide crosslinking modules common in extensin; Peroxidase-catalyzed |
| Tyr-Lys-Tyr-Lys (SEQ ID NO: 33) | (?) intramolecular isodityrosine cross-linking sequences; probable intermolecular cross-link that enhances hydrophobicity; intramolecular crosslink rigidifies this module. |
| Lys-Pro | Ionic/covalent cross-linking motif of extensins and PRPs |

TABLE 18

Non-HRGP peptide modules and corresponding properties

| | |
|---|---|
| Thr-Val-Gln-Gln-Glu-Leu (SEQ ID NO: 83) | Sequences for transglutaminase crosslinking |
| Pro-Gly-Gln-Gln-Ile-Val (SEQ ID NO: 84) | to Lys residues in HRGPs; formation of $N^\epsilon$-(γ-glutamyl)lysine. |
| Leu-Cys-Cys-Ser X-Cys-Gly (SEQ ID NO: 85) | Inter/intramolecular disulfide bond formation. (X = Gln, Lys, Arg). |
| Val-Pro-Gly-Val-Gly (SEQ ID NO: 86) | Elastomeric module |

Example 5

Additional Cross-Linking Motifs

Summary

Figure 36:
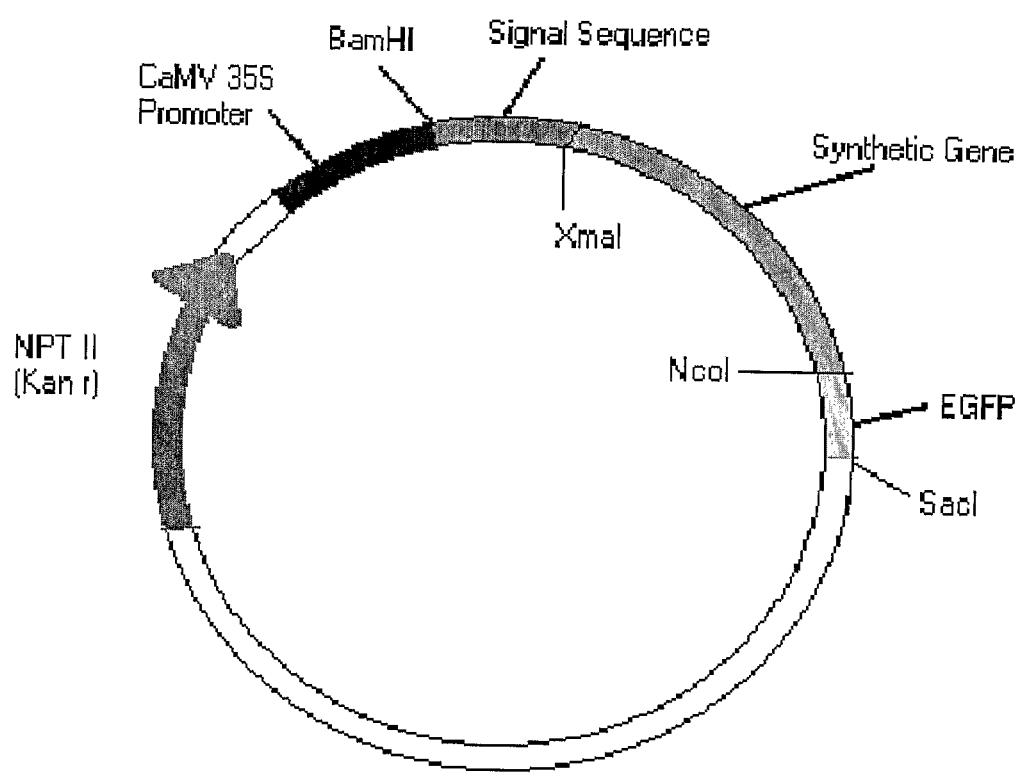
FIG. 36 diagramatically illustrates the pBI121 plasmid with signal sequence-synthetic gene-EGFP. The method of gene construction was adapted from Shpak et al. (*Proc. Natl. Acad. Sci.*, 1999, 96, 14736-14741) Overlapping oligonucleotide pairs were annealed and polymerized. The synthetic gene was inserted into pUC18 as a BamHI-EcoRI fragment, sequenced and then inserted between the signal sequence and EGFP in pUC-SS-EGFP as a XmaI-NcoI fragment. Finally, the signal sequence-synthetic gene-EGFP unit was placed in the plant transformation vector pBI121 as a BamHI-SacI fragment.

P1 extensin is a hydroxyproline-rich glycoprotein (HRGP) that is an integral part of the primary plant cell wall. It consists mainly of two repetitive motifs: SPPPPTPVYK (SEQ ID NO: 87) and SPPPPVKPYHPTPVYK (SEQ ID NO: 88). Earlier work demonstrated the requirement of a Val-Tyr-Lys motif for in vitro intermolecular cross-linking of P1 by extensin peroxidase. Tyrosine and lysine contain reactive groups, which are proposed to play a role in the cross-linking of extensin. Here we have tested the role of Val-Tyr-Lys motif in cross-linking by designing synthetic genes and expressing them in tobacco cells. These genes encode the P1 motif: SOOOOTOVYK (SEQ ID NO: 76) (O is Hyp) and variants that differ in their cross-linking motifs with substitutions of Tyr→Phe and Lys→Leu. FIG. 36 shows the plasmid construct.

Figure 37:
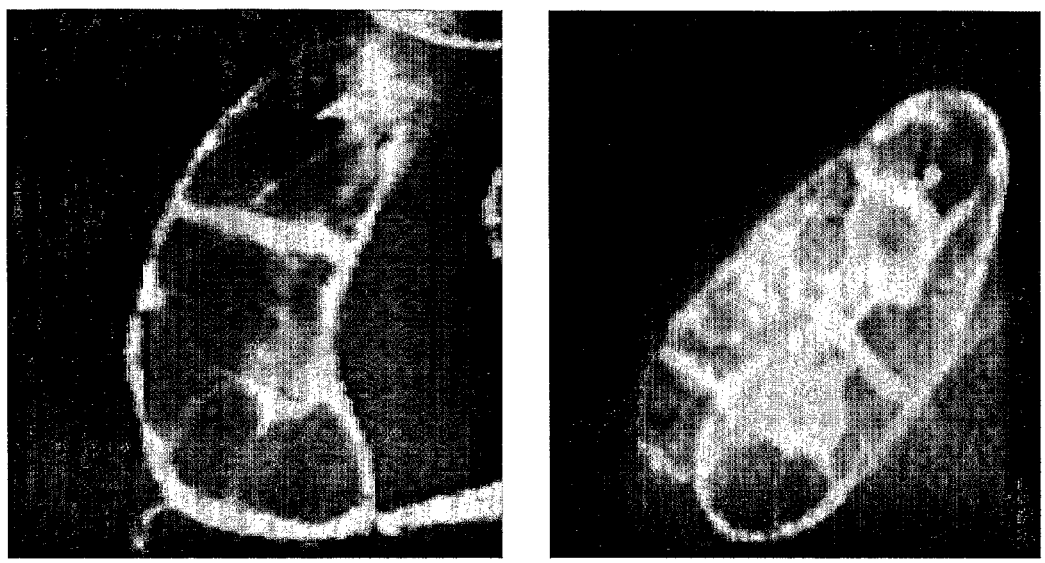
FIG. 37 is a photomicrograph of cell lines expressing EGFP fusion proteins. Panels A. [VYK]$_6$ (SEQ ID NO: 4) and B. [VFL]$_6$ (SEQ ID NO: 5) are transformed cell lines that show EGFP fluorescence when viewed with a confocal laser scanning fluorescence mircroscope, excitation 488 nm and emission 510 nm.
Figure 38:
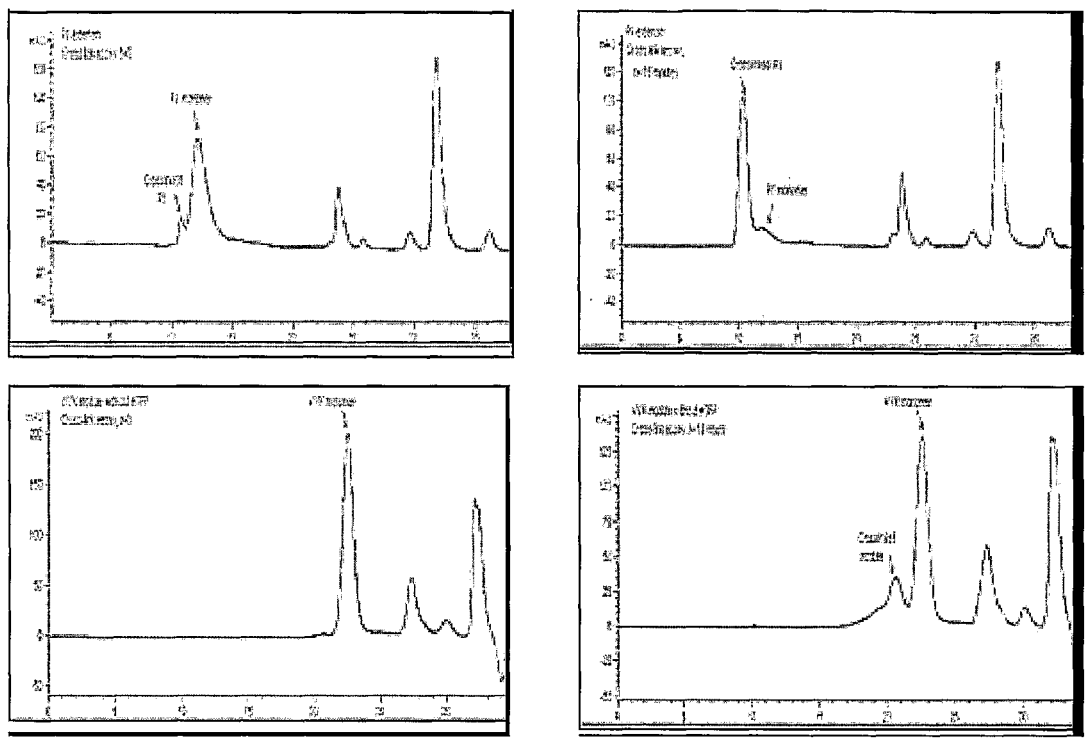
FIG. 38 shows results of cross-link assays on a Superose 6 gel filtration column. Superose 6 profiles of P1 extensin at 220 nm: (a) before and (b) after cross-linking for 15 minutes. Superose 6 profiles of VYK module at 220 nm: (c) before and (d) after cross-linking for 19 hours. As cross-linking occurs, the monomer peak decreases and a peak representing a larger cross-linked oligomer appears.

The genes were expressed in *Nicotiana tabacum* BY2 suspension cultured cells as enhanced green fluorescent protein (EGFP) fusion proteins and were targeted through the ER and Golgi to the cell wall via a tobacco extensin signal sequence. (FIG. 37 shows photomicrographs of cells.) The transgene products were isolated from cell culture medium by a combination of hydrophobic interaction and reverse phase C4 column chromatography. The fusion proteins underwent hydroxylation of proline and extensive arabinosylation of Hyp residues similar to endogenous P1. The VYK construct [SPPPPTPVYK]$_6$ (SEQ ID NO: 89) (one of the cell lines expressing this glycoprotein is designated VYK C1) was cross-linked in vitro by tomato extensin peroxidase, while the VFL construct [SPPPPTPVFL]$_6$ (SEQ ID NO: 90) (one of the cell lines expressing this glycoprotein is designated VFL-F) showed no cross-linking activity. Another cell line (designated VYL-6.1) expressing 6 repeats of the DNA sequence [SPPPPTPVYL] (SEQ ID NO: 91) has not been tested for crosslinking (FIG. 38 shows results of crosslinking studies.)

Experimental Methods

Isolation of the Fusion Proteins

Soluble P1 extensin fusion proteins containing six repeats were isolated from the culture medium. The media was concentrated by rotary evaporation, dialyzed against water, and then freeze-dried. The dry sample was redissolved in 2M sodium chloride and injected onto a hydrophobic interaction column. A step gradient of decreasing sodium chloride was used to elute the column. Fractions were monitored for fluorescence using a Hewlett-Packard 1100 Series flow-through fluorometer. The fluorescent fractions were then purified using gel filtration and reverse-phase chromatography.

In Vitro Cross-Linking Assays of P1 Extensin Gene Products

The isolated fusion proteins were treated with trypsin to remove EGFP and were then tested as substrates for the pI 4.6 peroxidase isolated from tomato. The cross-linking of the monomers was measured by a Superose 6 gel filtration assay of cross-linked product. Native P1 extensin served as the positive control and the $(SPPPPTPVFL)_6$ (SEQ ID NO: 90) served as the negative control.

Conclusion

Three fusion proteins were expressed in tobacco cell cultures. These proteins were isolated from the media using hydrophobic interaction, gel filtration, and reverse-phase chromatography. Neutral sugar analysis has shown that the main sugar is arabinose with trace amounts of galactose, which is consistent with native P1 extensin.

The module was cleaved from EGFP by tryptic digestion and the module was then tested for cross-linking activity. Native P1 tomato extensin was used as a control. It appears that the glycoprotein $(SOOOOVYK)_6$ (SEQ ID NO: 92) does cross-link, although to a much lesser extent than P1. The glycoprotein $(SOOOOVFL)_6$ (SEQ ID NO: 93) did not crosslink. The glycoprotein $(SOOOOVYL)_6$ (SEQ ID NO: 94) has not been tested for crosslinking.

Example 6

Cross-Linking HRGPs with Arabinogalactan Glycomodules

Overview

The range of crosslinking HRGPs was expanded to include some containing arabinogalactan glycomodules. Thus, we combined the Ser-Hyp$_4$-Ser-Hyp-Ser-Hyp$_4$-Tyr-Tyr-Tyr-Lys (SEQ ID NO: 3) extensin-type arabinosylated repeats (abbreviated YK below) that can crosslink with (Ala-Hyp)$_n$ arabinogalactan-type repeats (designated AlaPro below). We constructed genes encoding (AlaPro)$_4$(YK)$_{20}$ (peptide disclosed as SEQ ID NO: 6), (AlaPro)$_4$(YK)$_8$ (peptide disclosed as SEQ ID NO: 6), and (AlaPro)$_4$(YK)$_4$ (peptide disclosed as SEQ ID NO: 6) genes, expressed them as EGFP fusion proteins, and tested whether or not the resulting glycoproteins could be cross-linked by tomato extensin peroxidase.

Methods

1). Design of Oligonucleotides for Constructsa.

The 5' end of the sense oligonucleotide (encoding the sequence APAPAPA (SEQ ID NO: 98) above contained a XmaI cut site and the 5' end of the antisense oligonucleotide contained a BbsI cut site. This allowed insertion of the construct into preexisting plasmids pUC-(YK)$_{20}$, pUC-(YK)$_8$, and pUC-(YK)$_4$.

2). Construction of pUC-SS$^{tob}$(AlaPro)$_4$(YK)$_{20/8/4}$EGFP (peptide disclosed as SEQ ID NO: 6), pUC-SS$^{tob}$(YK)$_{20/8/4}$(AlaPro)$_3$ (peptide disclosed as SEQ ID NO: 99)-EGFP and pBI-SS$^{tob}$(AlaPro)$_4$(YK)$_{20/8/4}$EGFP (peptide disclosed as SEQ ID NO: 6), pBI-SS$^{tob}$(YK)$_{20/8/4}$(AlaPro)$_4$EGFP (peptide disclosed as SEQ ID NO: 6) plasmids.

Figure 39:
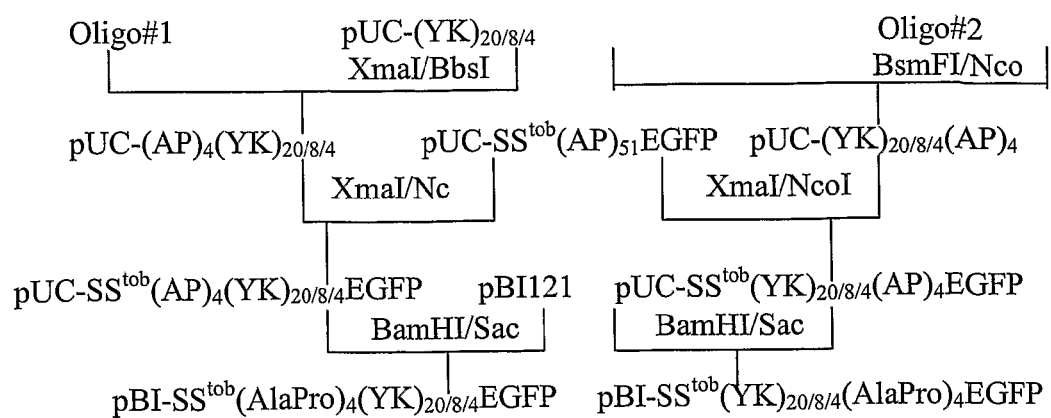
FIG. 39 is a flowchart of oligonucleotide construction.

The oligonucleotide sets were ligated into pUC-(YK)$_{20}$, pUC-(YK)$_8$, and pUC-(YK)$_4$, respectively (See FIG. 39). The resulting (AlaPro)$_4$(YK)$_{20/8/4}$ (Peptide disclosed as SEQ ID NO: 6) and (YK)$_{20/8/4}$(AlaPro)$_3$ (peptide disclosed as SEQ ID NO: 99) fragments were ligated into pUC-SS$^{tob}$(AP)$_{51}$EGFP (peptide disclosed as SEQ ID NO: 100) and replace the (AP)$_{51}$ (SEQ ID NO: 100) gene. The SS$^{tob}$(AlaPro)$_4$(YK)$_{20/8/4}$EGFP (peptide disclosed as SEQ ID NO: 6) and SS$^{tob}$(YK)$_{20/8/4}$(AlaPro)$_3$ (peptide disclosed as SEQ ID NO: 99) fragments were finally ligated into the plant transformation vector pBI121 vector to give plasmids: pBI-SS$^{tob}$(AlaPro)$_4$(YK)$_{20/8/4}$EGFP (peptide disclosed as SEQ ID NO: 6) and pBI-SS$^{tob}$(YK)$_{20/8/4}$(AlaPro)$_4$EGFP (peptide disclosed as SEQ ID NO: 6).

3). Transformation of above gene cassettes into tobacoo BY2 suspension cultured cells.

Above-modified pBI plasmids were transformed into Agrobacterium; transformants were selected by kanamycin and streptomycin resistance. The agrobacteria were then used to infect suspension cultured tobacco BY2 cells. The transformed tobacco cells were selected for kanamycin resistance and cultured in SH media for 20 days at room temperature.

4). Fusion protein isolation and purification.

Culture medium from the transformed tobacco cells was collected and concentrated under vacuum at 28° C. The concentrated media was adjusted with NaCl to 2M and loaded on a Butyl-sepharose HIC column. The column was eluted with a gradient starting with 2M NaCl and ending with water. Green fractions were collected and freeze-dried. The crude fusion proteins were then purified on a Superose-12 preparative gel filtration column. Green fractions were either repurified on a C-4 reverse phased semi-preparative column in a gradient from 0.1% TFA (aq) to 100% of 80% acetonitrile in 0.1% TFA (aq) in 100 minutes, or concentrated and desalted on centricon spin columns of cutting size of 5 kDa.

5). Removal of EGFP from the isolated fusion proteins.

EGFP was removed from fusion proteins (AlaPro)$_4$(YK)$_{20/8/4}$EGFP by tryptic digestion in a solution of 2% ammonium bicarbonate, 5 mM CaCl$_2$. The glycomodules were isolated from the solution by size exclusion chromatography on the Superose-12 column, and further purified on C-4 reverse phased semipreparative column using a 60 min gradient from starting with 100% 0.1% TFA (aq) and ending with 80% acetonitrile in 0.1% TFA (aq).

6). Hyp-glycoside profiles of fusion proteins.

7.2 mg of (AlaPro)$_4$(YK)$_{20}$EGFP was hydrolyzed in 0.44 N NaOH at 105° C. for 18 hr. The hydrolysate was neutralized and freeze-dried.

7). Sugar analysis of fusion proteins.

One-hundred µg of fusion proteins were dissolved in 200 µl of 2N TFA and heated at 121° C. for 2 hrs. The hydrolysate was then reduced and acetylated as described before.

8). Cross-linking reaction of glycomodules and fusion proteins.

Cross-linking reactions were carried out in citrate buffer with H$_2$O$_2$ and pI 4.6 extensin peroxidase as described before.

The reaction mixtures were then size-fractionated on an analytical Superose-6 column, which was monitored for UV absorbance at 220 nm.

Results

1). Sequences of Each Construct

The pUC-derived plasmids were sequenced using a M13 forward primer (see construct sequences in A below).

```
A. (AP)4(YK)20EGFP (peptide disclosed as SEQ ID NO: 6)
A   P   A   P   A   P   A   P   S   P   P   P   P   Y   Y
GCT CCA GCA CCT GCC CCA GCC [CCA TCA CCA CCA CCA CCT TAC TAC Y   K   S   P   P   P   P   S   P                       (SEQ ID NO: 101)
TAC AAG TCT CCT CCT CCC CCA TCA CCA]20 EGFP              (SEQ ID NO: 101)

B. (AP)4(YK)8EGFP (peptide disclosed as SEQ ID NO: 6)
A   P   A   P   A   P   A   P   S   P   P   P   P   Y   Y
GCT CCA GCA CCT GCC CCA GCC [CCA TCA CCA CCA CCA CCT TAC TAC Y   K   S   P   P   P   P   S   P                       (SEQ ID NO: 103)
TAC AAG TCT CCT CCT CCC CCA TCA CCA]8 EGFP               (SEQ ID NO: 104)

C. (AP)4(YK)4EGFP (SEQ ID NO: 6)
A   P   A   P   A   P   A   P   S   P   P   P   P   Y   Y
GCT CCA GCA CCT GCC CCA GCC [CCA TCA CCA CCA CCA CCT TAC TAC

Y   K   S   P   P   P   P   S   P                       (SEQ ID NO: 105)
TAC AAG TCT CCT CCT CCC CCA TCA CCA]4 EGFP               (SEQ ID NO: 106)
```

2). Monosaccharide Composition

Neutral sugar analyses and uronic acid assays showed that $(AP)_4(YK)_{20}$ (peptide disclosed as SEQ ID NO: 6) was mainly arabinosylated, but also contained Rha, Ara, Gal, and GlcUA.

TABLE 19

Monosaccharide composition of $(AP)_4(YK)_{20}$EGFP
(peptide disclosed as SEQ ID NO: 6)

| Monosaccharide | $(AP)_4(YK)_{20}$EGFP (peptide disclosed as SEQ ID NO: 6) Molar percentage |
|---|---|
| Rha | 1.5 |
| Ara | 80.2 |
| Gal | 11.7 |
| GlcUA | 6.5 |

3). Hyp-Glycoside Profile.

The Hyp-glycoside profile of $(AlaPro)_4(YK)_{20}$EGFP (peptide disclosed as SEQ ID NO: 6) showed that the glycoprotein was mainly glycosylated with arabinosides. The molar percentage of Hyp-polysaccharide was in consistent with the molar percentage of Hyp flanked by Ala residues to the total Hyp, based on the gene sequence, implying that the Ala-Hyp repeat motifs were the sites of arabinogalactan polysaccharide addition.

TABLE 20

Hy-glycoside profile of $(AlaPro)_4(YK)_{20}$EGFP
(peptide disclosed as SEQ ID NO: 6)

| Hyp Type | Molar % |
|---|---|
| Hyp-polysaccharide | 4.86 |
| Hyp-Ara$_4$ | 45.67 |
| Hyp-Ara$_3$ | 29.49 |
| Hyp-Ara$_2$ | 9.71 |
| Hyp-Ara | 7.68 |
| Hyp | 2.60 |

4). Cross-Linking.

Figure 40:
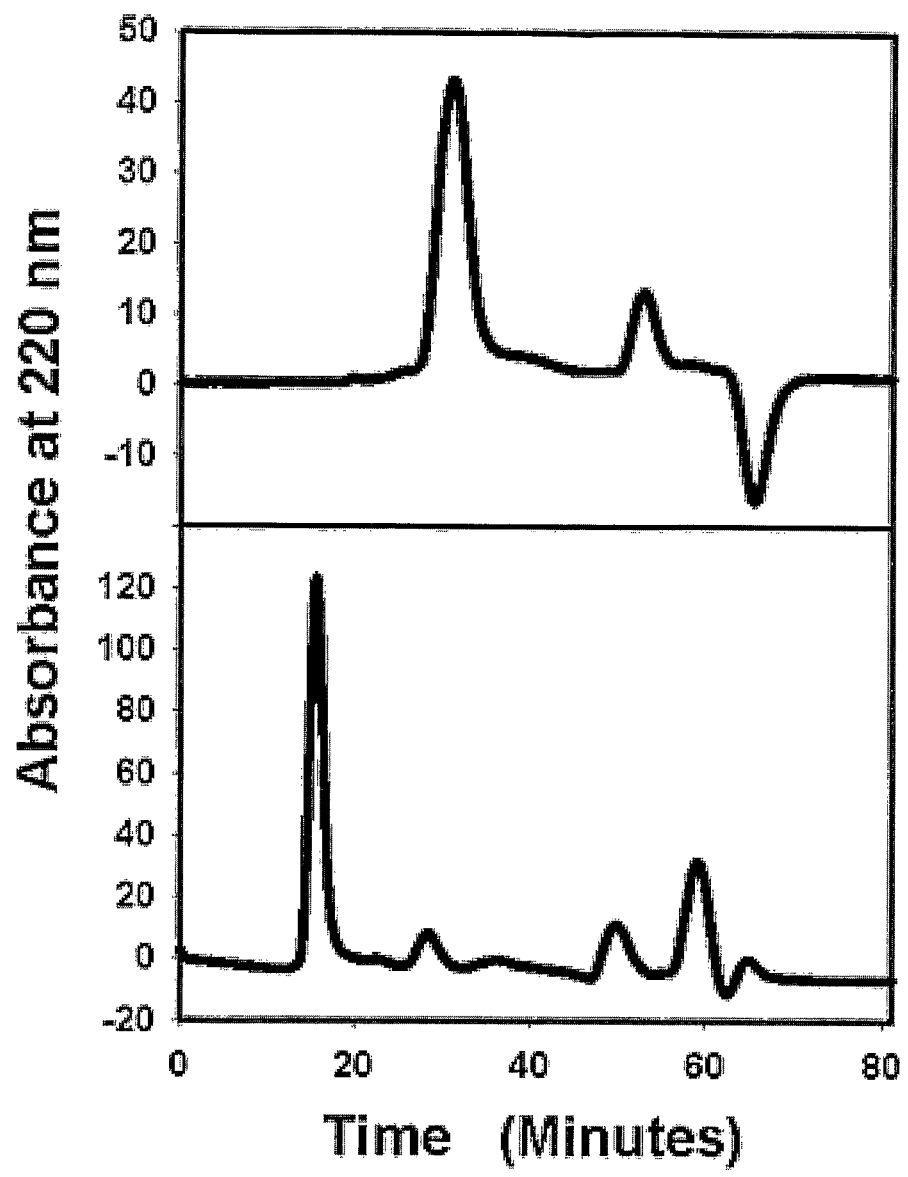
FIG. 40 shows size exclusion chromatography before (top frame) and after (bottom frame) 30 minutes of crosslinking of (AP)$_4$(YK)$_{20}$ (peptide disclosed as SEQ ID NO: 6) catalyzed by extensin peroxidase.

FIG. 40 shows size exclusion chromatography before (top frame) and after (bottom frame) 30 minutes of crosslinking of $(AP)_4(YK)_{20}$ (peptide disclosed as SEQ ID NO: 6) catalyzed by extensin peroxidase. Monomeric $(AP)_4(YK)_{20}$ (peptide disclosed as SEQ ID NO: 6) eluted at 37 minutes in the top panel. As monomeric $(AP)_4(YK)_{20}$ (peptide disclosed as SEQ ID NO: 6) was crosslinked, it increased in size. After 30 minutes $(AP)_4(YK)_{20}$ (peptide disclosed as SEQ ID NO: 6) was polymerized and voided the column (18 min).

Figure 41:
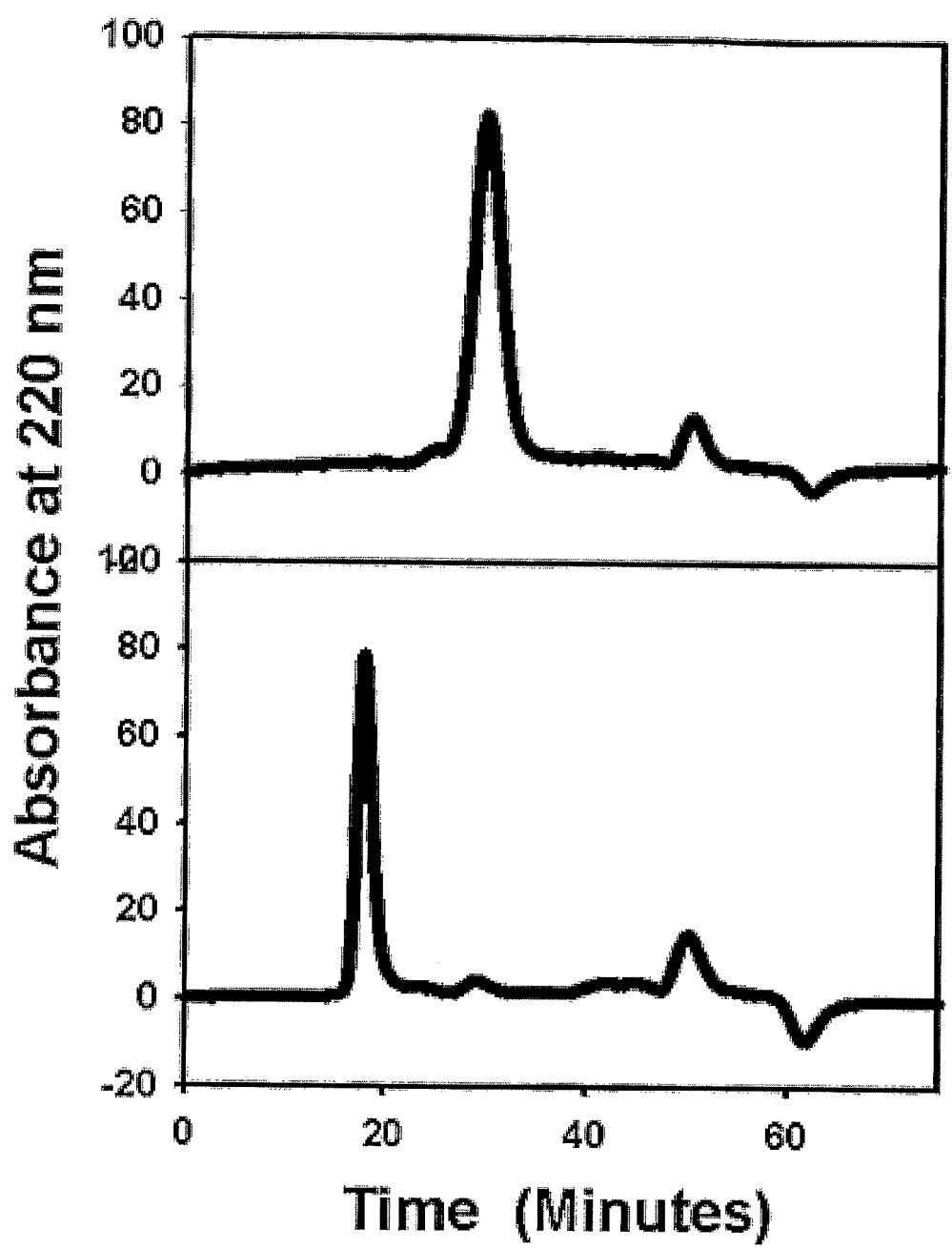
FIG. 41 shows chromatographs of the cross-linking reaction of (AP)$_4$(YK)$_{20}$EGFP (peptide disclosed as SEQ ID NO: 6).

FIG. 41 shows chromatographs of the cross-linking reaction of $(AP)_4(YK)_{20}$EGFP (peptide disclosed as SEQ ID NO: 6). The upper and lower figures showed the size shift of $(AP)_4(YK)_{20}$EGFP (peptide disclosed as SEQ ID NO: 6) after crosslinked for 0 minutes and 30 minutes.

$(AP)_4(YK)_8$ (peptide disclosed as SEQ ID NO: 6), and $(AP)_4(YK)_4$ (peptide disclosed as SEQ ID NO: 6) were also crosslinked by extensin peroxidase, although the rates of crosslinking were slower.

Example 7

Construction of Genes Encoding Cross-Linkable Human Elastin-Arabinogalactan Protein Fusion Proteins Methods I. Design of Oligonucleotides Encoding the Human Elastin Motifs and Repetitive Ala-Pro.

A set of oligonucleotides was designed based on the codons favored by tobacco cells. The oligonucleotide set encoded four repeats of human elastin motif Val-Pro-Gly-Val-Gly (SEQ ID NO: 86) (Reiersen, et al. 1998) which were evenly spaced by an AGP motif (three repeats of Ala-Pro) (Tan, et al. 2003).

The two sticky ends were designed to anneal to the vector fragments of pUC-(YK)$_2$ or pUC-(YK)$_4$ as BbsI and BsmF1 fragments (Held, 2004). Here, YK stands for the gene encoding the sequence: Ser-Pro-Pro-Pro-Pro-Ser-Pro-Ser-Pro-Pro-Pro-Pro-Tyr-Tyr-Tyr-Lys (SEQ ID NO: 107).

Oligonucleotide set:

```
      P   S   G   V   G   V   P   G   V   G       A   P   A   P
5'-CCA TCA GGA GTA GGT [GTT CCA GGA GTT GGC]₂[GCT CCA GCA CCT
   3'-GT CCT CAT CCA [CAA GGT CCT CAA CCG]₂[CGA GGT CGT GGA
Sticky end                Elastin Motif         AGP motif A   P   A       G   V   G   V   P   G   V   G            (SEQ ID NO: 108)
GCC CCA GCC] GGT GTT GGA [GTA CCT GGT GTT GGT]₂-3'        (SEQ ID NO: 109)
CGG GGT CGG] CCA CAA CCT [CAT GGA CCA CAA CCA]₂ GGT A-5'  (SEQ ID NO: 110)
                          Elastin Motif      Sticky end
```

II. Construction of plasmids pUC-(YK$_2$-E$_2$AE$_2$)$_4$, pUC-(YK$_4$-E$_2$AE$_2$)$_4$, pUC-(YK$_2$-E$_2$AE$_4$AE$_2$)$_2$, and pUC-(YK$_4$-E$_2$AE$_4$AE$_2$)$_2$. (Note: abbreviations E$_2$AE$_2$ are E: elastin motif; A: AGP motif)

1. Construction of plasmid pUC-E$_2$AE$_2$ and pUC-E$_2$AE$_4$AE$_2$

Plasmid pUC-YK$_8$ was digested by BbsI and BsmFl to remove the YK$_8$ gene (Held, 2004).

Fifty ng of above set of oligonucleotides were annealed to each other in 1× ligase buffer and ligated to the above pUC vector. The formed plasmid was named pUC-E$_2$AE$_2$. The sequence of E$_2$AE$_2$ was verified by DNA sequencing.

Plasmid pUC-E$_2$AE$_2$ was digested by two sets of restriction enzymes BbsII/ScaI and BsmFl/ScaI, respectively. The 1.1 kb BsmFl-ScaI fragment and 1.8 kb BbsI-ScaI fragments were ligated to each other to form double repeats of the gene cassette E$_2$AE$_2$ (FIG. 1) (Held, et al. 2004). The corresponding plasmid was named pUC-E$_2$AE$_4$AE$_2$. The sequence of E$_2$AE$_4$AE$_2$ was confirmed by DNA sequencing.

Figure 42:
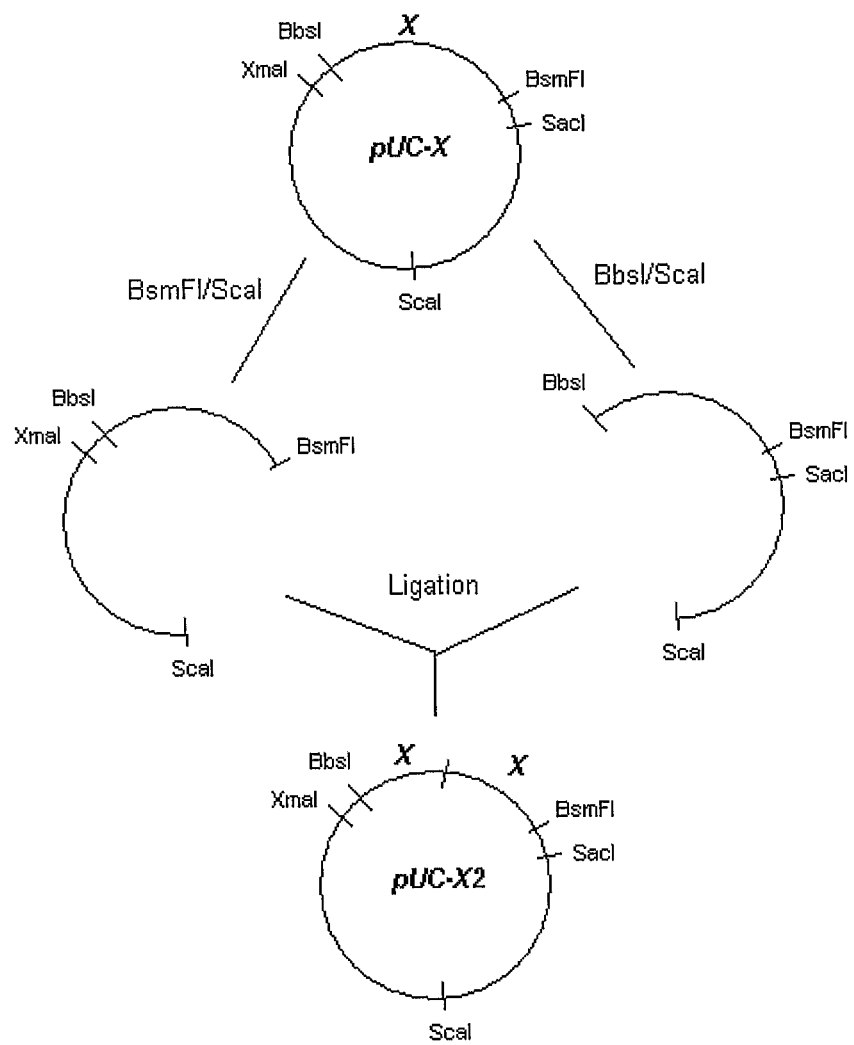
FIG. 42 shows a flow chart for gene construction.

FIG. 42 shows a flow chart for gene construction. X represented for the desired gene. In this project, X can be E$_2$AE$_2$, or YK$_2$, or YK$_4$. The ligation could be between two same genes, or between two different genes.

2. Construction of plasmids pUC-YK$_2$-E$_2$AE$_2$, pUC-YK$_4$-E$_2$AE$_2$, pUC-YK$_2$-E$_2$AE$_4$AE$_2$, and pUC-YK$_4$-E$_2$AE$_4$AE$_2$ a). By using the same strategy shown in FIG. 42, the BsmFl-ScaI fragment of pUC-YK$_2$ (Held 2004), containing the YK$_2$ gene was ligated with the BbsI-ScaI fragment of pUC-E$_2$AE$_2$ and pUC-E$_2$AE$_4$AE$_2$, respectively, which led to the formation of pUC-YK$_2$-E$_2$AE$_2$ and pUC-YK$_2$-E$_2$AE$_4$AE$_2$.

b). As shown in FIG. 42, the BsmFl-ScaI fragment of pUC-YK$_4$ (Held, 2004), containing the YK$_4$ gene was ligated with the BbsI-ScaI fragment of pUC-E$_2$AE$_2$ and pUC-E$_2$AE$_4$AE$_2$, respectively, which lead to the formation of pUC-YK$_4$-E$_2$AE$_2$ and pUC-YK$_4$-E$_2$AE$_4$AE$_2$. The purpose of constructing genes encoding different sized cross-linking motifs and elastin/AGP motifs was to test the differences of physical properties between them. All the genes were confirmed by DNA sequencing.

3. Construction of plasmids pUC-(YK$_2$-E$_2$AE$_2$)$_4$, pUC-(YK$_4$-E$_2$AE$_2$)$_4$, pUC-(YK$_2$-E$_2$AE$_4$AE$_2$)$_2$, and pUC-(YK$_4$-E$_2$AE$_4$AE$_2$)$_2$.

a). By using the method shown in FIG. 42, pUC-YK$_2$-E$_2$AE$_2$, pUC-YK$_2$-E$_2$AE$_4$AE$_2$, pUC-YK$_4$-E$_2$AE$_2$, and pUC-YK$_4$-E$_2$AE$_4$AE$_2$ were dimerized, respectively, with themselves. The desired gene sizes of (YK$_2$-E$_2$AE$_4$AE$_2$)$_2$ and (YK$_4$-E$_2$AE$_4$AE$_2$)$_2$ were about 600 and 800 bps, respectively, which were long enough for expression by tobacco cells. The corresponding plasmids were named pUC-(YK$_2$-E$_2$AE$_4$AE$_2$)$_2$ and pUC-(YK$_4$-E$_2$AE$_4$AE$_2$)$_2$.

b). The obtained pUC-(YK$_2$-E$_2$AE$_2$)$_2$ and pUC-(YK$_4$-E$_2$AE$_2$)$_2$ were further dimerized by the same method shown above, respectively. The formed pUC-(YK$_2$-E$_2$AE$_2$)$_4$, pUC-(YK$_4$-E$_2$AE$_2$)$_4$ had the gene cassettes of sizes about 800 and 1200 bps, respectively.

All the sequences were confirmed by DNA sequencing.

III. Construction of plasmids pBI-SS$^{tob}$-(YK$_2$-E$_2$AE$_2$)$_4$-EGFP, pBI-SS$^{tob}$-(YK$_4$-E$_2$AE$_2$)$_4$-EGFP, pBI-SS$^{tob}$-(YK$_2$-E$_2$AE$_4$AE$_2$)$_2$-EGFP, and pBI-SS$^{tob}$-(YK$_4$-E$_2$AE$_4$AE$_2$)$_2$-EGFP.

1. The constructed gene fragments in pUC-(YK$_2$-E$_2$AE$_2$)$_4$, pUC-(YK$_4$-E$_2$AE$_2$)$_4$, pUC-(YK$_2$-E$_2$AE$_4$AE$_2$)$_2$, and pUC-(YK$_4$-E$_2$AE$_4$AE$_2$)$_2$ were removed from the plasmids by the restriction enzymes XmaI and NcoI, and ligated into pUC-SS$^{tob}$-(AP)$_{11}$-EGFP by replacing the (AP)$_{11}$ fragment (flanked by XmaI and NcoI restriction sites), respectively (Shpak, et al., 1999, 2001, Tan, et al 2003, Tan 2003). The four new plasmids were named pUC-SS$^{tob}$-(YK$_2$-E$_2$AE$_2$)$_4$-EGFP, pUC-SS$^{tob}$-(YK$_4$-E$_2$AE$_2$)$_4$-EGFP, pUC-SS$^{tob}$-(YK$_2$-E$_2$AE$_4$AE$_2$)$_2$-EGFP, and pUC-SS$^{tob}$-(YK$_4$-E$_2$AE$_4$AE$_2$)$_2$-EGFP, respectively.

2. The gene cassettes in above four new pUC plasmids were further removed from original plasmids by BamHI and SacI, and ligated into pBI 121 between the BamHI and SacI restriction sites (Shpak, et al., 1999, 2001, Tan, et al 2003, Tan 2003). Then, we obtained the plant transformation plasmids: pBI-SS$^{tob}$-(YK$_2$-E$_2$AE$_2$)$_4$-EGFP, pBI-SS$^{tob}$-(YK$_4$-E$_2$AE$_2$)$_4$-EGFP, pBI-SS$^{tob}$-(YK$_2$-E$_2$AE$_4$AE$_2$)$_2$-EGFP, and pBI-SS$^{tob}$-(YK$_4$-E2AE4AE2)$_2$-EGFP.

All gene sequences were confirmed by DNA sequencing with a primer derived from tobacco extensin signal sequence.

IV. Transfer the genes into tobacco cells.

1. Each 100 ng of above-modified pBI plasmid was transformed into *Agrobacterium* by the Freeze-thaw method (An, et al. 1988). The positive colonies of *agrobacterium* were selected by Kanamycin/Streptomycin resistance.

2. Overnight-growed transformed *agrobacteria* were used to co-culture with 4-day cultured tobacco cells (in SH media) at 28° C. for 2 days.

3. The infected tobacco cells were washed 4 times with SH media to remove the excess *agrobacteria*. The tobacco cells were spread on SH solid plates with Kanamycin (100 μg/ml) and Timentin (200 μg/ml).

The following documents, some of which have been cited and referred to herein, are considered part of this disclosure and are incorporated herein by reference in their entirety.

Albersheim, P. et al. "A method for the analysis of sugars in plant cell-wall polysaccharides by gas liquid chromatography." *Carbohyd. Res.* 5 (1967): 340-45.

An, G. et al. "Binary Vectors." Dordrecht, Netherlands: Martinus Nijhoff, 1988.1-19.

Benhamou, N. et al. "Differential accumulation of hydroxyproline-rich glycoproteins in bean root nodule cells infected with a wild-type strain or C4-dicarboxylic acid mutant of *Rhizobium leguminosarum* bv. *phaseoli*." *Planta* 184 (1991): 457-67.

Bergman, T., M. Cariquist, and H. Jornvall. "Amino Acid Analysis by High Performance Liquid Chromatography of Phenylthiocarbamyl Derivatives." Ed. B. Wittmann-Liebold. Berlin: Springer Verlag, 1986. 45-55.

Blumenkrantz, N. and G. Asboe-Hansen. "New methods for quantitative determination of uronic acids." *Anal. Biochem.* 54 (1973): 484-89.

Brady, J. D. and S. C. Fry. "Formation of di-isodityrosine and loss of isodityrosine in the cell walls of tomato cell-suspension cultures treated with fungal elicitors or H2O2." *Plant Physiol.* 115.1 (1997): 87-92.

Brady, J. D., I. H. Sadler, and S. C. Fry. "Di-isodityrosine, a novel tetrameric derivative of tyrosine in plant cell wall proteins: a new potential cross-link." *Biochem. J.* 315 (1996): 323-27.

Brady, J. D., I. H. Sadler, and S. C. Fry. "Pulcherosine, an oxidatively coupled trimer of tyrosine in plant cell walls: its role in cross-link formation." *Phytochemistry* 47 (1998): 349-53.

Brownleader, M. D. et al. "Purification and partial characterization of tomato extensin peroxidase." *Plant Physiol.* 109 (1995): 1115-23.

Carpita, N. C. and D. M Gibeaut. "Structural models of primary cell walls in flowering plants: consistency of molecular structure with the physical properties of the walls during growth." *Plant J.* 3 (1993): 1-30.

Cassab, G. I. "Arabinogalactan proteins during the development of soybean (*Glycine max*) root nodules." *Planta* 168 (1986): 441-46.

Chen, J. and J. E. Varner. "An extracellular matrix protein in plants: characterization of a genomic clone for carrot extensin." *EMBO J.* 4 (1985): 2145-51.

Corbin, D. R., N. Sauer, and C. J. Lamb. "Differential regulation of a hydroxyproline-rich glycoprotein gene family in wounded and infected plants." *Mol. Cell. Biol.* 7 (1987): 4337-44.

De Loose, M. et al. "The extensin signal peptide allows secretion of a heterologous protein from protoplasts." *Gene* 99 (1991): 95-100.

Epstein, L. and D. T. A. Lamport. "An intramolecular linkage involving isodityrosine in extensin." *Photochemistry* 23 (1984): 1241-46.

Everdeen, D. S. et al. "Enzymic crosslinkage of monomeric extensin precursors in vitro." *Plant Physiol.* 87 (1988): 616-21.

Fong, C. et al. "A gymnosperm extensin contains the serine-tetrahydroxyproline motif." *Plant Physiol.* 99 (1992): 548-52.

Franssen, H. J. et al. "Characterization of cDNA for nodulin-75 of soybean: A gene product involved in early stages of root nodule development." *Proc. Natl. Acad. Sci.* 84 (1987): 4495-99.

Frueauf, J. B. et al. "Peptides isolated from cell walls of *Medicago truncatula* nodules and uninfected root." *Phytochemistry* 55.5 (2000): 429-38.

Fry, S. C. "Isodityrosine, a new cross-linking amino acid from plant cell-wall glycoprotein." *Biochem. J.* 204 (1982): 449-55.

Fry, S. C. "Formation of isodityrosine by peroxidase isozymes." *J. Exp. Bot.* 190 (1987): 853-62.

Fujimoto, D. Horiuchi K. and Hirama M. *Biochem. Biophys, Res. Commun.* 99 (1981): 637-43.

Fujimoto, D. Horiuchi K. and Hirama M. *Biochem. Biophys, Res. Commun.* 99 (1981): 637-43.

Goodenough, U. W. et al. "Crystals of the *Chlamydomonas reinhardtii* cell wall: polymerization, depolymerization and purification of glycoprotein monomers." *J. Cell Biol.* 103 (1986): 405-17.

Hall, Q. and M. C. Cannon. "The cell wall hydroxyproline-rich glycoprotein RSH is essential for normal embryo development in *Arabidopsis*." *Plant Cell* 14 (2002): 1161-72.

Han, Y. et al. "Hydroxyproline-rich glycoproteins expressed during stress responses in cassaya." *Euphytica* 120 (2001): 59-70.

Heckman, J. W., B. T. Terhune, and D. T. A. Lamport. "Characterization of native and modified extensin monomers and oligomers by electron microscopy and gel filtration." *Plant Physiol.* 86 (1988): 848-56.

Held M A, Tan L, Kamyab A, Hare M, Shpak E, and Kieliszewski M J (2004) Di-isodityrosine is the intermolecular crosslink of isodityrosine-rich extensin analogs crosslinked in vitro. *J. Biol. Chem.* 279: 55474-55482.

Hirsinger, Cathy et al. "The tobacco extensin gene Ext 1.4 is expressed in cells submitted to mechanical constraints and in cells proliferating under hormone control." *J. Exp. Bot.* 50 (1999): 343-55.

Jackson, P. A. P. et al. "Rapid deposition of extensin during the elicitation of grapevine callus cultures is specifically catalyzed by a 40-kilodalton peroxidase." *Plant Physiol.* 127 (2001): 1065-76.

Keegstra, K. et al. "The structure of plant cell walls. III. A model of the walls of suspension-cultured sycamore cells based on the interconnections of the macromolecular components." *Plant Physiol.* 51 (1973): 188-96.

Kerr, T. and I. W. Bailey. "The cambium and its derivative tissues. X Structure, optical properties and chemical composition of the so-called middle lamella." *Journal of the Arnold Arboretum* 15 (1934): 327-49.

Kieliszewski, M. J. "The latest hype on Hyp-O-glycosylation codes." *Phytochemistry* 57.3 (2001): 319-23.

Kieliszewski, M. J. et al. "A histidine-rich extensin from *Zea mays* is an arabinogalactan protein." *Plant Physiol.* 99 (1992): 538-47.

Kieliszewski, M. J. and D. T. A. Lamport. "Extensin: repetitive motifs, functional sites, posttranslational codes and phylogeny." *Plant J.* 5 (1994): 157-72.

Kieliszewski, M. J. et al. "Tandem mass spectrometry and structural elucidation of glycopeptides from a hydroxyproline-rich plant cell wall glycoprotein indicate that contiguous hydroxyproline residues are the major sites of hydroxyproline-O-arabinosylation." *J. Biol. Chem.* 270 (1995): 2541-49.

Knupp, C. and J. M. Squire. "Molecular packing in network-forming collagens." *The Scientific World* 3 (2003): 558-77.

Lamport, D. T. A. "Oxygen fixation into hydroxyproline of plant cell wall protein." *J. Biol. Chem.* 238 (1963): 1438-40.

Lamport, D. T. A. "The protein component of primary cell walls." *Adv. Bot. Res.* 2 (1965): 151-218.

Lamport, D. T. A. "Hydroxyproline-β-glycosidic linkage of the plant cell wall glycoprotein extensin." *Nature* 216 (1967): 1322-24.

Lamport, D. T. A. "The isolation and partial characterization of hydroxyproline-rich glycopeptides obtained by enzymic degradation of primary cell walls." *Biochemistry* 8 (1969): 1155-63.

Lamport, D. T. A. "Is the primary cell wall a protein-glycan network?" *1st International Protoplast Colloquium, Versailles. I.N.R.A.* (1973): 27-31.

Lamport, D. T. A. "Structure, Biosynthesis and Significance of Cell Wall Glycoproteins." Ed. F. A. Loewus and V. C. Runeckles. New York: Plenum Publishing Corp., 1977. 79-115.

Lamport, D. T. A. and L. Epstein. "A new model for the primary cell wall: a concatenated extensin-cellulose network." *Proc. Ann. Plant Biochem. & Physiol. Symp. Columbia-Missouri.* 2 (1983): 73-83.

Lamport, D. T. A., L. Katona, and S. Roerig. "Galactosyl serine in extensin." *Biochem. J.* 133 (1973): 125-31.

Lamport, D. T. A. and D. H. Miller. "Hydroxyproline arabinosides in the plant kingdom." *Plant Physiol.* 48 (1971): 454-56.

Lamport, D. T. A. and D. H. Northcote. "Hydroxyproline in primary cell walls of higher plants." *Nature* 188 (1960): 665-66.

Lamport, D. T. A. and D. H. Northcote. "The use of tissue cultures for the study of plant cell walls." *Biochem. J.* 76 (1960): 52P.

Lewis, R. V. et al. "Expression and purification of a spider silk protein: a new strategy for producing repetitive proteins." *Protein Expression Purif.* 7 (1996): 400-06.

Li, B and Daggett, V (2002) Molecular basis for the extensibility of elastin. *J. Muscle Res. and Cell Motility.* 23: 561-573

McCormick, S. et al. "Leaf disc transformation of cultivated tomato (*L. esculentum*) using *Agrobacterium tumefaciens.*" *Plant Cell Reports* 5 (1986): 81-84.

McGrath, K. P. et al. "Chemical and biosynthetic approaches to the production of novel polypeptide materials." *Biotechnol. Prog.* 6 (1990): 186-92.

Merkouropoulos, G. and A. H. Shirsat. "The unusual *Arabidopsis* extensin gene atExt1 is expressed throughout plant development and is induced by a variety of biotic and abiotic stresses." *Planta* 217 (2003): 356-66.

Merkouropoulos, Georgios, David C. Barnett, and Anil H. Shirsat. "The *Arabidopsis* extensin gene is developmentally regulated, is induced by wounding, methyl jasmonate, abscisic, and salicylic acid and codes for a protein with unusual motifs." *Planta* 208.2 (1999): 212-19.

Mort, A. J. "Partial Characterization of Extensin by Selective Degradation of Cell Walls." Diss. Michigan State University, 1978.

Mort, A. J. and D. T. A. Lamport. "Anhydrous hydrogen fluoride deglycosylates glycoproteins." *Analyt. Biochem.* 82 (1977): 289-309.

Price, N. J. et al. "A Biochemical and Molecular Charaterization of LEP1, an Extensin Peroxidase from Lupin." J. Biol. Chem. 278.42 (2003): 41389-99.

Qi, X. et al. "Solubilization and partial characterization of extensin fragments from cell walls of cotton suspension cultures. Evidence for a covalent cross-link between extensin and pectin." *Plant Physiol.* 108 (1995): 1691-701.

Roberts, K. "Crystalline glycoprotein cell walls of algae: Their structure, composition and assembly." *Phil. Trans. R. Soc. Lond. B* 268 (1974): 129-46.

Sanger, M. P. and D. T. A. Lamport. "A micro-apparatus for liquid hydrogen fluoride solvolysis: sugar and amino sugar composition of *Erysiphe graminis* and *Triticum aestivum* cell walls." *Analyt. Biochem.* 128 (1983): 66-70.

Schnabelrauch, L. S. et al. "Isolation of pI 4.6 extensin peroxidase from tomato cell suspension cultures and identification of Val-Tyr-Lys as putative intermolecular cross-link site." *Plant J.* 9 (1996): 477-89.

Shirsat, A. H. et al. "The *Brassica napus* extA extensin gene is expressed in regions of the plant subject to tensile stresses." *Planta* 199 (1996): 618-24.

Showalter, A. M. and D. Rumeau. "Molecular Biology of Plant Cell Wall Hydroxyproline-Rich Glycoproteins." Ed. W. S. Adair and R. P. Mecham. New York: Academic Press, 1990. 247-81.

Showalter, A. M. and J. E. Varner. "Molecular Details of Plant Cell Wall Hydroxyproline-Rich Glycoproteins." Ed. C. J. Arntzen and Ryan C. New York: Alan R Liss, 1987. 375-92.

Showalter, A. M. and J. E. Varner. "Plant Hydroxyproline-Rich Glycoproteins." Ed. J. Preiss. New York: Academic Press, 1989. 485-520.

Showalter, A. M. et al. "Tomato extensin and extensin-like cDNAs: structure and expression in response to wounding." *Plant Mol. Biol.* 16 (1991): 547-65.

Shpak, E. et al. "Contiguous hydroxyproline residues direct hydroxyproline arabinosylation in *Nicotiana tabacum.*" *J. Biol. Chem.* 276 (2001): 11272-78.

Shpak, E., J. Leykam, and M. J. Kieliszewksi. "Synthetic genes for glycoprotein design and the elucidation of hydroxyproline-O-glycosylation codes." *Proc. Natl. Acad, Sci.* 96 (1999): 14736-41.

Shpak, Elena. "Synthetic Genes for the Elucidation of Hydroxyproline O-Glycosylation Codes." Diss. University of Ohio, 2000.

Shpak, Elena, Joseph F. Leykam, and Marcia J. Kieliszewski. "Synthetic genes for glycoprotein design and the elucidation of hydroxyproline-O-glycosylation codes." *Proc. Natl. Acad. Sci. U.S.A.* 96.26 (1999): 14736-41.

Smith, J. J., E. P. Muldoon, and D. T. A. Lamport. "Isolation of extensin precursors by direct elution of intact tomato cell suspension cultures." *Phytochemistry* 23 (1984): 1233-39.

Smith, J. J. et al. "Tomato extensin precursors P1 and P2 are highly periodic structures." *Phytochemistry* 25 (1986): 1021-30.

Stafstrom, J. P. and L. A. Staehelin. "The role of carbohydrate in maintaining extensin in an extended conformation." *Plant Physiol.* 81 (1986): 242-46.

Stephen C. Fry. *The Growing Plant Cell Wall: Chemical and Metabolic Analysis.* Ed. M Wilkens. Essex: Longman Scientific & Technical; John Wiley and Sons, Inc., 1988.

Tan, L. (2003) Dissertation: O-glycosylation motifs in arabinogalactan-proteins.

Tan L, Leykam J F Kieliszewski M J. "Glycosylation motifs that direct arabinogalactan addition to arabinogalactan-proteins." *Plant Physiol.* 132.3 (2003): 1362-69.

Tan, L., J. Leykam, and M. J. Kieliszewski. "Glycosylation motifs that direct arabinogalactan addition to arabinogalactan-proteins." *Plant Physiol.* 132 (2003): 1362-69.

van Holst, G.-J. and J. E. Varner. "Reinforced polyproline II conformation in a hydroxyproline-rich glycoprotein from carrot root." *Plant Physiol.* 74 (1984): 247-51.

Welinder, K. G. et al. "Structural diversity and transcription of class III peroxidases from *Arabidopsis thaliana.*" *Eur. J. Biochem.* 269 (2002): 6063-81.

Whitesides, G. M., J. P. Mathias, and C. T. Seto. "Molecular self-assembly and nanochemistry: a chemical strategy for the synthesis of nanostructures." *Science* 254 (1991): 1312-19.

Yoshiba, Yoshu et al. "Characterization of four extensin genes in *Arabidopsis thaliana* by differential gene expression under stress and non-stress conditions." *DNA Research* 8.3 (2001): 115-22.

Zhao, Z. D. et al. "Tomato LeAGP-1 arabinogalactan-protein purified from transgenic tobacco corroborates the Hyp contiguity hypothesis." *Plant J.* 31.4 (2002): 431-44.

Zhou, J., D. Rumeau, and A. M. Showalter. "Isolation and characterization of two wound-regulated tomato extensin genes." *Plant Mol. Biol.* 20 (1992): 5-17.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise defined, all technical and scientific terms used herein have the same meaning as commonly understood by one of the ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

What is claimed is:

1. A non-naturally occurring protein comprising at least one crosslinking motif comprising the amino acid sequence Tyr-X-Tyr, wherein X is chosen from Lys, Val, and Leu, and wherein the protein, in the presence of oxidizing conditions, forms at least one of intermolecular crosslinks and intramolecular crosslinks, the non-naturally occurring protein further comprising at least one arabinogalactan glycomodule comprising the sequence Xaa-Hyp-Xaa-Hyp, wherein Xaa is chosen from Ser and Ala.

2. The non-naturally occurring protein according to claim 1, wherein the at least one crosslinking motif has the sequence comprising Tyr-X-Tyr-Lys.

3. The non-naturally occurring protein according to claim 1, which comprises two or more Tyr-X-Tyr crosslinking motifs.

4. The non-naturally occurring protein according to claim 1, intermolecularly crosslinked to a non-naturally occurring protein comprising a Tyr-X-Tyr crosslinking motif.

5. The non-naturally occurring protein according to claim 1, intramolecularly crosslinked to itself.

6. The non-naturally occurring protein according to claim 1, further comprising at least one glycomodule comprising the amino acid sequence X'Hyp$_n$, wherein X' is any amino acid, and n is from 1 to about 1000.

7. The non-naturally occurring protein according to claim 6, wherein X' is chosen from Ser, Ala, Val, and Thr.

8. The non-naturally occurring protein according to claim 1, which comprises two or more X-Hyp-X-Hyp arabinogalactan glycomodules.

9. A non-naturally occurring protein capable of undergoing crosslinking and glycosylation, comprising at least one crosslinking motif comprising the amino acid sequence Tyr-X-Tyr, wherein X is chosen from any amino acid except Tyr; and at least one arabinogalactan glycomodule comprising the sequence Xaa-Hyp-Xaa-Hyp, wherein Xaa is chosen from Ser, Ala, Val and Thr;

wherein the protein, in the presence of oxidizing conditions, has at least one crosslink at a Tyr-X-Tyr motif, the at least one crosslink selected from intermolecular crosslinks and intramolecular crosslinks; and wherein the protein, in the presence of glycosylation conditions, is O-linked Hyp glycosylated.

10. The non-naturally occurring protein according to claim 9, wherein X is chosen from Lys, Leu, and Val.

11. The non-naturally occurring protein according to claim 9, further comprising at least one glycomodule comprising the amino acid sequence X'-Hyp$_n$, wherein X is selected from Ser, Ala, Val and Thr, and n is from 1 to about 1000.

12. The non-naturally occurring protein according to claim 9, intermolecularly crosslinked to a non-naturally occurring protein comprising a Tyr-X-Tyr crosslinking motif.

13. The non-naturally occurring protein according to claim 9, intramolecularly crosslinked to itself.

* * * * *

```
                         SEQUENCE LISTING

<160> NUMBER OF SEQ ID NOS: 141

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (7)
<223> OTHER INFORMATION: Hyp

<400> SEQUENCE: 1

Ser Xaa Xaa Xaa Xaa Thr Xaa Val Tyr Lys
  1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
```

-continued

```
<400> SEQUENCE: 2

Ser Xaa Xaa Xaa Xaa Val Tyr Lys Tyr Lys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (7)
<223> OTHER INFORMATION: Hyp
<220> FEATURE:
<221> NAME/KEY: MOD_RES
<222> LOCATION: (9)..(12)
<223> OTHER INFORMATION: Hyp

<400> SEQUENCE: 3

Ser Xaa Xaa Xaa Xaa Ser Xaa Ser Xaa Xaa Xaa Xaa Tyr Tyr Tyr Lys
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Tyr Lys Val Tyr Lys Val Tyr Lys Val Tyr Lys Val Tyr Lys Val
1               5                   10                  15

Tyr Lys

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Phe Leu Val Phe Leu Val Phe Leu Val Phe Leu Val Phe Leu Val
1               5                   10                  15

Phe Leu

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Pro Ala Pro Ala Pro Ala Pro
1               5
```

```
<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Tyr Tyr Lys
 1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Tyr Tyr His
 1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Tyr Tyr Ser
 1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Tyr Tyr Gln
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Tyr Tyr Asn
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 12

Tyr Tyr Tyr Tyr
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Tyr Tyr Thr
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Tyr Tyr Val
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Tyr Tyr Ile
 1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Tyr Tyr Leu
 1

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr His Tyr
 1

<210> SEQ ID NO 18
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 18

Tyr His Tyr Val
 1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr His Tyr Ser
 1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr His Tyr Thr
 1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr His Tyr Tyr
 1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr His Tyr Gln
 1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr His Tyr His
 1
```

```
<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr His Tyr Glu
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Val Tyr Lys
  1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Val Tyr Ser
  1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Val Tyr Gln
  1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Val Tyr Gly
  1

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

-continued

Tyr Val Tyr
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Val Tyr Asn
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Val Tyr His
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Val Tyr Ala
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Lys Tyr Lys
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Lys Tyr Ser
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic

```
                             -continued peptide

<400> SEQUENCE: 35

Tyr Lys Tyr Pro
 1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Lys Tyr Asn
 1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Lys Tyr Tyr
 1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Lys Tyr Gln
 1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ile Tyr Lys
 1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Ile Tyr Ala
 1

<210> SEQ ID NO 41
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Ile Tyr Ser
 1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Ile Tyr Gly
 1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Ile Tyr Asn
 1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Leu Tyr Lys
 1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Leu Tyr Ser
 1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Leu Tyr Asn
 1
```

```
<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Leu Tyr Thr
  1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Leu Tyr Ala
  1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Ser Tyr Ser
  1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Ser Tyr Ala
  1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Ser Tyr Asp
  1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 52

Tyr Ser Tyr Asn
 1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Ser Tyr Thr
 1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Pro Tyr Leu
 1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Pro Tyr Thr
 1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Pro Tyr Ser
 1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Asp Tyr Thr
 1

<210> SEQ ID NO 58
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 58

Tyr Asp Tyr Asn
 1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Glu Tyr Lys
 1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Glu Tyr Ser
 1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Tyr Gly Tyr Thr
 1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Gly Tyr Gly
 1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Gln Tyr Lys
 1
```

```
<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Gln Tyr Ser
 1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Ala Tyr Lys
 1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Phe Tyr Ser
 1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Met Tyr Lys
 1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Tyr Asn Tyr Ser
 1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69
```

Tyr Thr Tyr Ser
1

<210> SEQ ID NO 70
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ser Ala Met Gly Lys Met Ala Ser Leu Phe Ala Thr Phe Leu Val
1               5                   10                  15

Val Leu Val Ser Leu Ser Leu Ala Gln Thr Thr Arg Gly Arg Arg Pro
            20                  25                  30

Ser Pro Pro Pro Pro Phe Phe Phe Leu Ser Pro Pro Pro Pro Ser Pro
        35                  40                  45

Ser Thr Met Val Ser Lys
        50

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (7)
<223> OTHER INFORMATION: Hyp
<220> FEATURE:
<221> NAME/KEY: MOD_RES
<222> LOCATION: (9)..(12)
<223> OTHER INFORMATION: Hyp

<400> SEQUENCE: 71

Ser Xaa Xaa Xaa Xaa Ser Xaa Ser Xaa Xaa Xaa Xaa Tyr Tyr Tyr Leu
1               5                   10                  15

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(8)
<223> OTHER INFORMATION: Hyp
<220> FEATURE:
<221> NAME/KEY: MOD_RES
<222> LOCATION: (14)..(17)
<223> OTHER INFORMATION: Hyp
<220> FEATURE:
<221> NAME/KEY: MOD_RES
<222> LOCATION: (19)
<223> OTHER INFORMATION: Hyp

<400> SEQUENCE: 72

Arg Arg Pro Ser Xaa Xaa Xaa Xaa Tyr Tyr Tyr Lys Ser Xaa Xaa Xaa
1               5                   10                  15

Xaa Ser Xaa Ser
            20

```
<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp
<220> FEATURE:
<221> NAME/KEY: MOD_RES
<222> LOCATION: (5)..(8)
<223> OTHER INFORMATION: Hyp
<220> FEATURE:
<221> NAME/KEY: MOD_RES
<222> LOCATION: (14)..(17)
<223> OTHER INFORMATION: Hyp
<220> FEATURE:
<221> NAME/KEY: MOD_RES
<222> LOCATION: (19)
<223> OTHER INFORMATION: Hyp

<400> SEQUENCE: 73

Arg Arg Xaa Ser Xaa Xaa Xaa Xaa Tyr Tyr Tyr Lys Ser Xaa Xaa Xaa
 1               5                  10                  15

Xaa Ser Xaa Ser
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(8)
<223> OTHER INFORMATION: Hyp
<220> FEATURE:
<221> NAME/KEY: MOD_RES
<222> LOCATION: (14)..(17)
<223> OTHER INFORMATION: Hyp
<220> FEATURE:
<221> NAME/KEY: MOD_RES
<222> LOCATION: (19)
<223> OTHER INFORMATION: Hyp

<400> SEQUENCE: 74

Arg Arg Pro Ser Xaa Xaa Xaa Xaa Tyr Tyr Tyr Leu Ser Xaa Xaa Xaa
 1               5                  10                  15

Xaa Ser Xaa Ser
            20

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (7)
<223> OTHER INFORMATION: Hyp
<220> FEATURE:
```

```
<221> NAME/KEY: MOD_RES
<222> LOCATION: (9)..(12)
<223> OTHER INFORMATION: Hyp
<220> FEATURE:
<221> NAME/KEY: MOD_RES
<222> LOCATION: (18)..(21)
<223> OTHER INFORMATION: Hyp
<220> FEATURE:
<221> NAME/KEY: MOD_RES
<222> LOCATION: (23)
<223> OTHER INFORMATION: Hyp
<220> FEATURE:
<221> NAME/KEY: MOD_RES
<222> LOCATION: (25)..(28)
<223> OTHER INFORMATION: Hyp

<400> SEQUENCE: 75

Ser Xaa Xaa Xaa Xaa Ser Xaa Ser Xaa Xaa Xaa Phe Phe Phe Lys
 1               5                  10                  15

Ser Xaa Xaa Xaa Xaa Ser Xaa Ser Xaa Xaa Xaa
             20                  25

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (7)
<223> OTHER INFORMATION: Hyp

<400> SEQUENCE: 76

Ser Xaa Xaa Xaa Xaa Thr Xaa Val Tyr Lys
 1               5                  10

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Hyp

<400> SEQUENCE: 77

Thr Xaa Val Tyr Lys
 1               5

<210> SEQ ID NO 78
<211> LENGTH: 240
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (7)
<223> OTHER INFORMATION: Hyp
```

```
<220> FEATURE:
<221> NAME/KEY: MOD_RES
<222> LOCATION: (12)..(15)
<223> OTHER INFORMATION: Hyp
<220> FEATURE:
<221> NAME/KEY: MOD_RES
<222> LOCATION: (17)
<223> OTHER INFORMATION: Hyp
<220> FEATURE:
<221> NAME/KEY: MOD_RES
<222> LOCATION: (22)..(25)
<223> OTHER INFORMATION: Hyp
<220> FEATURE:
<221> NAME/KEY: MOD_RES
<222> LOCATION: (77)..(80)
<223> OTHER INFORMATION: Hyp
<220> FEATURE:
<221> NAME/KEY: MOD_RES
<222> LOCATION: (82)..(85)
<223> OTHER INFORMATION: Hyp
<220> FEATURE:
<221> NAME/KEY: MOD_RES
<222> LOCATION: (87)..(90)
<223> OTHER INFORMATION: Hyp
<220> FEATURE:
<221> NAME/KEY: MOD_RES
<222> LOCATION: (92)..(95)
<223> OTHER INFORMATION: Hyp
<220> FEATURE:
<221> NAME/KEY: MOD_RES
<222> LOCATION: (97)..(100)
<223> OTHER INFORMATION: Hyp
<220> FEATURE:
<221> NAME/KEY: MOD_RES
<222> LOCATION: (102)..(105)
<223> OTHER INFORMATION: Hyp
<220> FEATURE:
<221> NAME/KEY: MOD_RES
<222> LOCATION: (107)..(110)
<223> OTHER INFORMATION: Hyp
<220> FEATURE:
<221> NAME/KEY: MOD_RES
<222> LOCATION: (112)..(115)
<223> OTHER INFORMATION: Hyp
<220> FEATURE:
<221> NAME/KEY: MOD_RES
<222> LOCATION: (117)..(120)
<223> OTHER INFORMATION: Hyp
<220> FEATURE:
<221> NAME/KEY: MOD_RES
<222> LOCATION: (122)..(125)
<223> OTHER INFORMATION: Hyp
<220> FEATURE:
<221> NAME/KEY: MOD_RES
<222> LOCATION: (127)..(130)
<223> OTHER INFORMATION: Hyp
<220> FEATURE:
<221> NAME/KEY: MOD_RES
<222> LOCATION: (132)..(135)
<223> OTHER INFORMATION: Hyp
<220> FEATURE:
<221> NAME/KEY: MOD_RES
<222> LOCATION: (137)..(140)
<223> OTHER INFORMATION: Hyp
<220> FEATURE:
<221> NAME/KEY: MOD_RES
<222> LOCATION: (142)..(145)
<223> OTHER INFORMATION: Hyp
<220> FEATURE:
<221> NAME/KEY: MOD_RES
<222> LOCATION: (147)..(150)
<223> OTHER INFORMATION: Hyp
<220> FEATURE:
<221> NAME/KEY: MOD_RES
<222> LOCATION: (152)..(155)
<223> OTHER INFORMATION: Hyp
<220> FEATURE:
<221> NAME/KEY: MOD_RES
<222> LOCATION: (157)..(160)
<223> OTHER INFORMATION: Hyp
```

```
<220> FEATURE:
<221> NAME/KEY: MOD_RES
<222> LOCATION: (162)..(165)
<223> OTHER INFORMATION: Hyp
<220> FEATURE:
<221> NAME/KEY: MOD_RES
<222> LOCATION: (217)..(220)
<223> OTHER INFORMATION: Hyp
<220> FEATURE:
<221> NAME/KEY: MOD_RES
<222> LOCATION: (222)
<223> OTHER INFORMATION: Hyp
<220> FEATURE:
<221> NAME/KEY: MOD_RES
<222> LOCATION: (227)..(230)
<223> OTHER INFORMATION: Hyp
<220> FEATURE:
<221> NAME/KEY: MOD_RES
<222> LOCATION: (232)
<223> OTHER INFORMATION: Hyp
<220> FEATURE:
<221> NAME/KEY: MOD_RES
<222> LOCATION: (237)..(240)
<223> OTHER INFORMATION: Hyp

<400> SEQUENCE: 78

Ser Xaa Xaa Xaa Xaa Thr Xaa Val Tyr Lys Ser Xaa Xaa Xaa Xaa Thr
 1               5                  10                  15

Xaa Val Tyr Lys Ser Xaa Xaa Xaa Val Gly Val Pro Gly Val Gly
            20                  25                  30

Val Pro Gly Val Gly Val Pro Gly Val Gly Val Pro Gly Val Gly Val
            35                  40                  45

Pro Gly Val Gly Val Pro Gly Val Gly Val Pro Gly Val Gly Val Pro
            50                  55                  60

Gly Val Gly Val Pro Gly Val Gly Val Pro Gly Ser Xaa Xaa Xaa Xaa
 65                  70                  75                  80

Ser Xaa Xaa Xaa Xaa Ser Xaa Xaa Xaa Ser Xaa Xaa Xaa Xaa Ser
                85                  90                  95

Xaa Xaa Xaa Xaa Ser Xaa Xaa Xaa Ser Xaa Xaa Xaa Xaa Ser Xaa
            100                 105                 110

Xaa Xaa Xaa Ser Xaa Xaa Xaa Ser Xaa Xaa Xaa Xaa Ser Xaa Xaa
            115                 120                 125

Xaa Xaa Ser Xaa Xaa Xaa Xaa Ser Xaa Xaa Xaa Ser Xaa Xaa Xaa
        130                 135                 140

Xaa Ser Xaa Xaa Xaa Xaa Ser Xaa Xaa Xaa Ser Xaa Xaa Xaa Xaa
145                 150                 155                 160

Ser Xaa Xaa Xaa Xaa Val Gly Val Pro Gly Val Gly Val Pro Gly Val
                165                 170                 175

Gly Val Pro Gly Val Gly Val Pro Gly Val Gly Val Pro Gly Val Gly
            180                 185                 190

Val Pro Gly Val Gly Val Pro Gly Val Gly Val Pro Gly Val Gly Val
            195                 200                 205

Pro Gly Val Gly Val Pro Gly Ser Xaa Xaa Xaa Xaa Thr Xaa Val Tyr
            210                 215                 220

Lys Ser Xaa Xaa Xaa Xaa Thr Xaa Val Tyr Lys Ser Xaa Xaa Xaa Xaa
225                 230                 235                 240

<210> SEQ ID NO 79
<211> LENGTH: 294
<212> TYPE: PRT
<213> ORGANISM: Artificial Sequence
<220> FEATURE:
<223> OTHER INFORMATION: Description of Artificial Sequence: Synthetic
      peptide
```

-continued

```
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (7)
<223> OTHER INFORMATION: Hyp
<220> FEATURE:
<221> NAME/KEY: MOD_RES
<222> LOCATION: (12)..(15)
<223> OTHER INFORMATION: Hyp
<220> FEATURE:
<221> NAME/KEY: MOD_RES
<222> LOCATION: (17)
<223> OTHER INFORMATION: Hyp
<220> FEATURE:
<221> NAME/KEY: MOD_RES
<222> LOCATION: (22)..(25)
<223> OTHER INFORMATION: Hyp
<220> FEATURE:
<221> NAME/KEY: MOD_RES
<222> LOCATION: (77)
<223> OTHER INFORMATION: Hyp
<220> FEATURE:
<221> NAME/KEY: MOD_RES
<222> LOCATION: (79)
<223> OTHER INFORMATION: Hyp
<220> FEATURE:
<221> NAME/KEY: MOD_RES
<222> LOCATION: (81)
<223> OTHER INFORMATION: Hyp
<220> FEATURE:
<221> NAME/KEY: MOD_RES
<222> LOCATION: (83)
<223> OTHER INFORMATION: Hyp
<220> FEATURE:
<221> NAME/KEY: MOD_RES
<222> LOCATION: (85)
<223> OTHER INFORMATION: Hyp
<220> FEATURE:
<221> NAME/KEY: MOD_RES
<222> LOCATION: (87)
<223> OTHER INFORMATION: Hyp
<220> FEATURE:
<221> NAME/KEY: MOD_RES
<222> LOCATION: (89)
<223> OTHER INFORMATION: Hyp
<220> FEATURE:
<221> NAME/KEY: MOD_RES
<222> LOCATION: (91)
<223> OTHER INFORMATION: Hyp
<220> FEATURE:
<221> NAME/KEY: MOD_RES
<222> LOCATION: (93)
<223> OTHER INFORMATION: Hyp
<220> FEATURE:
<221> NAME/KEY: MOD_RES
<222> LOCATION: (95)
<223> OTHER INFORMATION: Hyp
<220> FEATURE:
<221> NAME/KEY: MOD_RES
<222> LOCATION: (97)
<223> OTHER INFORMATION: Hyp
<220> FEATURE:
<221> NAME/KEY: MOD_RES
<222> LOCATION: (99)
<223> OTHER INFORMATION: Hyp
<220> FEATURE:
<221> NAME/KEY: MOD_RES
<222> LOCATION: (101)
<223> OTHER INFORMATION: Hyp
<220> FEATURE:
<221> NAME/KEY: MOD_RES
<222> LOCATION: (103)
<223> OTHER INFORMATION: Hyp
<220> FEATURE:
<221> NAME/KEY: MOD_RES
<222> LOCATION: (105)
<223> OTHER INFORMATION: Hyp
```

```
<220> FEATURE:
<221> NAME/KEY: MOD_RES
<222> LOCATION: (107)
<223> OTHER INFORMATION: Hyp
<220> FEATURE:
<221> NAME/KEY: MOD_RES
<222> LOCATION: (109)
<223> OTHER INFORMATION: Hyp
<220> FEATURE:
<221> NAME/KEY: MOD_RES
<222> LOCATION: (111)
<223> OTHER INFORMATION: Hyp
<220> FEATURE:
<221> NAME/KEY: MOD_RES
<222> LOCATION: (113)
<223> OTHER INFORMATION: Hyp
<220> FEATURE:
<221> NAME/KEY: MOD_RES
<222> LOCATION: (115)
<223> OTHER INFORMATION: Hyp
<220> FEATURE:
<221> NAME/KEY: MOD_RES
<222> LOCATION: (117)
<223> OTHER INFORMATION: Hyp
<220> FEATURE:
<221> NAME/KEY: MOD_RES
<222> LOCATION: (119)
<223> OTHER INFORMATION: Hyp
<220> FEATURE:
<221> NAME/KEY: MOD_RES
<222> LOCATION: (121)
<223> OTHER INFORMATION: Hyp
<220> FEATURE:
<221> NAME/KEY: MOD_RES
<222> LOCATION: (123)
<223> OTHER INFORMATION: Hyp
<220> FEATURE:
<221> NAME/KEY: MOD_RES
<222> LOCATION: (125)
<223> OTHER INFORMATION: Hyp
<220> FEATURE:
<221> NAME/KEY: MOD_RES
<222> LOCATION: (127)
<223> OTHER INFORMATION: Hyp
<220> FEATURE:
<221> NAME/KEY: MOD_RES
<222> LOCATION: (129)
<223> OTHER INFORMATION: Hyp
<220> FEATURE:
<221> NAME/KEY: MOD_RES
<222> LOCATION: (131)
<223> OTHER INFORMATION: Hyp
<220> FEATURE:
<221> NAME/KEY: MOD_RES
<222> LOCATION: (133)
<223> OTHER INFORMATION: Hyp
<220> FEATURE:
<221> NAME/KEY: MOD_RES
<222> LOCATION: (135)
<223> OTHER INFORMATION: Hyp
<220> FEATURE:
<221> NAME/KEY: MOD_RES
<222> LOCATION: (137)
<223> OTHER INFORMATION: Hyp
<220> FEATURE:
<221> NAME/KEY: MOD_RES
<222> LOCATION: (139)
<223> OTHER INFORMATION: Hyp
<220> FEATURE:
<221> NAME/KEY: MOD_RES
<222> LOCATION: (141)
<223> OTHER INFORMATION: Hyp
<220> FEATURE:
<221> NAME/KEY: MOD_RES
<222> LOCATION: (143)
<223> OTHER INFORMATION: Hyp
<220> FEATURE:
<221> NAME/KEY: MOD_RES
<222> LOCATION: (145)
<223> OTHER INFORMATION: Hyp
```

```
<220> FEATURE:
<221> NAME/KEY: MOD_RES
<222> LOCATION: (147)
<223> OTHER INFORMATION: Hyp
<220> FEATURE:
<221> NAME/KEY: MOD_RES
<222> LOCATION: (149)
<223> OTHER INFORMATION: Hyp
<220> FEATURE:
<221> NAME/KEY: MOD_RES
<222> LOCATION: (151)
<223> OTHER INFORMATION: Hyp
<220> FEATURE:
<221> NAME/KEY: MOD_RES
<222> LOCATION: (153)
<223> OTHER INFORMATION: Hyp
<220> FEATURE:
<221> NAME/KEY: MOD_RES
<222> LOCATION: (155)
<223> OTHER INFORMATION: Hyp
<220> FEATURE:
<221> NAME/KEY: MOD_RES
<222> LOCATION: (157)
<223> OTHER INFORMATION: Hyp
<220> FEATURE:
<221> NAME/KEY: MOD_RES
<222> LOCATION: (159)
<223> OTHER INFORMATION: Hyp
<220> FEATURE:
<221> NAME/KEY: MOD_RES
<222> LOCATION: (161)
<223> OTHER INFORMATION: Hyp
<220> FEATURE:
<221> NAME/KEY: MOD_RES
<222> LOCATION: (163)
<223> OTHER INFORMATION: Hyp
<220> FEATURE:
<221> NAME/KEY: MOD_RES
<222> LOCATION: (165)
<223> OTHER INFORMATION: Hyp
<220> FEATURE:
<221> NAME/KEY: MOD_RES
<222> LOCATION: (167)
<223> OTHER INFORMATION: Hyp
<220> FEATURE:
<221> NAME/KEY: MOD_RES
<222> LOCATION: (169)
<223> OTHER INFORMATION: Hyp
<220> FEATURE:
<221> NAME/KEY: MOD_RES
<222> LOCATION: (171)
<223> OTHER INFORMATION: Hyp
<220> FEATURE:
<221> NAME/KEY: MOD_RES
<222> LOCATION: (173)
<223> OTHER INFORMATION: Hyp
<220> FEATURE:
<221> NAME/KEY: MOD_RES
<222> LOCATION: (175)
<223> OTHER INFORMATION: Hyp
<220> FEATURE:
<221> NAME/KEY: MOD_RES
<222> LOCATION: (177)
<223> OTHER INFORMATION: Hyp
<220> FEATURE:
<221> NAME/KEY: MOD_RES
<222> LOCATION: (179)
<223> OTHER INFORMATION: Hyp
<220> FEATURE:
<221> NAME/KEY: MOD_RES
<222> LOCATION: (181)
<223> OTHER INFORMATION: Hyp
<220> FEATURE:
<221> NAME/KEY: MOD_RES
<222> LOCATION: (183)
<223> OTHER INFORMATION: Hyp
<220> FEATURE:
<221> NAME/KEY: MOD_RES
<222> LOCATION: (185)
<223> OTHER INFORMATION: Hyp
```

```
<220> FEATURE:
<221> NAME/KEY: MOD_RES
<222> LOCATION: (187)
<223> OTHER INFORMATION: Hyp
<220> FEATURE:
<221> NAME/KEY: MOD_RES
<222> LOCATION: (189)
<223> OTHER INFORMATION: Hyp
<220> FEATURE:
<221> NAME/KEY: MOD_RES
<222> LOCATION: (191)
<223> OTHER INFORMATION: Hyp
<220> FEATURE:
<221> NAME/KEY: MOD_RES
<222> LOCATION: (193)
<223> OTHER INFORMATION: Hyp
<220> FEATURE:
<221> NAME/KEY: MOD_RES
<222> LOCATION: (195)
<223> OTHER INFORMATION: Hyp
<220> FEATURE:
<221> NAME/KEY: MOD_RES
<222> LOCATION: (197)
<223> OTHER INFORMATION: Hyp
<220> FEATURE:
<221> NAME/KEY: MOD_RES
<222> LOCATION: (199)
<223> OTHER INFORMATION: Hyp
<220> FEATURE:
<221> NAME/KEY: MOD_RES
<222> LOCATION: (201)
<223> OTHER INFORMATION: Hyp
<220> FEATURE:
<221> NAME/KEY: MOD_RES
<222> LOCATION: (203)
<223> OTHER INFORMATION: Hyp
<220> FEATURE:
<221> NAME/KEY: MOD_RES
<222> LOCATION: (205)
<223> OTHER INFORMATION: Hyp
<220> FEATURE:
<221> NAME/KEY: MOD_RES
<222> LOCATION: (207)
<223> OTHER INFORMATION: Hyp
<220> FEATURE:
<221> NAME/KEY: MOD_RES
<222> LOCATION: (209)
<223> OTHER INFORMATION: Hyp
<220> FEATURE:
<221> NAME/KEY: MOD_RES
<222> LOCATION: (211)
<223> OTHER INFORMATION: Hyp
<220> FEATURE:
<221> NAME/KEY: MOD_RES
<222> LOCATION: (213)
<223> OTHER INFORMATION: Hyp
<220> FEATURE:
<221> NAME/KEY: MOD_RES
<222> LOCATION: (215)
<223> OTHER INFORMATION: Hyp
<220> FEATURE:
<221> NAME/KEY: MOD_RES
<222> LOCATION: (217)
<223> OTHER INFORMATION: Hyp
<220> FEATURE:
<221> NAME/KEY: MOD_RES
<222> LOCATION: (219)
<223> OTHER INFORMATION: Hyp
<220> FEATURE:
<221> NAME/KEY: MOD_RES
<222> LOCATION: (271)..(274)
<223> OTHER INFORMATION: Hyp
<220> FEATURE:
<221> NAME/KEY: MOD_RES
<222> LOCATION: (276)
<223> OTHER INFORMATION: Hyp
<220> FEATURE:
<221> NAME/KEY: MOD_RES
<222> LOCATION: (281)..(284)
<223> OTHER INFORMATION: Hyp
```

```
<220> FEATURE:
<221> NAME/KEY: MOD_RES
<222> LOCATION: (286)
<223> OTHER INFORMATION: Hyp
<220> FEATURE:
<221> NAME/KEY: MOD_RES
<222> LOCATION: (291)..(294)
<223> OTHER INFORMATION: Hyp

<400> SEQUENCE: 79

Ser Xaa Xaa Xaa Xaa Thr Xaa Val Tyr Lys Ser Xaa Xaa Xaa Xaa Thr
 1               5                  10                  15

Xaa Val Tyr Lys Ser Xaa Xaa Xaa Xaa Val Gly Val Pro Gly Val Gly
             20                  25                  30

Val Pro Gly Val Gly Val Pro Gly Val Gly Val Pro Gly Val Gly Val
         35                  40                  45

Pro Gly Val Gly Val Pro Gly Val Gly Val Pro Gly Val Gly Val Pro
     50                  55                  60

Gly Val Gly Val Pro Gly Val Gly Val Pro Gly Ser Xaa Ser Xaa Ser
 65                  70                  75                  80

Xaa Ser Xaa Ser Xaa Ser Xaa Ser Xaa Ser Xaa Ser Xaa Ser Xaa Ser
             85                  90                  95

Xaa Ser Xaa Ser Xaa Ser Xaa Ser Xaa Ser Xaa Ser Xaa Ser Xaa Ser
            100                 105                 110

Xaa Ser Xaa Ser Xaa Ser Xaa Ser Xaa Ser Xaa Ser Xaa Ser Xaa Ser
            115                 120                 125

Xaa Ser Xaa Ser Xaa Ser Xaa Ser Xaa Ser Xaa Ser Xaa Ser Xaa Ser
        130                 135                 140

Xaa Ser Xaa Ser Xaa Ser Xaa Ser Xaa Ser Xaa Ser Xaa Ser Xaa Ser
145                 150                 155                 160

Xaa Ser Xaa Ser Xaa Ser Xaa Ser Xaa Ser Xaa Ser Xaa Ser Xaa Ser
            165                 170                 175

Xaa Ser Xaa Ser Xaa Ser Xaa Ser Xaa Ser Xaa Ser Xaa Ser Xaa Ser
            180                 185                 190

Xaa Ser Xaa Ser Xaa Ser Xaa Ser Xaa Ser Xaa Ser Xaa Ser Xaa Ser
            195                 200                 205

Xaa Ser Xaa Ser Xaa Ser Xaa Ser Xaa Ser Xaa Val Gly Val Pro Gly
        210                 215                 220

Val Gly Val Pro Gly Val Gly Val Pro Gly Val Gly Val Pro Gly Val
225                 230                 235                 240

Gly Val Pro Gly Val Gly Val Pro Gly Val Gly Val Pro Gly Val Gly
            245                 250                 255

Val Pro Gly Val Gly Val Pro Gly Val Gly Val Pro Gly Ser Xaa Xaa
            260                 265                 270

Xaa Xaa Thr Xaa Val Tyr Lys Ser Xaa Xaa Xaa Xaa Thr Xaa Val Tyr
        275                 280                 285

Lys Ser Xaa Xaa Xaa Xaa
            290

<210> SEQ ID NO 80
<211> LENGTH: 84
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Hyp
```

```
<220> FEATURE:
<221> NAME/KEY: MOD_RES
<222> LOCATION: (16)
<223> OTHER INFORMATION: Hyp
<220> FEATURE:
<221> NAME/KEY: MOD_RES
<222> LOCATION: (18)
<223> OTHER INFORMATION: Hyp
<220> FEATURE:
<221> NAME/KEY: MOD_RES
<222> LOCATION: (20)
<223> OTHER INFORMATION: Hyp
<220> FEATURE:
<221> NAME/KEY: MOD_RES
<222> LOCATION: (22)
<223> OTHER INFORMATION: Hyp
<220> FEATURE:
<221> NAME/KEY: MOD_RES
<222> LOCATION: (24)
<223> OTHER INFORMATION: Hyp
<220> FEATURE:
<221> NAME/KEY: MOD_RES
<222> LOCATION: (26)
<223> OTHER INFORMATION: Hyp
<220> FEATURE:
<221> NAME/KEY: MOD_RES
<222> LOCATION: (28)
<223> OTHER INFORMATION: Hyp
<220> FEATURE:
<221> NAME/KEY: MOD_RES
<222> LOCATION: (30)
<223> OTHER INFORMATION: Hyp
<220> FEATURE:
<221> NAME/KEY: MOD_RES
<222> LOCATION: (32)
<223> OTHER INFORMATION: Hyp
<220> FEATURE:
<221> NAME/KEY: MOD_RES
<222> LOCATION: (34)
<223> OTHER INFORMATION: Hyp
<220> FEATURE:
<221> NAME/KEY: MOD_RES
<222> LOCATION: (36)
<223> OTHER INFORMATION: Hyp
<220> FEATURE:
<221> NAME/KEY: MOD_RES
<222> LOCATION: (38)
<223> OTHER INFORMATION: Hyp
<220> FEATURE:
<221> NAME/KEY: MOD_RES
<222> LOCATION: (40)
<223> OTHER INFORMATION: Hyp
<220> FEATURE:
<221> NAME/KEY: MOD_RES
<222> LOCATION: (42)
<223> OTHER INFORMATION: Hyp
<220> FEATURE:
<221> NAME/KEY: MOD_RES
<222> LOCATION: (44)
<223> OTHER INFORMATION: Hyp
<220> FEATURE:
<221> NAME/KEY: MOD_RES
<222> LOCATION: (46)
<223> OTHER INFORMATION: Hyp
<220> FEATURE:
<221> NAME/KEY: MOD_RES
<222> LOCATION: (48)
<223> OTHER INFORMATION: Hyp
<220> FEATURE:
<221> NAME/KEY: MOD_RES
<222> LOCATION: (50)
<223> OTHER INFORMATION: Hyp
<220> FEATURE:
<221> NAME/KEY: MOD_RES
<222> LOCATION: (52)
<223> OTHER INFORMATION: Hyp
<220> FEATURE:
<221> NAME/KEY: MOD_RES
<222> LOCATION: (54)
<223> OTHER INFORMATION: Hyp
```

```
<220> FEATURE:
<221> NAME/KEY: MOD_RES
<222> LOCATION: (56)
<223> OTHER INFORMATION: Hyp
<220> FEATURE:
<221> NAME/KEY: MOD_RES
<222> LOCATION: (58)
<223> OTHER INFORMATION: Hyp
<220> FEATURE:
<221> NAME/KEY: MOD_RES
<222> LOCATION: (60)
<223> OTHER INFORMATION: Hyp
<220> FEATURE:
<221> NAME/KEY: MOD_RES
<222> LOCATION: (62)
<223> OTHER INFORMATION: Hyp
<220> FEATURE:
<221> NAME/KEY: MOD_RES
<222> LOCATION: (64)
<223> OTHER INFORMATION: Hyp
<220> FEATURE:
<221> NAME/KEY: MOD_RES
<222> LOCATION: (66)
<223> OTHER INFORMATION: Hyp
<220> FEATURE:
<221> NAME/KEY: MOD_RES
<222> LOCATION: (68)
<223> OTHER INFORMATION: Hyp
<220> FEATURE:
<221> NAME/KEY: MOD_RES
<222> LOCATION: (70)
<223> OTHER INFORMATION: Hyp
<220> FEATURE:
<221> NAME/KEY: MOD_RES
<222> LOCATION: (72)
<223> OTHER INFORMATION: Hyp

<400> SEQUENCE: 80

Val Pro Gly Val Pro Gly Val Pro Gly Val Pro Gly Ala Xaa Ala Xaa
 1               5                  10                  15

Ala Xaa Ala Xaa Ala Xaa Ala Xaa Ala Xaa Ala Xaa Ala Xaa Ala Xaa
            20                  25                  30

Ala Xaa Ala Xaa Ala Xaa Ala Xaa Ala Xaa Ala Xaa Ala Xaa Ala Xaa
        35                  40                  45

Ala Xaa Ala Xaa Ala Xaa Ala Xaa Ala Xaa Ala Xaa Ala Xaa Ala Xaa
    50                  55                  60

Ala Xaa Ala Xaa Ala Xaa Ala Xaa Val Pro Gly Val Pro Gly Val Pro
65                  70                  75                  80

Gly Val Pro Gly

<210> SEQ ID NO 81
<211> LENGTH: 186
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Hyp
<220> FEATURE:
<221> NAME/KEY: MOD_RES
<222> LOCATION: (8)
<223> OTHER INFORMATION: Hyp
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Hyp
```

```
<220> FEATURE:
<221> NAME/KEY: MOD_RES
<222> LOCATION: (14)..(15)
<223> OTHER INFORMATION: Hyp
<220> FEATURE:
<221> NAME/KEY: MOD_RES
<222> LOCATION: (21)..(23)
<223> OTHER INFORMATION: Hyp
<220> FEATURE:
<221> NAME/KEY: MOD_RES
<222> LOCATION: (27)
<223> OTHER INFORMATION: Hyp
<220> FEATURE:
<221> NAME/KEY: MOD_RES
<222> LOCATION: (29)
<223> OTHER INFORMATION: Hyp
<220> FEATURE:
<221> NAME/KEY: MOD_RES
<222> LOCATION: (31)
<223> OTHER INFORMATION: Hyp
<220> FEATURE:
<221> NAME/KEY: MOD_RES
<222> LOCATION: (33)..(34)
<223> OTHER INFORMATION: Hyp
<220> FEATURE:
<221> NAME/KEY: MOD_RES
<222> LOCATION: (40)
<223> OTHER INFORMATION: Hyp
<220> FEATURE:
<221> NAME/KEY: MOD_RES
<222> LOCATION: (45)..(47)
<223> OTHER INFORMATION: Hyp
<220> FEATURE:
<221> NAME/KEY: MOD_RES
<222> LOCATION: (51)
<223> OTHER INFORMATION: Hyp
<220> FEATURE:
<221> NAME/KEY: MOD_RES
<222> LOCATION: (53)
<223> OTHER INFORMATION: Hyp
<220> FEATURE:
<221> NAME/KEY: MOD_RES
<222> LOCATION: (55)
<223> OTHER INFORMATION: Hyp
<220> FEATURE:
<221> NAME/KEY: MOD_RES
<222> LOCATION: (57)..(58)
<223> OTHER INFORMATION: Hyp
<220> FEATURE:
<221> NAME/KEY: MOD_RES
<222> LOCATION: (64)..(66)
<223> OTHER INFORMATION: Hyp
<220> FEATURE:
<221> NAME/KEY: MOD_RES
<222> LOCATION: (70)
<223> OTHER INFORMATION: Hyp
<220> FEATURE:
<221> NAME/KEY: MOD_RES
<222> LOCATION: (72)
<223> OTHER INFORMATION: Hyp
<220> FEATURE:
<221> NAME/KEY: MOD_RES
<222> LOCATION: (74)
<223> OTHER INFORMATION: Hyp
<220> FEATURE:
<221> NAME/KEY: MOD_RES
<222> LOCATION: (76)..(77)
<223> OTHER INFORMATION: Hyp
<220> FEATURE:
<221> NAME/KEY: MOD_RES
<222> LOCATION: (83)
<223> OTHER INFORMATION: Hyp
<220> FEATURE:
<221> NAME/KEY: MOD_RES
<222> LOCATION: (88)..(90)
<223> OTHER INFORMATION: Hyp
<220> FEATURE:
<221> NAME/KEY: MOD_RES
<222> LOCATION: (94)
<223> OTHER INFORMATION: Hyp
```

-continued

```
<220> FEATURE:
<221> NAME/KEY: MOD_RES
<222> LOCATION: (96)
<223> OTHER INFORMATION: Hyp
<220> FEATURE:
<221> NAME/KEY: MOD_RES
<222> LOCATION: (98)
<223> OTHER INFORMATION: Hyp
<220> FEATURE:
<221> NAME/KEY: MOD_RES
<222> LOCATION: (100)..(101)
<223> OTHER INFORMATION: Hyp
<220> FEATURE:
<221> NAME/KEY: MOD_RES
<222> LOCATION: (107)..(109)
<223> OTHER INFORMATION: Hyp
<220> FEATURE:
<221> NAME/KEY: MOD_RES
<222> LOCATION: (113)
<223> OTHER INFORMATION: Hyp
<220> FEATURE:
<221> NAME/KEY: MOD_RES
<222> LOCATION: (115)
<223> OTHER INFORMATION: Hyp
<220> FEATURE:
<221> NAME/KEY: MOD_RES
<222> LOCATION: (117)
<223> OTHER INFORMATION: Hyp
<220> FEATURE:
<221> NAME/KEY: MOD_RES
<222> LOCATION: (119)..(120)
<223> OTHER INFORMATION: Hyp
<220> FEATURE:
<221> NAME/KEY: MOD_RES
<222> LOCATION: (126)
<223> OTHER INFORMATION: Hyp
<220> FEATURE:
<221> NAME/KEY: MOD_RES
<222> LOCATION: (131)..(133)
<223> OTHER INFORMATION: Hyp
<220> FEATURE:
<221> NAME/KEY: MOD_RES
<222> LOCATION: (137)
<223> OTHER INFORMATION: Hyp
<220> FEATURE:
<221> NAME/KEY: MOD_RES
<222> LOCATION: (139)
<223> OTHER INFORMATION: Hyp
<220> FEATURE:
<221> NAME/KEY: MOD_RES
<222> LOCATION: (141)
<223> OTHER INFORMATION: Hyp
<220> FEATURE:
<221> NAME/KEY: MOD_RES
<222> LOCATION: (143)..(144)
<223> OTHER INFORMATION: Hyp
<220> FEATURE:
<221> NAME/KEY: MOD_RES
<222> LOCATION: (150)
<223> OTHER INFORMATION: Hyp
<220> FEATURE:
<221> NAME/KEY: MOD_RES
<222> LOCATION: (156)
<223> OTHER INFORMATION: Hyp
<220> FEATURE:
<221> NAME/KEY: MOD_RES
<222> LOCATION: (160)
<223> OTHER INFORMATION: Hyp
<220> FEATURE:
<221> NAME/KEY: MOD_RES
<222> LOCATION: (162)..(163)
<223> OTHER INFORMATION: Hyp
<220> FEATURE:
<221> NAME/KEY: MOD_RES
<222> LOCATION: (169)
<223> OTHER INFORMATION: Hyp
<220> FEATURE:
<221> NAME/KEY: MOD_RES
<222> LOCATION: (175)
<223> OTHER INFORMATION: Hyp
```

```
<220> FEATURE:
<221> NAME/KEY: MOD_RES
<222> LOCATION: (179)
<223> OTHER INFORMATION: Hyp
<220> FEATURE:
<221> NAME/KEY: MOD_RES
<222> LOCATION: (181)..(182)
<223> OTHER INFORMATION: Hyp

<400> SEQUENCE: 81

Ser Xaa Xaa Xaa Thr Leu Ser Xaa Ser Xaa Thr Xaa Thr Xaa Xaa Leu
 1               5                  10                  15

Gly Pro His Ser Xaa Xaa Xaa Thr Leu Ser Xaa Ser Xaa Thr Xaa Thr
             20                  25                  30

Xaa Xaa Leu Gly Pro His Thr Xaa Val Tyr Lys Ser Xaa Xaa Xaa Thr
         35                  40                  45

Leu Ser Xaa Ser Xaa Thr Xaa Thr Xaa Xaa Leu Gly Pro His Ser Xaa
     50                  55                  60

Xaa Xaa Thr Leu Ser Xaa Ser Xaa Thr Xaa Thr Xaa Xaa Leu Gly Pro
 65                  70                  75                  80

His Thr Xaa Val Tyr Lys Ser Xaa Xaa Xaa Thr Leu Ser Xaa Ser Xaa
                 85                  90                  95

Thr Xaa Thr Xaa Xaa Leu Gly Pro His Ser Xaa Xaa Xaa Thr Leu Ser
            100                 105                 110

Xaa Ser Xaa Thr Xaa Thr Xaa Xaa Leu Gly Pro His Thr Xaa Val Tyr
        115                 120                 125

Lys Ser Xaa Xaa Xaa Thr Leu Ser Xaa Ser Xaa Thr Xaa Thr Xaa Xaa
    130                 135                 140

Leu Gly Pro His Ser Xaa Leu Pro Thr Leu Ser Xaa Leu Pro Thr Xaa
145                 150                 155                 160

Thr Xaa Xaa Leu Leu Pro His Ser Xaa Leu Pro Thr Leu Ser Xaa Leu
            165                 170                 175

Pro Thr Xaa Thr Xaa Xaa Leu Leu Pro His
            180                 185

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Hyp

<400> SEQUENCE: 82

Pro Xaa Val Tyr Lys
 1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Val Gln Gln Glu Leu
 1               5
```

```
<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Gly Gln Gln Ile Val
  1               5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Cys Cys Ser
  1

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Pro Gly Val Gly
  1               5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Pro Pro Pro Pro Thr Pro Val Tyr Lys
  1               5                  10

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Pro Pro Pro Pro Val Lys Pro Tyr His Pro Thr Pro Val Tyr Lys
  1               5                  10                  15

<210> SEQ ID NO 89
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89
```

```
Ser Pro Pro Pro Pro Thr Pro Val Tyr Lys Ser Pro Pro Pro Thr
 1               5                   10                  15

Pro Val Tyr Lys Ser Pro Pro Pro Thr Pro Val Tyr Lys Ser Pro
            20                  25                  30

Pro Pro Thr Pro Val Tyr Lys Ser Pro Pro Pro Thr Pro Val
        35                  40                  45

Tyr Lys Ser Pro Pro Pro Thr Pro Val Tyr Lys
         50                  55                  60

<210> SEQ ID NO 90
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Pro Pro Pro Pro Thr Pro Val Phe Leu Ser Pro Pro Pro Thr
 1               5                   10                  15

Pro Val Phe Leu Ser Pro Pro Pro Thr Pro Val Phe Leu Ser Pro
            20                  25                  30

Pro Pro Thr Pro Val Phe Leu Ser Pro Pro Pro Thr Pro Val
        35                  40                  45

Phe Leu Ser Pro Pro Pro Thr Pro Val Phe Leu
         50                  55                  60

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Pro Pro Pro Pro Thr Pro Val Tyr Leu
 1               5                   10

<210> SEQ ID NO 92
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (10)..(13)
<223> OTHER INFORMATION: Hyp
<220> FEATURE:
<221> NAME/KEY: MOD_RES
<222> LOCATION: (18)..(21)
<223> OTHER INFORMATION: Hyp
<220> FEATURE:
<221> NAME/KEY: MOD_RES
<222> LOCATION: (26)..(29)
<223> OTHER INFORMATION: Hyp
<220> FEATURE:
<221> NAME/KEY: MOD_RES
<222> LOCATION: (34)..(37)
<223> OTHER INFORMATION: Hyp
<220> FEATURE:
<221> NAME/KEY: MOD_RES
<222> LOCATION: (42)..(45)
```

<223> OTHER INFORMATION: Hyp

<400> SEQUENCE: 92

Ser Xaa Xaa Xaa Xaa Val Tyr Lys Ser Xaa Xaa Xaa Xaa Val Tyr Lys
1               5                   10                  15

Ser Xaa Xaa Xaa Xaa Val Tyr Lys Ser Xaa Xaa Xaa Xaa Val Tyr Lys
            20                  25                  30

Ser Xaa Xaa Xaa Xaa Val Tyr Lys Ser Xaa Xaa Xaa Xaa Val Tyr Lys
            35                  40                  45

<210> SEQ ID NO 93
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (10)..(13)
<223> OTHER INFORMATION: Hyp
<220> FEATURE:
<221> NAME/KEY: MOD_RES
<222> LOCATION: (18)..(21)
<223> OTHER INFORMATION: Hyp
<220> FEATURE:
<221> NAME/KEY: MOD_RES
<222> LOCATION: (26)..(29)
<223> OTHER INFORMATION: Hyp
<220> FEATURE:
<221> NAME/KEY: MOD_RES
<222> LOCATION: (34)..(37)
<223> OTHER INFORMATION: Hyp
<220> FEATURE:
<221> NAME/KEY: MOD_RES
<222> LOCATION: (42)..(45)
<223> OTHER INFORMATION: Hyp

<400> SEQUENCE: 93

Ser Xaa Xaa Xaa Xaa Val Phe Leu Ser Xaa Xaa Xaa Xaa Val Phe Leu
1               5                   10                  15

Ser Xaa Xaa Xaa Xaa Val Phe Leu Ser Xaa Xaa Xaa Xaa Val Phe Leu
            20                  25                  30

Ser Xaa Xaa Xaa Xaa Val Phe Leu Ser Xaa Xaa Xaa Xaa Val Phe Leu
            35                  40                  45

<210> SEQ ID NO 94
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Hyp
<220> FEATURE:
<221> NAME/KEY: MOD_RES
<222> LOCATION: (10)..(13)
<223> OTHER INFORMATION: Hyp
<220> FEATURE:
<221> NAME/KEY: MOD_RES
<222> LOCATION: (18)..(21)
<223> OTHER INFORMATION: Hyp
<220> FEATURE:
<221> NAME/KEY: MOD_RES
<222> LOCATION: (26)..(29)

```
<223> OTHER INFORMATION: Hyp
<220> FEATURE:
<221> NAME/KEY: MOD_RES
<222> LOCATION: (34)..(37)
<223> OTHER INFORMATION: Hyp
<220> FEATURE:
<221> NAME/KEY: MOD_RES
<222> LOCATION: (42)..(45)
<223> OTHER INFORMATION: Hyp

<400> SEQUENCE: 94

Ser Xaa Xaa Xaa Xaa Val Tyr Leu Ser Xaa Xaa Xaa Xaa Val Tyr Leu
 1               5                  10                  15

Ser Xaa Xaa Xaa Xaa Val Tyr Leu Ser Xaa Xaa Xaa Xaa Val Tyr Leu
                20                  25                  30

Ser Xaa Xaa Xaa Xaa Val Tyr Leu Ser Xaa Xaa Xaa Xaa Val Tyr Leu
            35                  40                  45

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ala Pro Ala Pro Ala Pro Ala
 1               5

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ccgggctcca gcacctgccc cagcc                                         25

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
atggggctgg ggcaggtgct ggagc                                         25

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Pro Ala Pro Ala Pro Ala
 1               5

<210> SEQ ID NO 99
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 99

Ala Pro Ala Pro Ala Pro
 1               5

<210> SEQ ID NO 100
<211> LENGTH: 102
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Pro Ala Pro Ala Pro Ala Pro Ala Pro Ala Pro Ala Pro Ala Pro
 1               5                  10                  15

Ala Pro Ala Pro Ala Pro Ala Pro Ala Pro Ala Pro Ala Pro
             20                  25                  30

Ala Pro Ala Pro Ala Pro Ala Pro Ala Pro Ala Pro Ala Pro
         35                  40                  45

Ala Pro Ala Pro Ala Pro Ala Pro Ala Pro Ala Pro Ala Pro
     50                  55                  60

Ala Pro Ala Pro Ala Pro Ala Pro Ala Pro Ala Pro Ala Pro
65                  70                  75                  80

Ala Pro Ala Pro Ala Pro Ala Pro Ala Pro Ala Pro Ala Pro
                85                  90                  95

Ala Pro Ala Pro Ala Pro
            100

<210> SEQ ID NO 101
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Pro Ala Pro Ala Pro Ala Pro Ser Pro Pro Pro Pro Tyr Tyr Tyr
 1               5                  10                  15

Lys Ser Pro Pro Pro Pro Ser Pro
             20

<210> SEQ ID NO 102
<211> LENGTH: 1041
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gctccagcac ctgccccagc ccatcacca ccaccacctt actactacaa gtctcctcct      60 ccccatcac caccatcacc accacccct tactactaca agtctcctcc tcccccatca     120
ccaccatcac caccaccacc ttactactac aagtctcctc ctcccccatc accaccatca     180
ccaccaccac ttactactac aagtctcct cctccccca caccaccatc accaccacca     240
ccttactact acaagtctcc tcctccccca tcaccaccat caccaccacc acttactac     300 tacaagtctc ctcctccccc atcaccacca tcaccaccac cacttactac ctacaagtct     360
```

```
cctcctcccc catcaccacc atcaccacca ccaccttact actacaagtc tcctcctccc       420
ccatcaccac catcaccacc accaccttac tactacaagt ctcctcctcc cccatcacca       480
ccatcaccac caccacctta ctactacaag tctcctcctc ccccatcacc accatcacca       540
ccaccacctt actactacaa gtctcctcct cccccatcac caccatcacc accaccacct       600
tactactaca gtctcctccc tcccccatca ccaccatcac caccaccacc ttactactac       660
aagtctcctc ctcccccatc accaccatca ccaccaccac cttactacta caagtctcct       720
cctcccccat caccaccatc accaccacca ccttactact acaagtctcc tcctccccca       780
tcaccaccat caccaccacc accttactac tacaagtctc ctcctccccc atcaccacca       840
tcaccaccac caccttacta ctacaagtct cctcctcccc catcaccacc atcaccacca       900
ccaccttact actacaagtc tcctcctccc ccatcaccac catcaccacc accaccttac       960
tactacaagt ctcctcctcc cccatcacca ccatcaccac caccacctta ctactacaag      1020
tctcctcctc ccccatcacc a                                                1041

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Pro Ala Pro Ala Pro Ala Pro Ser Pro Pro Pro Tyr Tyr Tyr
  1               5                  10                  15

Lys Ser Pro Pro Pro Pro Ser Pro
             20

<210> SEQ ID NO 104
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
gctccagcac ctgccccagc cccatcacca ccaccacctt actactacaa gtctcctcct        60
cccccatcac caccatcacc accaccacct tactactaca gtctcctccc tcccccatca       120
ccaccatcac caccaccacc ttactactac aagtctcctc ctcccccatc accaccatca       180
ccaccaccac cttactacta caagtctcct cctcccccat caccaccatc accaccacca       240
ccttactact acaagtctcc tcctccccca tcaccaccat caccaccacc accttactac       300
tacaagtctc ctcctccccc atcaccacca tcaccaccac caccttacta ctacaagtct       360
cctcctcccc catcaccacc atcaccacca ccaccttact actacaagtc tcctcctccc       420
ccatcacca                                                              429

<210> SEQ ID NO 105
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105
```

Ala Pro Ala Pro Ala Pro Ala Pro Ser Pro Pro Pro Tyr Tyr Tyr
1               5                   10                  15

Lys Ser Pro Pro Pro Pro Ser Pro
            20

<210> SEQ ID NO 106
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
gctccagcac ctgccccagc cccatcacca ccaccacctt actactacaa gtctcctcct      60
cccccatcac caccatcacc accaccacct tactactaca agtctcctcc tcccccatca     120
ccaccatcac caccaccacc ttactactac aagtctcctc ctcccccatc accaccatca     180
ccaccaccac cttactacta caagtctcct cctcccccat cacca                     225

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Pro Pro Pro Pro Ser Pro Ser Pro Pro Pro Pro Tyr Tyr Tyr Lys
1               5                   10                  15

<210> SEQ ID NO 108
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Pro Ser Gly Val Gly Val Pro Gly Val Gly Ala Pro Ala Pro Ala Pro
1               5                   10                  15

Ala Gly Val Gly Val Pro Gly Val Gly
            20                  25

<210> SEQ ID NO 109
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ccatcaggag taggtgttcc aggagttggc gttccaggag ttggcgctcc agcacctgcc      60
ccagccggtg ttggagtacc tggtgttggt gtacctggtg ttggt                     105

<210> SEQ ID NO 110
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 110
atggaccaac accaggtaca ccaacaccag gtactccaac accggctggg gcaggtgctg        60
gagcgccaac tcctggaacg ccaactcctg gaacacctac tcctg                       105

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(30)

<400> SEQUENCE: 111 gct gcc gga tcc tca acc cgg gcc tca cca                                  30
Ala Ala Gly Ser Ser Thr Arg Ala Ser Pro
  1               5                  10

<210> SEQ ID NO 112
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aggtggtggt ggtgagcccc gggttgagga tccggcagc                               39

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Ala Gly Ser Ser Thr Arg Ala Ser Pro
  1               5                  10

<210> SEQ ID NO 114
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(48)

<400> SEQUENCE: 114 cca cca cct agt ccg tca ccc cct ccc cca ttt ttc ttt aag agc cca          48
Pro Pro Pro Ser Pro Ser Pro Pro Pro Phe Phe Phe Lys Ser Pro
  1               5                  10                  15

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 115
aggtggtggt gggctcttaa agaaaaatgg gggaggggggt gacggact                    48

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Pro Pro Pro Ser Pro Ser Pro Pro Pro Phe Phe Phe Lys Ser Pro
 1               5                  10                  15

<210> SEQ ID NO 117
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(18)

<400> SEQUENCE: 117 cca cca cct tcc atg gca taatagagct cgaattcctg gcccacc                   45
Pro Pro Pro Ser Met Ala
 1               5

<210> SEQ ID NO 118
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ggtgggccag gaattcgagc tctattatgc catgga                                 36

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Pro Pro Pro Ser Met Ala
 1               5

<210> SEQ ID NO 120
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(54)
```

<400> SEQUENCE: 120

```
ggg acc cgg gga aga cga cca tca cca cca cct tac tac tac aag      48
Gly Thr Arg Gly Arg Arg Pro Ser Pro Pro Pro Tyr Tyr Tyr Lys
 1               5                  10                  15 tct cct                                                           54
Ser Pro
```

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Gly Thr Arg Gly Arg Arg Pro Ser Pro Pro Pro Tyr Tyr Tyr Lys
 1               5                  10                  15

Ser Pro
```

<210> SEQ ID NO 122
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122

```
attgagctcc tatcaccggg acgccatggt tgatggtgat gggggaggag gagacttgta      60
gtagtaaggt gg                                                         72
```

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Pro Pro Tyr Tyr Tyr Lys Ser Pro Pro Pro Ser Pro Ser Thr Met
 1               5                  10                  15

Ala Ser Arg Glu Leu Asn
            20
```

<210> SEQ ID NO 124
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(54)

<400> SEQUENCE: 124

```
ggg acc cgg gga aga cga cca tca cca cca cca cct tac tac tac cta      48
Gly Thr Arg Gly Arg Arg Pro Ser Pro Pro Pro Pro Tyr Tyr Tyr Leu
 1               5                  10                  15 tct cct                                                           54
Ser Pro
```

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Thr Arg Gly Arg Arg Pro Ser Pro Pro Pro Pro Tyr Tyr Tyr Leu
 1               5                  10                  15

Ser Pro

<210> SEQ ID NO 126
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
attgagctcc tatcaccggg acgccatggt tgatggtgat gggggaggag gagataggta      60
gtagtaaggt gg                                                         72

<210> SEQ ID NO 127
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Pro Tyr Tyr Tyr Leu Ser Pro Pro Pro Ser Pro Ser Thr Met
 1               5                  10                  15

Ala Ser Arg Glu Leu Asn
            20

<210> SEQ ID NO 128
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(54)

<400> SEQUENCE: 128 ggg acc cgg gga aga cga cca tca cca cca cca cct ttt ttc ttt cta      48
Gly Thr Arg Gly Arg Arg Pro Ser Pro Pro Pro Pro Phe Phe Phe Leu
 1               5                  10                  15 tct cct                                                              54
Ser Pro

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 129

Gly Thr Arg Gly Arg Arg Pro Ser Pro Pro Pro Pro Phe Phe Phe Leu
 1               5                  10                  15

Ser Pro

<210> SEQ ID NO 130
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
attgagctcc tatcaccggg acgccatggt tgatggtgat ggggaggag gagatagaaa      60 gaaaaaaggt gg                                                        72

<210> SEQ ID NO 131
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Pro Pro Phe Phe Phe Leu Ser Pro Pro Pro Ser Pro Ser Thr Met
 1               5                  10                  15

Ala Ser Arg Glu Leu Asn
            20

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gtaaaacgac ggccagtg                                                  18

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cggcaatggg aaaaatggct tct                                            23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gaagatggtg cgctcctgga cgt                                            23
```

```
<210> SEQ ID NO 135
<211> LENGTH: 162
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(162)

<400> SEQUENCE: 135 gga tcc gca atg gga aaa atg gct tct cta ttt gcc aca ttt tta gtg      48
Gly Ser Ala Met Gly Lys Met Ala Ser Leu Phe Ala Thr Phe Leu Val
 1               5                  10                  15 gtt tta gtg tca ctt agc tta gca caa aca acc cgg gga aga cga cca      96
Val Leu Val Ser Leu Ser Leu Ala Gln Thr Thr Arg Gly Arg Arg Pro
             20                  25                  30 tca cca cca cca cct tac tac tac aag tct cct cct ccc cca tca cca     144
Ser Pro Pro Pro Pro Tyr Tyr Tyr Lys Ser Pro Pro Pro Pro Ser Pro
         35                  40                  45 tca acc atg gtg agc aag                                             162
Ser Thr Met Val Ser Lys
         50

<210> SEQ ID NO 136
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Ser Ala Met Gly Lys Met Ala Ser Leu Phe Ala Thr Phe Leu Val
 1               5                  10                  15

Val Leu Val Ser Leu Ser Leu Ala Gln Thr Thr Arg Gly Arg Arg Pro
             20                  25                  30

Ser Pro Pro Pro Pro Tyr Tyr Tyr Lys Ser Pro Pro Pro Pro Ser Pro
         35                  40                  45

Ser Thr Met Val Ser Lys
         50

<210> SEQ ID NO 137
<211> LENGTH: 162
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(162)

<400> SEQUENCE: 137 gga tcc gca atg gga aaa atg gct tct cta ttt gcc aca ttt tta gtg      48
Gly Ser Ala Met Gly Lys Met Ala Ser Leu Phe Ala Thr Phe Leu Val
 1               5                  10                  15 gtt tta gtg tca ctt agc tta gca caa aca acc cgg gga aga cga cca      96
Val Leu Val Ser Leu Ser Leu Ala Gln Thr Thr Arg Gly Arg Arg Pro
             20                  25                  30
```

```
tca cca cca cca cct tac tac tac cta tct cct cct ccc cca tca cca    144
Ser Pro Pro Pro Pro Tyr Tyr Tyr Leu Ser Pro Pro Pro Ser Pro
        35                  40                  45 tca acc atg gtg agc aag                                             162
Ser Thr Met Val Ser Lys
    50
```

<210> SEQ ID NO 138
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Gly Ser Ala Met Gly Lys Met Ala Ser Leu Phe Ala Thr Phe Leu Val
1               5                   10                  15

Val Leu Val Ser Leu Ser Leu Ala Gln Thr Thr Arg Gly Arg Arg Pro
            20                  25                  30

Ser Pro Pro Pro Pro Tyr Tyr Tyr Leu Ser Pro Pro Pro Ser Pro
        35                  40                  45

Ser Thr Met Val Ser Lys
    50
```

<210> SEQ ID NO 139
<211> LENGTH: 165
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(165)

<400> SEQUENCE: 139

```
gga tcc gca atg gga aaa atg gct tct cta ttt gcc aca ttt tta gtg     48
Gly Ser Ala Met Gly Lys Met Ala Ser Leu Phe Ala Thr Phe Leu Val
1               5                   10                  15 gtt tta gtg tca ctt agc tta gca caa aca acc cgg gcc tca cca cca     96
Val Leu Val Ser Leu Ser Leu Ala Gln Thr Thr Arg Ala Ser Pro Pro
            20                  25                  30 cca cct agt ccg tca ccc cct ccc cca ttt ttc ttt aag agc cca cca    144
Pro Pro Ser Pro Ser Pro Pro Pro Phe Phe Phe Lys Ser Pro Pro
        35                  40                  45 cca cct tcc atg gtg agc aag                                         165
Pro Pro Ser Met Val Ser Lys
    50                  55
```

<210> SEQ ID NO 140
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Gly Ser Ala Met Gly Lys Met Ala Ser Leu Phe Ala Thr Phe Leu Val
1               5                   10                  15

Val Leu Val Ser Leu Ser Leu Ala Gln Thr Thr Arg Ala Ser Pro Pro
            20                  25                  30
```

```
Pro Pro Ser Pro Ser Pro Pro Pro Pro Phe Phe Phe Lys Ser Pro Pro
        35              40                      45

Pro Pro Ser Met Val Ser Lys
    50              55

<210> SEQ ID NO 141
<211> LENGTH: 162
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(162)

<400> SEQUENCE: 141 gga tcc gca atg gga aaa atg gct tct cta ttt gcc aca ttt tta gtg        48
Gly Ser Ala Met Gly Lys Met Ala Ser Leu Phe Ala Thr Phe Leu Val
 1               5                  10                  15 gtt tta gtg tca ctt agc tta gca caa aca acc cgg gga aga cga cca        96
Val Leu Val Ser Leu Ser Leu Ala Gln Thr Thr Arg Gly Arg Arg Pro
            20                  25                  30 tca cca cca cca cct ttt ttc ttt cta tct cct cct ccc cca tca cca       144
Ser Pro Pro Pro Pro Phe Phe Phe Leu Ser Pro Pro Pro Pro Ser Pro
        35                  40                  45 tca acc atg gtg agc aag                                                162
Ser Thr Met Val Ser Lys
    50
```